United States Patent
Chen et al.

(10) Patent No.: US 9,340,524 B2
(45) Date of Patent: May 17, 2016

(54) ANDROGEN RECEPTOR MODULATOR AND USES THEREOF

(71) Applicant: Aragon Pharmaceuticals, Inc., San Diego, CA (US)

(72) Inventors: Isan Chen, San Diego, CA (US); Jeffrey H Hager, San Diego, CA (US); Edna Chow Maneval, San Diego, CA (US); Mark R Herbert, San Diego, CA (US); Nicholas D Smith, San Diego, CA (US)

(73) Assignee: Aragon Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 14/151,106

(22) Filed: Jan. 9, 2014

(65) Prior Publication Data
US 2014/0199236 A1 Jul. 17, 2014

Related U.S. Application Data

(60) Provisional application No. 61/752,842, filed on Jan. 15, 2013.

(51) Int. Cl.
| | |
|---|---|
| *A61K 51/00* | (2006.01) |
| *A61M 36/14* | (2006.01) |
| *C07D 401/04* | (2006.01) |
| *A61K 31/337* | (2006.01) |
| *A61K 31/4025* | (2006.01) |
| *A61K 31/436* | (2006.01) |
| *A61K 31/4439* | (2006.01) |
| *A61K 31/5377* | (2006.01) |
| *A61K 31/58* | (2006.01) |
| *A61K 38/09* | (2006.01) |
| *A61K 39/395* | (2006.01) |
| *A61K 51/02* | (2006.01) |
| *A61K 51/10* | (2006.01) |
| *A61K 45/06* | (2006.01) |
| *A61K 9/48* | (2006.01) |
| *A61K 47/10* | (2006.01) |
| *A61K 9/00* | (2006.01) |

(52) U.S. Cl.
CPC ............ *C07D 401/04* (2013.01); *A61K 9/4825* (2013.01); *A61K 31/337* (2013.01); *A61K 31/4025* (2013.01); *A61K 31/436* (2013.01); *A61K 31/4439* (2013.01); *A61K 31/5377* (2013.01); *A61K 31/58* (2013.01); *A61K 38/09* (2013.01); *A61K 39/39558* (2013.01); *A61K 45/06* (2013.01); *A61K 51/025* (2013.01); *A61K 51/1096* (2013.01); *A61K 9/0019* (2013.01); *A61K 9/0024* (2013.01); *A61K 47/10* (2013.01)

(58) Field of Classification Search
CPC ............ A61K 9/00; A61K 9/48; A61K 51/00; A61K 51/025; A61K 51/1096; A61K 31/00; A61K 31/337; A61K 31/436; A61K 31/4025; A61K 31/4439; A61K 31/5377; A61K 31/58; A61K 45/00; A61K 45/06; A61K 47/00; A61K 47/10; A61K 47/34; A61K 47/44; A61K 39/39558; A61K 9/0019; A61K 9/0024; A61K 9/4825; A61K 38/09; A61K 2300/00; C07D 401/04; C07D 211/06; C07D 295/00; C07D 213/02; C07D 233/04; C07D 233/54
USPC ............ 424/1.11, 1.65, 1.81, 9.1; 514/1, 183, 514/186, 188; 534/7, 10–16; 546/184, 255; 548/335.1, 347.1
See application file for complete search history.

(56) References Cited

U.S. PATENT DOCUMENTS

| | | |
|---|---|---|
| 3,823,240 A | 7/1974 | Sauli |
| 3,984,430 A | 10/1976 | Curran |
| 4,097,578 A | 6/1978 | Perronnet et al. |
| 4,229,447 A | 10/1980 | Porter |
| 4,234,736 A | 11/1980 | Bernauer et al. |

(Continued)

FOREIGN PATENT DOCUMENTS

| | | |
|---|---|---|
| AU | 217893 | 6/1958 |
| CN | 101032483 | 9/2007 |

(Continued)

OTHER PUBLICATIONS

Godbole et al, Prostate Cancer, 2011, pp. 1-13.*

(Continued)

*Primary Examiner* — D L Jones
(74) *Attorney, Agent, or Firm* — Baker & Hostetler LLP

(57) ABSTRACT

Described herein is the androgen receptor modulator of formula (I)

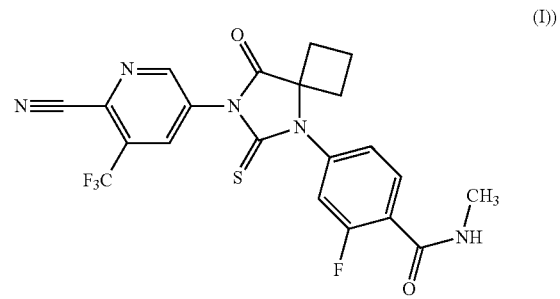

in the treatment of prostate cancer in combination with other therapeutic options and in the treatment of diseases or conditions that are amenable to treatment with the androgen receptor modulator, as well as pharmaceutical compositions and medicaments that include such compound.

4 Claims, No Drawings

(56) References Cited

U.S. PATENT DOCUMENTS

| | | | |
|---|---|---|---|
| 4,304,782 A | 12/1981 | Dumont et al. |
| 4,312,881 A | 1/1982 | Wootton |
| 4,399,216 A | 8/1983 | Axel et al. |
| 4,407,814 A | 10/1983 | Bernauer et al. |
| 4,427,438 A | 1/1984 | Nagano et al. |
| 4,473,393 A | 9/1984 | Nagpal |
| 4,482,739 A | 11/1984 | Bernauer et al. |
| 4,559,157 A | 12/1985 | Smith et al. |
| 4,596,795 A | 6/1986 | Pitha |
| 4,608,392 A | 8/1986 | Jacquet et al. |
| 4,749,403 A | 6/1988 | Liebl et al. |
| 4,755,386 A | 7/1988 | Hsiao et al. |
| 4,820,508 A | 4/1989 | Wortzman |
| 4,859,228 A | 8/1989 | Prisbylla |
| 4,873,256 A | 10/1989 | Coussediere et al. |
| 4,938,949 A | 7/1990 | Borch et al. |
| 4,944,791 A | 7/1990 | Schroder et al. |
| 4,992,478 A | 2/1991 | Geria |
| 5,010,182 A | 4/1991 | Brake et al. |
| 5,011,692 A | 4/1991 | Fujioka et al. |
| 5,017,381 A | 5/1991 | Maruyama et al. |
| 5,033,252 A | 7/1991 | Carter |
| 5,052,558 A | 10/1991 | Carter |
| 5,069,711 A | 12/1991 | Fischer et al. |
| 5,071,773 A | 12/1991 | Evans et al. |
| 5,166,358 A | 11/1992 | Seuron et al. |
| 5,229,135 A | 7/1993 | Philippon et al. |
| 5,323,907 A | 6/1994 | Kalvelage |
| 5,411,981 A | 5/1995 | Gaillard-Kelly et al. |
| 5,434,176 A | 7/1995 | Claussner et al. |
| 5,554,607 A | 9/1996 | Elokdah et al. |
| 5,556,983 A | 9/1996 | Claussner et al. |
| 5,589,497 A | 12/1996 | Claussner et al. |
| 5,614,620 A | 3/1997 | Liao et al. |
| 5,627,201 A | 5/1997 | Gaillard-Kelly et al. |
| 5,646,172 A | 7/1997 | Claussner et al. |
| 5,656,651 A | 8/1997 | Sovak et al. |
| 5,705,654 A | 1/1998 | Claussner et al. |
| 5,726,061 A | 3/1998 | Robbins et al. |
| 5,739,136 A | 4/1998 | Ellinwood, Jr. et al. |
| 5,750,553 A | 5/1998 | Claussner et al. |
| 5,783,707 A | 7/1998 | Elokdah et al. |
| RE35,956 E | 11/1998 | Gaillard-Kelly et al. |
| 5,837,284 A | 11/1998 | Mehta et al. |
| 5,840,329 A | 11/1998 | Bai |
| 5,958,936 A | 9/1999 | Claussner et al. |
| 5,968,875 A | 10/1999 | Bis et al. |
| 5,985,868 A | 11/1999 | Gray |
| 6,107,488 A | 8/2000 | Bouchet et al. |
| 6,172,076 B1 | 1/2001 | Embrey et al. |
| 6,235,910 B1 | 5/2001 | Beller et al. |
| 6,242,611 B1 | 6/2001 | Claussner et al. |
| 6,307,030 B1 | 10/2001 | French et al. |
| 6,350,763 B1 | 2/2002 | Kelly et al. |
| 6,472,415 B1 | 10/2002 | Sovak et al. |
| 6,479,063 B2 | 11/2002 | Weisman et al. |
| 6,489,163 B1 | 12/2002 | Roy et al. |
| 6,506,607 B1 | 1/2003 | Shyjan |
| 6,710,037 B2 * | 3/2004 | Wang et al. ............ 514/44 R |
| 6,828,471 B2 | 12/2004 | Sawyers et al. |
| 7,271,188 B2 | 9/2007 | Tachibana et al. |
| 8,445,507 B2 * | 5/2013 | Jung et al. ............ 514/278 |
| 8,461,343 B2 | 6/2013 | Ouerfelli et al. |
| 2002/0133833 A1 | 9/2002 | Sawyers et al. |
| 2003/0225138 A1 | 12/2003 | Sircar et al. |
| 2004/0009969 A1 | 1/2004 | Cleve et al. |
| 2004/0077605 A1 | 4/2004 | Salvati et al. |
| 2004/0116417 A1 | 6/2004 | Boubia et al. |
| 2005/0153968 A1 | 7/2005 | Bi et al. |
| 2006/0127902 A1 | 6/2006 | Madden et al. |
| 2007/0249697 A1 | 10/2007 | Tachibana et al. |
| 2013/0045204 A1 | 2/2013 | Andersen et al. |
| 2013/0072511 A1 | 3/2013 | Jung et al. |
| 2013/0079241 A1 | 3/2013 | Luo et al. |
| 2013/0116258 A1 | 5/2013 | Smith et al. |
| 2013/0225821 A1 | 8/2013 | Ouerfelli et al. |
| 2013/0253035 A1 | 9/2013 | McDonnell et al. |
| 2014/0088129 A1 | 3/2014 | Chen |

FOREIGN PATENT DOCUMENTS

| | | |
|---|---|---|
| DE | 2102605 | 7/1971 |
| DE | 2614831 | 10/1977 |
| EP | 0017976 | 10/1980 |
| EP | 0002259 | 10/1984 |
| EP | 0144098 | 6/1985 |
| EP | 0331232 | 9/1989 |
| EP | 0362179 | 4/1990 |
| EP | 0494819 | 1/1992 |
| EP | 0572191 | 12/1993 |
| EP | 0578516 | 1/1994 |
| EP | 0580459 | 1/1994 |
| EP | 0770613 | 5/1997 |
| EP | 0721944 | 1/2001 |
| EP | 1632477 | 3/2006 |
| EP | 1790640 | 5/2007 |
| FR | 2693461 | 1/1994 |
| FR | 2715402 | 7/1995 |
| FR | 2845384 | 4/2004 |
| JP | 59210083 | 11/1984 |
| JP | 1009978 | 1/1989 |
| JP | 0219363 | 1/1990 |
| WO | WO 90/13646 | 11/1990 |
| WO | WO 97/00071 | 1/1997 |
| WO | WO 97/19064 | 5/1997 |
| WO | WO 97/19931 | 6/1997 |
| WO | WO 00/17163 | 3/2000 |
| WO | WO 00/26195 | 5/2000 |
| WO | WO 00/44731 | 8/2000 |
| WO | WO 01/07048 | 2/2001 |
| WO | WO 01/92253 | 12/2001 |
| WO | WO 01/94346 | 12/2001 |
| WO | WO 02/053155 | 7/2002 |
| WO | WO 02/081453 | 10/2002 |
| WO | WO 03/029245 | 4/2003 |
| WO | WO 03/032994 | 4/2003 |
| WO | WO 03/057220 | 7/2003 |
| WO | WO 03/093243 | 11/2003 |
| WO | WO 03/096980 | 11/2003 |
| WO | WO 2004/022572 | 3/2004 |
| WO | WO 2004/031160 | 4/2004 |
| WO | WO 2004/070050 | 8/2004 |
| WO | WO 2004/111031 | 12/2004 |
| WO | WO 2005/042488 | 5/2005 |
| WO | WO 2005/059109 | 6/2005 |
| WO | WO 2005/060661 | 7/2005 |
| WO | WO 2005/089752 | 9/2005 |
| WO | WO 2005/099693 | 10/2005 |
| WO | WO 2006/010642 | 2/2006 |
| WO | WO 2006/028226 | 3/2006 |
| WO | WO 2006/124118 | 11/2006 |
| WO | WO 2007/045877 | 4/2007 |
| WO | WO 2007/126765 | 11/2007 |
| WO | WO 2007/127010 | 11/2007 |
| WO | WO 2008/119015 | 10/2008 |
| WO | WO 2009/055053 | 4/2009 |
| WO | WO 2010/099238 | 9/2010 |
| WO | WO 2011/106570 | 9/2011 |
| WO | WO 2012/158884 | 11/2012 |
| WO | WO 2013/079964 | 6/2013 |

OTHER PUBLICATIONS

Clegg et al, Cancer Research, 2012, vol. 72, No. 6, pp. 1494-1503 (Published onlind on Jan. 20, 2012).*
Sarker et al, Clin. Cancer Res., 2009, vol. 15, No. 15, pp. 4799-4805.*
Hwang et al, Journal of Hematology & Oncology, 2010, vol. 3, No. 26, pp. 1-12.*
Body, Annal of Oncology, 2010, vol. 21, Supplement 7, vii180-vii185.*
Osanto et al, Ther. Adv. Urol., 2012, vol. 4, No. 1, pp. 3-12.*
Genentech, Oct. 2011, A Phase I, Open-Label Study of the Safety and Pharmacokinetics of Escalating Doses of DSTP 3086S in Patients with Metastatic Castration-Resistant Prostate Cancer, 2 pages.*

(56) References Cited

OTHER PUBLICATIONS

Gomella, Rev. Urol., 2009, vol. 11, No. 2, pp. 52-60.*
Cook et al (The Oncologist, 2000, vol. 5, pp. 162-168).*
Hormonal Treatments for Uterine Fibroids (http://www.uterine-fibroids.org/Hormonal_Treatments.html, 2010).*
Depalo et al (Reproductive Biology and Endocrinology, 2012, vol. 10, pp. 26-33).*
Auricchio et al (European Oncology & Haematology, 2012, vol. 8, No. 1, pp. 32-35).*
"ARN-509 Update: Phase I Study—Prostrate Cancer", HealingWell.com, 2014, 3 pages.
"Castration-Resistant Prostrate Cancer", American Urological Association, www.auanet.org/education/guidelines/castration-resistant-prostate-cancer.cfm, 2015, 21 pages.
Ausubel et al., "Current Protocols in Molecular Biology", Wiley Interscience Publishers, 1995, 2, 18 pages.
Baek et al., "Exchange of N-CoR Corepressor and Tip60 Coactivator Complexes Links Gene Expression by NF-kappaB and Beta-Amyloid Precursor Protein", Cell, 2002, 110, 55-67.
Balk, "Androgen Receptor as a Target in Androgen-Independent Prostate Cancer", Urology, 2002, 60(3A), 132-138.
Batch et al., "Androgen Receptor Gene Mutations Identified by SSCP in Fourteen Subjects with Androgen Insensitivity Syndrome", Hum. Mol. Genet., 1992, 1(7), 497-503.
Bohl et al., "Structural Basis for Antagonism and Resistance of Bicalutamide in Prostate Cancer", Proc. Nat. Acad. Sci., 2005, 102(17), 6201-6206.
Brockschmidt et al., "The Two Most Common Alleles of the Coding GGN Repeat in the Androgen Receptor Gene Cause Differences in Protein Function", J. Mol. Endocrinol., 2007, 39, 1-8.
Bundgaard, "Design of Application of Prodrugs", Harwood Academic Publishers, 1991, Chapter 5, 113-191.
Burnstein et al., "Androgen Glucocorticoid Regulation of Androgen Receptor cDNA Expression", Molecular and Cellular Endocrinology, 1995, 115, 177-186.
Butler, "Mammalian Cell Biotechnology: A Practical Approach", 1991, 6 pages.
Cai et al., "c-Jun Has Multiple Enhancing Activities in the Novel Cross Talk Between the Androgen Receptor and ETS Variant Gene 1 in Prostate Cancer", Mol. Cancer Res., 2007, 5(7), 725-735.
Carver et al., "Reciprocal Feedback Regulation of PI3K and Androgen Receptor Signaling in PTEN-Deficient Prostate Cancer", Cancer Cell., 2011, 19, 575-586.
Chang et al., "Molecular Cloning of Human and Rat Complementary DNA Encoding Androgen Receptors", Science, 1988, 240, 324-326.
Chen et al., "Molecular Determinants of Resistance to Antiandrogen Therapy", Nature Medicine, 2004, 10(1), 33-39.
Chobanian et al., "A Facile Microwave-Assisted Palladium-Catalyzed Cyanation of Aryl Chlorides", Tetrahed Lett., 2006, 47(19), 3303-3035.
Cinar et al. "Androgen Receptor Mediates the Reduced Tumor Growth, Enhanced Androgen Responsiveness, and Selected Target Gene Transactivation in Human Prostate Cancer Cell Line", Cancer Research, 2001, 61, 7310-7317.
Cousty-Berlin, et al., "Preliminary Pharmacokinetics and Metabolism of Novel Non-steroidal Antiandrogens in the Rat: Relation of their Systemic Activity to the Formation of a Common Metabolite", J. Steroid Biochem. Molecular Bio., 1994, 51(1/2), 47-55.
Craft et al., "A Mechanism for Hormone-Independent Prostate Cancer Through Modulation of Androgen Receptor Signaling by the HER-2/Neu Tyrosine Kinase", Nature Medicine, 1999, 5(3), 280-285.
Craft et al., "Evidence for Clonal Outgrowth of Androgen-Independent Prostate Cancer Cells from Androgen-Dependent Tumors Through a Two-Step Process", Cancer Res, 1999, 59,5030-5036.
Creaven et al., "Pharmacokinetics and Metabolism of Nilutamide", Supp. Urology, 1991, 37(2), 13-19.
DePrimo et al. "Transcriptional Programs Activated by Exposure of Human Prostate Cancer Cells to Androgen", Genome Biology, 2002, 3(7), 1-12.

Dhal et al., "Synthesis of Thiohydantoins, Thiazolidones and their Derivatives from N1-(4'-aryl thiazole 2'-YL) Thioureas", J. Indian Chem. Soc., 1973, 50(1), 680-684.
Edwards et al., "Androgen Receptor Gene Amplification and Protein Expression in Hormone Refractory Prostate Cancer", British Journal of Cancer, 2003, 89, 552-556.
Ellis et al., "Characterization of a Novel Androgen-Sensitive, Prostate-Specific Antigen-Producing Prostatic Carcinoma Xenograft: LuCaP 23", Clin Cancer Res, 1996, 2, 1039-1048.
Ellwood-Yen et al., "Myc-Driven Murine Prostate Cancer Shares Molecular Features with Human Prostate Tumors", Cancer Cell, 2003, 4(3), 223-238.
Elokdah et al., "Design, Synthesis, and Biological Evaluation of Thio-Containing Compounds with Serum HDL-Cholesterol-Elevating Properties", J. Med. Chem., 2004, 47(3), 681-695.
Feher et al., "BHB: A Simple Knowledge-Based Scoring Function to Improve the C95 Efficiency of Database Screening", J. Chem. Inf. Comput. Sci., 2003, 43(4), 1316-1327.
Feldman et al., "The Development of Androgen-Independent Prostate Cancer", Nature Reviews Cancer, 2001, 1, 34-45.
Foks et al., "Synthesis, Fungicidal and Antibacterial Activity of New Pyridazine Derivatives", Heterocycles, 2009, 78(4), 961-975.
Font de Mora et al., "AIB1 is a Conduit for Kinase-Mediated Growth Factor Signaling to the Estrogen Receptor", Mol. Cell. Biol., 2000, 20(14), 5041-5047.
Foury et al., "Control of the Proliferation of Prostate Cancer Cells by an Androgen and Two Antiandrogens. Cell Specific Sets of Responses", J. Steroid Biochem. Molec. Bioi., 1998, 66(4), 235-240.
Gelmann, "Molecular Biology of the Androgen Receptor", J. Clin. Oncol., 2002, 20, 3001-3015.
Gioeli et al., "Androgen Receptor Phosphorylation Regulation and Identification of the Phosphorylation Sites", J Biol Chem, 2002, 277(32), 29304-29314.
Glass et al., "The Coregulator Exchange on Transcriptional Functions of Nuclear Receptors", Genes Dev., 2000, 14, 121-141.
Goubet et al., "Conversion of a Thiohydantoin to the Corresponding Hydantoin via a Ring-Opening/Ring Closure Mechanism", Tetrahedron Letters, 1996, 37(43), 7727-7730.
Grad et al., "Multiple Androgen Response Elements and a Myc Consensus Site in the Androgen Receptor (AR) Coding Region are Involved in Androgen-Mediated Up-Regulation of AR Messenger RNA", Mol Endocrinol, 1999, 13, 1896-1911.
Graham et al., "A New Technique for the Assay of Infectivity of Human Adenovirus 5 DNA", Virology, 1973, 52, 456-467.
Gregory et al., "A Mechanism for Androgen Receptor-Mediated Prostate Cancer Recurrence After Androgen Deprivation Therapy", Cancer Res., 2001, 61, 4315-4319.
Gregory et al., "Androgen Receptor Stabilization in Recurrent Prostate Cancer is Associated with Hypersensitivity to Low Androgen", Cancer Res, 2001, 61, 2892-2898.
Hamilton-Reeves et al, "Isoflavone-Rich Soy Protein Isolate Suppresses Androgen Receptor Expression Without Altering Estrogen Receptor-Beta Expression or Serum Hormonal Profiles in Men at High Risk of Prostate Cancer", J. Nutr., 2007, 137, 1769-1775.
Heath et al., "A Phase I Dose-Escalation Study of Oral BR-DIM (Bioresponse 3.3 Diindolylmethane) in Castrate-Resistant, Non-Metastatic Prostate Cancer", American Journal of Translational Research, 2010, 2(4), 402-411.
Higuchi et al., "Pro-Drugs as Novel Delivery Systems", 1975, vol. 14 of the A.C.S. Symposium Series, 6 pages.
Holzbeierlein et al., "Gene Expression Analysis of Human Prostate Carcinoma During Hormonal Therapy Identifies Androgen-Responsive Genes and Mechanisms of Therapy Resistance", Am. J. Pathology, 2004, 164(1), 217-227.
Homma et al., "Differential Levels of Human Leukocyte Antigen-Class I, Multidrugresistance 1 and Androgen Receptor Expressions in Untreated Prostate Cancer Cells: The Robustness of Prostate Cancer", Oncol. Rep., 2007, 18, 343-346.
Horoszewicz et al., "LNCaP Model of Human Prostatic Carcinoma", Cancer Res., 1983, 43, 1809-1818.
Huang et al., "AR Possess an Intrinsic Hormone-Independent Transcriptional Activity", Mol Endocrinol., 2002, 16(5), 924-937.

(56) References Cited

OTHER PUBLICATIONS

Jones, "Proteinase Mutants of *Saccharomyces cerevisae*", Genetics, 1977, 85, 23-33.
Kagabu, "Methyl, Trifluoromethyl, and Methoxycarbonyl-Introduction to the Fifth Position on the Pyridine Ring of Chloronicotinyl Insecticide Imidacloprid", Synth Comm. 2006, 36(9), 1235-1245.
Karp et al., Prostate Cancer Prevention: Investigational Approaches and Opportunities, Cancer Res., 1996, 56, 5547-5556.
Karvonen et al., "Interaction of Androgen Receptors with Androgen Response Element in Intact Cells", The Journal of Biological Chemistry, 1997, 272(25), 15973-15979.
Kato et al., "Activation of the Estrogen Receptor through Phosphorylation by Mitogenactivated Protein Kinase", Science, 1995, 270, 1491-1494.
Kawai et al., "Site-Specific Fluorescent Labeling of Rna Molecules by Specific Transcription Using Unnatural Base Pairs", J. Am Chem. Soc., 2005, 127(49), 17286-17295.
Kemppainen et al., "Distinguishing Androgen Receptor Agonists and Antagonists: Distinct Mechanisms of Activation by Medroxyprogesterone Acetate and Dihydrotestosterone", Mol. Endocrinol., 1999, 13, 440-454.
Keown et al., "Methods for Introducing DNA Into Mammalian Cells", Methods in Enzymology, 1990, 185, 527-537.
Kingsman et al., "Replication in *Saccharomyces cerevisiae* of Plasmid pBR313 Carrying DNA from the Yeast trpl Region", Gene, 1979, 7, 141-152.
Kinoshita et al., "Methylation of the Androgen Receptor Minimal Promoter Silences Transcription in Human Prostate Cancer", Cancer Res, 2000, 60, 3623-3630.
Klein et al., "Progression of Metastatic Human Prostate Cancer to Androgen Independence in Immunodeficient SCID Mice", Nat Med, 1997, 3(4), 402-408.
Kliment, "Re: Salvage Therapy with Bicalutamide 150 mg in Nonmetastatic Castration-Resistant Prostate Cancer", European Urology, 2011, 59(6), 1066-1067.
Kousteni et al., "Nongenotropic, Sex-Nonspecific Signaling through the Estrogen or Androgen Receptors: Dissociation from Transcriptional Activity", Cell, 2001, 104, 719-730.
Kuethe et al., "Synthesis of Disubstituted Imidazo[4,5-b]pyridin-2-ones", J. Org. Chem., 2004, 29, 69(22), 7752-7754.
Laitinen et al., "Chromosomal Aberrations in Prostate Cancer Xenografts Detected by Comparatove Genomic Hybridization", Genes Chromosomes Cancer, 2002, 35, 66-73.
Li et al., "Heterogeneous Expression and Functions of Androgen Receptor Co-Factors in Primary Prostate Cancer", Am J Pathol, 2002, 161(4), 1467-1474.
Linja et al., "Amplification and Overexpression of Androgen Receptor Gene in Hormone-Refractory Prostate Cancer", Cancer Research, 2001, 61, 3550-3555.
Lobaccaro et al., "Molecular Modeling and In Vitro Investigations of the Human Androgen Receptor DNA-Binding Domain: Application for the Study of Two Mutations", Mol. Cell. Endocrinol., 1996, 116, 137-147.
Lu et al., "Molecular Mechanisms of Androgen-Independent Growth of Human Prostate Cancer LNCaP-Al Cells", Endocrinol., 1999, 140(11), 5054-5059.
Manolagas et al., "Sex Steroids and Bone", Recent Prog Horm Res, 2002, 57, 385-409.
Mansour et al., "Disruption of the Proto-Oncogene int-2 in Mouse Embryo-Derived Stem Cells: A General Strategy for Targeting Mutations to Non-Selectable Genes", Nature, 1988, 336, 348-352.
Marhefka et al., "Homology Modeling Using Multiple Molecular Dynamics Simulations and Docking Studies of the Human Androgen Receptor Ligand Binding Domain Bound to Testosterone and Nonsteroidal Ligands", J. Med. Chem., 2001, 44(11), 1729-1740.
Masiello et al., "Bicalutamide Functions as an Androgen Receptor Antagonist by Assembly of a Transcriptionally Inactive Receptor", J Biol Chem, 2002, 277(29), 26321-26326.
Matias et al., "Local Inhibition of Sebaceous Gland Growth by Topically Applied RU 58841", NY Acad. Sci., 1995, 761, 56-65.
Matias et al., "Structural Basis for the Glucocorticoid Response in a Mutant Human Androgen Receptor (AR(ccr)) Derived from an Androgen-Independent Prostate Cancer", J Med Chem, 2002, 45, 1439-1446.
Matias et al., "Structural Evidence for Ligand Specificity in the Binding Domain of the Human Androgen Receptor: Implications for Pathogenic Gene Mutations", J Biol Chem, 2000, 275(34), 26164-26171.
McDonnell et al., "Expression of the Protooncogene bcl-2 in the Prostate and its Association with Emergence of Androgen-Independent Prostate Cancer", Cancer Res, 1992, 52, 6940-6944.
Migliaccio et al., "Steroid-Induced Androgen Receptor-Oestradiol Receptor beta-SRC Complex Triggers Prostate Cancer Cell Proliferation", Embo J, 2000, 19(20), 5406-5417.
Mulholland et al., "Cell Autonomous Role of PTEN in Regulating Castration-Resistant Prostate Cancer Growth", Cancer Cell., 2011, 19, 792-804.
Muller et al., "BCR First Exon Sequences Specifically Activate the BCRIABL Tyrosine Kinase Oncogene of Philadelphia ChromosomePositive Human Leukemias", Mol. & Cell, Biol., 1991, 11(4), 1785-1792.
Naik et al., "Synthesis, Spectroscopic and Thermal Studies of Bivalent Transition Metal Complexes with the Hydrazone Derived from 2-Benzimidazolyl Mercaptoaceto Hydrazile and o-Hydroxy Aromatic Aldehyde", Indian Journal of Chemistry, 2008, 1793-1797.
Nam et al., "Action of the Src Family Kinase Inhibitor, Dasatinib (BMS-354825), on Human Prostate Cancer Cells", Cancer Res., 2005, 65(20), 9185-9189.
Navone et al., "Model Systems of Prostate Cancer: Uses and Limitations", Cancer Metastasis, 1999, 17, 361-371.
NCBI, "Definition: *Homo sapiens* Androgen", Nucleotide, 2007, 7 pages NM_000044<http://www.ncbi.nlm.nih.gov:80/entrez/viewer.fcgi?cmd=Retrieve&db=nucleotide&list_uids=21322251&dopt=GenBank&term=sapiens+AR+androgen+receptor+prostate+cancer&qty=1>gi:21322251.
Norris et al. "Peptide Antagonists of the Human Estrogen Receptor", Science, 1999, 285, 744-746.
Ouk et al., "Development of Androgen Receptor Inhibitors for Hormone-Refractory Prostate Cancer", Prostate Cancer Foundation Meeting, Scottsdale, AZ, Sep. 29-Oct. 1, 2005, 1 page.
Perou et al., "Molecular Portraits of Human Breast Tumors", Nature, 2000, 406, 747-752.
"Prostate-Specific Antigen (PSA) Test", National Cancer Institute, 2012, 6 pages.
Raffo et al., "Overexpression of bcl-2 Protects Prostate Cancer Cells from Apoptosis in Vitro and Confers Resistance to Androgen Depletion in Vivo", Cancer Research, 1995, 55, 4438-4445.
Rathkopf et al., "A First-In-Human. Open-Label. Phase 1/11 Safety. Pharmacokinetic and Proof-of-Concept Study of ARN-509 in Patients with Progressive Advanced Castration-Resistant Prostate Cancer (CRPC )", J. of Clin. Oncol.; ASCO Annual Meeting, 2011, 29(15), 2 pages.
Rathkopf et al., "A Phase I Study of the Androgen Signaling Inhibitor ARN-509 in Patients with Metastatic Castration-Resistant Prostate Cancer (mCRPC)", J. Clin. Oncol., 2012, 2 pages.
ReaganShaw et al, "Dose Translation from Animal to Human Studies Revisited", 2007, 22, 659-661.
"Remington: Practice of the Science and Pharmacy", 19th Edition, Table of Contents, Gennaro (ed.), 1995, Mack Publishing Company, Easton, PA, 5 pages.
Rooseboom et al., "Enzyme-Catalyzed Activation of Anticancer Prodrugs", Pharmacological Reviews, 2004, 56, 53-102.
Sack et al., "Crystallographic Structures of the Ligand-Binding Domains of the Androgen Receptor and its T877A Mutant Complexed with the Natural Agonist Dihydrotestosterone", Proc Natl Acad Sci, 2001, 98(9), 4904-4909.
Sambrook et al., "Molecular Cloning: A Laboratory Manual", $2^{nd}$ Edition, Table of Contents, Cold Spring Harbor Laboratory Press, Cold Spring Harbor, 1989, 30 pages.
Saunders et al., "Point Mutations Detected in the Androgen Receptor Gene of Three Men with Partial Androgen Insensitivity Syndrome", Clin. Endocrinol., 1992, 37, 214•220.

(56) References Cited

OTHER PUBLICATIONS

Schellhammer et al., "Prostate Specific Antigen Decreases after Withdrawal of Antiandrogen Therapy with Bicalutamide or Flutamide in Patients Receiving Combined Androgen Blockade", J Urol, 1997, 157, 1731-1735.
Scher et al., "The Flutamide Withdrawal Syndrome: Its Impact on Clinical Trials in Hormone-Refractory Prostatic Cancer", J Clin Oncol 1993, 11, 1566-1572.
Sderholm et al., "Three-Dimensional Structure-Activity Relationships of Nonsteroidal Ligands in Complex with Androgen Receptor Ligand-Binding Domain," J. Med. Chem., 2005, 48(4), 917-925.
Shang et al., "Formation of the Androgen Receptor Transcription Complex", Mol Cell, 2002, 9, 601-610.
Shang et al., "Molecular Determinants for the Tissue Specificity of SERMs", Science, 2002, 295, 2465-2468.
Shi et al., "Functional Analysis of 44 Mutant Androgen Receptors from Human Prostate Cancer", Can Res, 2002, 62(5), 1496-1502.
Shiau et al., "The Structural Basis of Estrogen Receptor/Coactivator Recognition and the Antagonism of this Interaction by Tamoxifen", Cell, 1998, 95, 927-937.
Singh et al., "Androgen Receptor Antagonists (Antiandrogens): Structure-Activity Relationships", Current Medicinal Chemistry, 2000, 7, 211-247.
Smith et al., "ARN-509 in Men with High Risk Non-Metastatic Castration-Resistant Prostate Cancer", Annals of Oncology; Abstract Book of the 37th ESMO Congress, 2012, 23(9), No. Suppl. 9, 1 page.
Smith et al., "ARN-509 in Men with High Risk Non-Metastatic Castration-Resistant Prostate Cancer", European Journal of Cancer; European Cancer Congress, 2013, 49(2), 1 page.
Soto et al., "Control of Cell Proliferation: Evidence for Negative Control on C141 Estrogen-Sensitive T47D Human Breast Cancer Cells", Cancer Research, 1986, 46, 2271-2275.
Sperry et al., Androgen Binding Profiles of Two Distinct Nuclear Androgen Receptors in Atlantic Croaker (*Micropogonias undulates*), Journal of Steroid Biochemistry & Molecular Biology, 2000, 73, 93-103.
Stinchcomb et al., "Isolation and Characterisation of a Yeast Chromosomal Replicator", 1979, 282, 39-43.
Su et al., "Polymorphisms of Androgen Receptor Gene in Childhood and Adolescent Males with First-Onset Major Depressive Disorder and Association with Related Symptomatology", Int. J. Neurosci., 2007, 117, 903-917.
Sweet et al., "A Unique Point Mutation in the Androgen Receptor Gene in a Family with Complete Androgen Insensitivity Syndrome", Fertil. Steril., 1992, 58(4), 703-707.
Szelei et al., "Androgen-Induced Inhibition of Proliferation in Human Breast Cancer MCF7 C138b Cells Transfected with Androgen Receptor", Endocrinology, 1997, 138(4), 1406-1412.
Takemoto et al., "Novel Pottasium Chanel Openers: Synthesis and Pharmacological Evaluation of New N-(substituted-3-pyridyL)-N'-alkylthioureas and Related Compounds", J Med. Chem., 1994, 37(1), 18-25.
Taplin et al. "Selection for Androgen Receptor Mutations in Prostate Cancers Treated with Androgen Antagonist", Cancer Res, 1999, 59, 2511-2555.
Taplin et al., "Androgen Receptor Mutations in Androgen-Independent Prostate Cancer: Cancer and Leukemia Group B Study 9663", J Clin Oncol, 2003, 21, 2673-2678.
Taplin et al., "Mutation of the Androgen-Receptor Gene in Metastatic Androgen Independent Prostate Cancer", N Engl J Med, 1995, 332(21), 1393-1398.
Teutsch et al., "Non-steroidal Antiandrogens: Synthesis and Biological Profile of High-affinity Ligands for the Androgen Receptor", J. Steroid Biochem. Mol. Biol., 1994, 48,111-119.
Tran et al., "Development of a Second-Generation Antiandrogen for Treatment of Advanced Prostate Cancer", Science, 2009, 324(5928), 787-790.
Tremblay et al., "Ligand-Independent Recruitment of SRC-1 to Estrogen Receptor Beta through Phosphorylation of Activation Function AF-1", Mol Cell, 1999, 3, 513-519.
Tschumper et al., "Sequence of a Yeast DNA Fragment Containing a Chromosomal Replicator and the TRP1 Gene", Gene, 1980, 10, 157-166.
Urlaub et al., "Isolation of Chinese Hamster Cell Mutants Deficient in Dihydrofolate Reductase Activity", Proc. Natl. Acad. Sci. USA, 1980, 77(7), 4216-4220.
Van Dort et al., "Design, Synthesis, and Pharmacological Characterization of 4-[4,4-Dimethyl-3-(4-hydroxybutyl)-5-oxo-2-thioxo-1-imidazolidinyl]-2-iodobenzonitrile as a High-Affinity Nonsteroidal Androgen Receptor Ligand", J. Med. Chem., 2000, 43, 3344-3347.
Veldscholte et al., "A Mutation in the Ligand Binding Domain of the Androgen Receptor of Human LNCaP Cells Affects Steroid Binding Characteristics and Response to Antiandrogens", Biochem Biophys Res Commun, 1990, 173, 534-540.
Visakorpi et al., "In Vivo Amplification of the Androgen Receptor Gene and Progression of Human Prostate Cancer", Nat Genetics, 1995, 9, 401-406.
Wainstein et al., "CWR22: Androgen-Dependent Xenograft Model Derived from a Primary Human Prostatic Carcinoma", Cancer Res, 1994, 54, 6049-6052.
Wallen et al., "Androgen Receptor Gene Mutations in Hormone-Refractory Prostate Cancer", J. Pathology, 1999, 189, 559-563.
Wang et al., "Overexpressed Androgen Receptor Linked to p21WAF1 Silencing May Be Responsible for Androgen Independence and Resistance to Apoptosis of a Prostate Cancer Cell Line", Cancer Research, 2001, 61(20), 7544-7551.
Wang et al., "Prostate-Specific Deletion of the Murine Pten Tumor Suppressor Gene Leads to Metastatic Prostate Cancer", Cancer Cell, 2003, 4, 209-221.
Wermuth, "Molecular Variations Based on Isosteric Replacements", The Practice of Medicinal Chemistry, 1996, 13, 203-237.
Wermuth et al., "Designing Prodrugs and Bioprecursors, I: Carrier Prodrugs", The Pharmacological Basis of Therapeutics, The Practice of Medicinal Chemistry, Goodman and Gilman, eds., Macmillan Publishing Co., New York, Chapter 31, 1996, 28 pages.
Wooster et al., "A Germline Mutation in the Androgen Receptor Gene in Two Brothers with Breast Cancer and Reifenstein Syndrome", Nat. Genet., 1992, 2, 132-134.
Zakikhani et al., "Metformin is an AMP Kinase-Dependent Growth Inhibitor for Breast Cancer Cells", Cancer Res, 2006, 66(21), 10269-10273.
Zarghami et al., "Steroid Hormone Regulation of Prostate-Specific Antigen Gene Expression in Breast Cancer", British Journal of Cancer, 1997, 75(4), 579-588.
Zhau et al., "Androgen-Repressed Phenotype in Human Prostate Cancer", Proc Natl Acad Sci USA, 1996, 93,15152-15157.
Zhou et al., "A Ligand-Dependent Bipartite Nuclear Targeting Signal in the Human Androgen Receptor, Requirement for the DNA-Binding Domain and Modulation by NH2-Terminal and Carboxyl-Terminal Sequences", J Bio Chem, 1994, 269(18), 13115-13123.
Zoppi et al., "Amino Acid Substitutions in the DNA-Binding Domain of the Human Androgen Receptor are a Frequent Cause of Receptor-Binding Positive Androgen Resistance", Mol. Endo., 1992, 6, 409-415.

* cited by examiner

ANDROGEN RECEPTOR MODULATOR AND USES THEREOF

CROSS REFERENCE TO RELATED APPLICATIONS

This Application claims the benefit of priority to U.S. Patent Application Ser. No. 61/752,842, filed Jan. 15, 2013, the contents of which are incorporated by reference herein in their entirety for all purposes.

FIELD OF THE INVENTION

Described herein is the use of the androgen receptor modulator 4-[7-(6-cyano-5-trifluoromethylpyridin-3-yl)-8-oxo-6-thioxo-5,7-diazaspiro[3.4]oct-5-yl]-2-fluoro-N-methylbenzamide in the treatment of prostate cancer, breast cancer, androgen dependent hirsutism, androgenic alopecia, uterine fibroids, leiomyoma, endometrial carcinoma or endometriosis, alone or in combination with other therapeutic agents.

BACKGROUND OF THE INVENTION

The androgen receptor ("AR") is a ligand-activated transcriptional regulatory protein that mediates induction of a variety of biological effects through its interaction with endogenous androgens. Endogenous androgens include steroids such as testosterone and dihydrotestosterone. Testosterone is converted to dihydrotestosterone by the enzyme 5 alpha-reductase in many tissues.

The actions of androgens with androgen receptors have been implicated in a number of diseases or conditions, such as prostate cancer, breast cancer, androgen dependent hirsutism, androgenic alopecia, uterine fibroids, leiomyoma, endometrial carcinoma or endometriosis. The androgen receptor modulator 4-[7-(6-cyano-5-trifluoromethylpyridin-3-yl)-8-oxo-6-thioxo-5,7-diazaspiro[3.4]oct-5-yl]-2-fluoro-N-methylbenzamide finds use in the treatment of these diseases or conditions in which androgen receptors play a role.

SUMMARY OF THE INVENTION

In one aspect, described herein is a method of treating advanced prostate cancer in a male human comprising administering 4-[7-(6-cyano-5-trifluoromethylpyridin-3-yl)-8-oxo-6-thioxo-5,7-diazaspiro[3.4]oct-5-yl]-2-fluoro-N-methylbenzamide at a dose of about 30 mg per day to about 480 mg per day to the male human with advanced prostate cancer. In some embodiments, the advanced prostate is cancer castration-sensitive prostate cancer, castration-resistant prostate cancer, or high-risk localized prostate cancer. In some embodiments, the castration-resistant prostate cancer is metastatic castration-resistant prostate cancer. In some embodiments, the metastatic castration-resistant prostate cancer is chemotherapy naïve metastatic castration-resistant prostate cancer or post-abiraterone acetate treated metastatic castration-resistant prostate cancer.

4-[7-(6-Cyano-5-trifluoromethylpyridin-3-yl)-8-oxo-6-thioxo-5,7-diazaspiro[3.4]oct-5-yl]-2-fluoro-N-methylbenzamide may be represented by the structure of Formula (I), and may be used or available as such or as a pharmaceutically acceptable salt thereof.

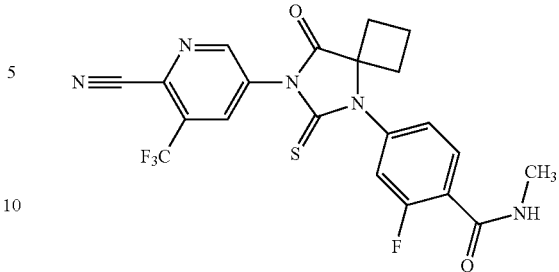

In another aspect, described herein is a method of decreasing prostate-specific antigen levels in a male human with advanced prostate cancer comprising administering 4-[7-(6-cyano-5-trifluoromethylpyridin-3-yl)-8-oxo-6-thioxo-5,7-diazaspiro[3.4]oct-5-yl]-2-fluoro-N-methylbenzamide at a dose of about 30 mg per day to about 480 mg per day to the male human with castration-sensitive prostate cancer, castration-resistant prostate cancer, or high-risk localized prostate cancer. In some embodiments, the prostate-specific antigen levels in the male human are decreased by at least 50% from baseline after 3 months of administering 4-[7-(6-cyano-5-trifluoromethylpyridin-3-yl)-8-oxo-6-thioxo-5,7-diazaspiro[3.4]oct-5-yl]-2-fluoro-N-methylbenzamide on a continuous daily dosing schedule.

In one aspect, described herein is a method of increasing the metastasis free survival (MFS) in a male human with advanced prostate cancer comprising administering 4-[7-(6-cyano-5-trifluoromethylpyridin-3-yl)-8-oxo-6-thioxo-5,7-diazaspiro[3.4]oct-5-yl]-2-fluoro-N-methylbenzamide at a dose of about 30 mg per day to about 480 mg per day to the male human with advanced prostate cancer. In another aspect, described herein is a method of providing survival benefit to a male human with advanced prostate cancer comprising administering 4-[7-(6-cyano-5-trifluoromethylpyridin-3-yl)-8-oxo-6-thioxo-5,7-diazaspiro[3.4]oct-5-yl]-2-fluoro-N-methylbenzamide at a dose of about 30 mg per day to about 480 mg per day to the male human with advanced prostate cancer. In yet another aspect, described herein is a method of providing a delay in symptoms related to disease progression in a male human with advanced prostate cancer comprising administering 4-[7-(6-cyano-5-trifluoromethylpyridin-3-yl)-8-oxo-6-thioxo-5,7-diazaspiro[3.4]oct-5-yl]-2-fluoro-N-methylbenzamide at a dose of about 30 mg per day to about 480 mg per day to the male human with advanced prostate cancer. In some embodiments, the advanced prostate is cancer castration-sensitive prostate cancer, castration-resistant prostate cancer, or high-risk localized prostate cancer. In some embodiments, the castration-resistant prostate cancer is metastatic castration-resistant prostate cancer. In some embodiments, the metastatic castration-resistant prostate cancer is chemotherapy naïve metastatic castration-resistant prostate cancer or post-abiraterone acetate treated metastatic castration-resistant prostate cancer.

In another aspect, described herein is a method of treating breast cancer, androgen dependent hirsutism, androgenic alopecia, uterine fibroids, leiomyoma, endometrial carcinoma or endometriosis in a human comprising administering 4-[7-(6-cyano-5-trifluoromethylpyridin-3-yl)-8-oxo-6-thioxo-5,7-diazaspiro[3.4]oct-5-yl]-2-fluoro-N-methylbenzamide at a dose of about 30 mg per day to about 480 mg per day to a human with breast cancer, androgen dependent hirsutism, androgenic alopecia, uterine fibroids, leiomyoma, endometrial carcinoma or endometriosis.

In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the human in the form of soft-gel capsules.

In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the human in the form of soft-gel capsules at a dose of about 180 mg per day to about 480 mg per day.

In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the human in the form of soft-gel capsules at a dose of about 180 mg per day, about 240 mg per day, about 300 mg per day, about 390 mg per day, or about 480 mg per day.

In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the human in the form of soft-gel capsules at a dose of about 240 mg per day.

In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the human on a continuous daily dosing schedule.

In one aspect, described herein is a method of treating prostate cancer in a male human comprising administering 4-[7-(6-cyano-5-trifluoromethylpyridin-3-yl)-8-oxo-6-thioxo-5,7-diazaspiro[3.4]oct-5-yl]-2-fluoro-N-methylbenzamide at a dose of about 30 mg per day to about 480 mg per day to a male human with metastatic castration-resistant prostate cancer, non-metastatic castration-resistant prostate cancer, metastatic castration-sensitive prostate cancer, non-metastatic castration-sensitive prostate cancer or high-risk localized prostate cancer in combination with a phosphoinositide 3-kinase (PI3K) inhibitor, TORC inhibitor, or dual PI3K/TORC inhibitor. In some embodiments, the method of treating prostate cancer further comprises administering a therapeutically effective amount of a gonadotropin-releasing hormone agonist or antagonist to the male human. In some embodiments, the phosphoinositide 3-kinase (PI3K) inhibitor, TORC inhibitor, or dual PI3K/TORC inhibitor is everolimus, BEZ-235, BKM120, BGT226, BYL-719, GDC0068, GDC-0980, GDC0941, GDC0032, MK-2206, OSI-027, CC-223, AZD8055, SAR245408, SAR245409, PF04691502, WYE125132, GSK2126458, GSK-2636771, BAY806946, PF-05212384, SF1126, PX866, AMG319, ZSTK474, Cal101, PWT33597, LY-317615 (enzastaurin hydrochloride), CU-906, or CUDC-907. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally at a dose of about 120 mg per day to about 240 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally at a dose of about 240 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally in the form of a softgel capsule. In some embodiments, the TORC inhibitor is everolimus. In some embodiments, everolimus is administered at a dose of about 5 mg per day to about 20 mg per day. In some embodiments, everolimus is administered at a dose of about 5 mg per day or about 10 mg per day.

In yet another aspect, described herein is a method of treating prostate cancer in a male human comprising administering 4-[7-(6-cyano-5-trifluoromethylpyridin-3-yl)-8-oxo-6-thioxo-5,7-diazaspiro[3.4]oct-5-yl]-2-fluoro-N-methylbenzamide at a dose of about 30 mg per day to about 480 mg per day to a male human with metastatic castration-resistant prostate cancer, non-metastatic castration-resistant prostate cancer, metastatic castration-sensitive prostate cancer, non-metastatic castration-sensitive prostate cancer or high-risk localized prostate cancer in combination with a CYP17 inhibitor. In some embodiments, the method of treating prostate cancer further comprises administering a therapeutically effective amount of a gonadotropin-releasing hormone agonist or antagonist to the male human. In some embodiments, the CYP17 inhibitor is abiraterone acetate (Zytiga), TAK-700 (orteronel), TOK-001 (galeterone) or VT-464. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally at a dose of about 120 mg per day to about 240 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally at a dose of about 240 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally in the form of a softgel capsule. In some embodiments, the CYP17 inhibitor is abiraterone acetate (Zytiga). In some embodiments, abiraterone acetate (Zytiga) is administered at a dose of about 500 mg per day to about 1000 mg per day. In some embodiments, abiraterone acetate (Zytiga) is administered at a dose of about 1000 mg per day. In some embodiments, abiraterone acetate is administered in combination with prednisone. In some embodiments, abiraterone acetate is administered once a day and prednisone is administered twice a day. In some embodiments, the CYP17 inhibitor is TAK-700 (orteronel). In some embodiments, TAK-700 (orteronel) is administered at a dose of about 300 mg twice per day to about 600 mg twice per day. In some embodiments, TAK-700 (orteronel) is administered at a dose of about 300 mg twice per day to about 600 mg twice per day, together with prednisone at about 5 mg twice per day In one aspect, described herein is a method of treating prostate cancer in a male human comprising administering 4-[7-(6-cyano-5-trifluoromethylpyridin-3-yl)-8-oxo-6-thioxo-5,7-diazaspiro[3.4]oct-5-yl]-2-fluoro-N-methylbenzamide at a dose of about 30 mg per day to about 480 mg per day to a male human with metastatic castration-resistant prostate cancer, non-metastatic castration-resistant prostate cancer, metastatic castration-sensitive prostate cancer, non-metastatic castration-sensitive prostate cancer or high-risk localized prostate cancer in combination with a gonadotropin-releasing hormone agonist or antagonist. Gonadotropin-releasing hormone (GnRH) is also known as Luteinizing-hormone-releasing hormone (LHRH).

In some embodiments, the gonadotropin-releasing hormone agonist or antagonist is Lupron, Zoladex (Goserelin), Degarelix, Ozarelix, ABT-620 (Elagolix), TAK-385 (Relugolix), EP-100 or KLH-2109. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally at a dose of about 120 mg per day to about 240 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally at a dose of about 240 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally in the form of a softgel capsule. In some embodiments, the gonadotropin-releasing hormone agonist or antagonist is Lupron. In some embodiments, Lupron is administered as a depot injection at a dose of about 7.5 mg every 4 weeks, or 22.5 mg every 3 months, or about 30 mg every 4 months, or about 45 mg every 6 months. In some embodiments, the gonadotropin-releasing hormone agonist or antagonist is Zoladex (Goserelin). In some embodiments, Zoladex (Goserelin) is administered as a subcutaneous implant at a dose of about 3.6 mg every 4 weeks or about 10.8 mg every 12 weeks. In some embodiments, the gonadotropin-releasing hormone agonist or antagonist is Degarelix. In some embodiments, Degarelix is administered as a subcutaneous injection at a dose of about 240 mg followed by about 80 mg administered every 4 weeks.

In one aspect, described herein is a method of treating prostate cancer in a male human comprising administering 4-[7-(6-cyano-5-trifluoromethylpyridin-3-yl)-8-oxo-6-thioxo-5,7-diazaspiro[3.4]oct-5-yl]-2-fluoro-N-methylbenzamide at a dose of about 30 mg per day to about 480 mg per day to a male human with metastatic castration-resistant prostate cancer, non-metastatic castration-resistant prostate cancer, metastatic castration-sensitive prostate cancer, non-metastatic castration-sensitive prostate cancer or high-risk localized prostate cancer in combination with an osteoprotective agent. In some embodiments, the method of treating prostate cancer further comprises administering a therapeutically effective amount of a gonadotropin-releasing hormone agonist or antagonist to the male human.

In some embodiments, the osteoprotective agent is Denosumab, AMG-0007, CEP-37251, ALX-0141, Zoledronic acid, Alendronate sodium (Fosamax), Pamidronate disodium (Aredia), Neridronic acid (Nerixia), Minodronic acid (Recalbon) or Risedronate sodium (Actonel). In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally at a dose of about 120 mg per day to about 240 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally at a dose of about 240 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally in the form of a softgel capsule. In some embodiments, the osteoprotective agent is Denosumab. In some embodiments, Denosumab is administered by subcutaneous injection at a dose of about 60 mg to about 120 mg every 4 weeks to every 6 months. In some embodiments, the osteoprotective agent is zoledronic acid. In some embodiments, zoledronic acid is administered by intravenous infusion at a dose of about 4 mg every 4 weeks to every 12 weeks.

In one aspect, described herein is a method of treating prostate cancer in a male human comprising administering 4-[7-(6-cyano-5-trifluoromethylpyridin-3-yl)-8-oxo-6-thioxo-5,7-diazaspiro[3.4]oct-5-yl]-2-fluoro-N-methylbenzamide at a dose of about 30 mg per day to about 480 mg per day to a male human with metastatic castration-resistant prostate cancer, non-metastatic castration-resistant prostate cancer, metastatic castration-sensitive prostate cancer, non-metastatic castration-sensitive prostate cancer or high-risk localized prostate cancer in combination with a radiation therapy. In some embodiments, the method of treating prostate cancer further comprises administering a therapeutically effective amount of a gonadotropin-releasing hormone agonist or antagonist to the male human. In some embodiments, the radiation therapy is Alpharadin, $^{177}$Lu-J591, external beam radiation therapy (including Proton beam), or brachytherapy. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally at a dose of about 120 mg per day to about 240 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally at a dose of about 240 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally in the form of a softgel capsule. In some embodiments, the radiation therapy is Alpharadin. In some embodiments, Alpharadin is administered by intravenous infusion at a dose of about 25 to about 50 kBq/kg every 4 weeks. In some embodiments, the radiation therapy is $^{177}$Lu-J591. In some embodiments, $^{177}$Lu-J591 is administered by intravenous infusion at a dose of about 30 mCi/m2 to about 70 mCi/m2.

In one aspect, described herein is a method of treating prostate cancer in a male human comprising administering 4-[7-(6-cyano-5-trifluoromethylpyridin-3-yl)-8-oxo-6-thioxo-5,7-diazaspiro[3.4]oct-5-yl]-2-fluoro-N-methylbenzamide at a dose of about 30 mg per day to about 480 mg per day to a male human with post-abiraterone acetate treated metastatic castration-resistant prostate cancer, metastatic castration-resistant prostate cancer, non-metastatic castration-resistant prostate cancer, metastatic castration-sensitive prostate cancer, non-metastatic castration-sensitive prostate cancer or high-risk localized prostate cancer in combination with a kinase inhibitor. In some embodiments, the method of treating prostate cancer further comprises administering a therapeutically effective amount of a gonadotropin-releasing hormone agonist or antagonist to the male human. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally at a dose of about 120 mg per day to about 240 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally at a dose of about 240 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally in the form of a softgel capsule. In some embodiments, the kinase inhibitor targets angiogenesis or bone metastases. In some embodiments, the kinase inhibitor is a MET or VEGFR kinase inhibitor. In some embodiments, the kinase inhibitor is Cabozantinib (XL184), PF-2341066 (Crizotinib), ARQ-197 (Tivantinib), MK-2461, JNJ-38877605, MK-8033, INCB-28060, BMS-777607, AMG-208, LY-2801653, EMD-1214063, EMD-1204831, AMG-337, HMPL-504 (Volitinib), SAR-125844, LY2875358, ABR-215050 (Tasquinimod), CHIR-258 (Dovitinib), EXEL-7647, OSI-930, BIBF-1120, BAY-73-4506 (Regorafenib), BMS-582664 (Brivanib), JNJ-26483327, AZD-2171 (Cediranib), Sorafenib, Aflibercept, Enzastaurin, AG-013736 (Axitinib), OSI-632, or GSK-786034 (Pazopanib). In some embodiments, the kinase inhibitor is Cabozantinib. In some embodiments, Cabozantinib is administered orally at a dose of about 40 mg per day to about 100 mg per day. In some embodiments, the kinase inhibitor is an EGFR, MEK, or SRC kinase inhibitor. In some embodiments, the kinase inhibitor is Erlotinib, Cetuximab, Gefitinib, Canertinib, Panitumumab, Nimotuzumab, Lapatinib, Vandetanib, Afatinib, MP-412, AEE-788, Neratinib, XL-647, AC-480, Dacomitinib, AZD-8931, CUDC-101, AP-26113, CO-1686, Trametinib, Selumetinib, MEK-162, Refametinib, TAK-733, RO-5126766, BI-847325, AZD6244, GSK1120212, PF-5208763 (Bosutinib), or AZD-0530 (Saracatinib). In some embodiments, the kinase inhibitor is Erlotinib. In some embodiments, Erlotinib is administered orally at a dose of about 100 mg to about 150 mg. In some embodiments, the kinase inhibitor is Gefitinib. In some embodiments, Gefitinib is administered orally at a dose of about 250 mg. In some embodiments, the kinase inhibitor is Trametinib. In some embodiments, Trametinib is administered orally at a dose of about 1 mg to about 2 mg. In some embodiments, the kinase inhibitor is a AKT, RAF, FGFR, or CDK4/6 kinase inhibitor. In some embodiments, the kinase inhibitor is GDC0068, MK-2206, AT7867, GSK2110183, GSK2141795, GSK690693, Vemurafenib (PLX4032/RG7204), GSK2118436, Dabrafenib (GSK208436), LGX818, RAF265, LY2780301, Dovitinib (TKI258), BGJ398, AZD4547, PD-0332991 or LEE011.

In one aspect, described herein is a method of treating prostate cancer in a male human comprising administering 4-[7-(6-cyano-5-trifluoromethylpyridin-3-yl)-8-oxo-6-thioxo-5,7-diazaspiro[3.4]oct-5-yl]-2-fluoro-N-methylbenzamide at a dose of about 30 mg per day to about 480 mg per day to a male human with metastatic castration-resistant prostate cancer, non-metastatic castration-resistant prostate cancer, metastatic castration-sensitive prostate cancer, non-metastatic castration-sensitive prostate cancer or high-risk localized prostate cancer in combination with PROVENGE™ (sipuleucel-T), PROSTVAC™ (rilimogene galvacirepvec/rilimogene glafolivec), Ipilimumab, or a PD-1 inhibitor. In some embodiments, the method of treating prostate cancer further comprises administering a therapeutically effective amount of a gonadotropin-releasing hormone agonist or antagonist to the male human. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally at a dose of about 120 mg per day to about 240 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally at a dose of about 240 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally in the form of a softgel capsule. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered in combination with Ipilimumab. In some embodiments, Ipilimumab is administered by intravenous infusion at a dose of about 1.5 mg/Kg to about 3.0 mg/kg IV every 3 weeks for a total of 4 doses. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered in combination with a PD-1 inhibitor. In some embodiments, the PD-1 inhibitor is BMS-936558. In some embodiments, the PD-1 inhibitor is BMS-936558 and is administered by intravenous infusion at a dose of about 1.0 mg/kg to about 10 mg/kg on days 1, 15 and 29 of 6-week cycles. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered in combination with PROVENGE™ (sipuleucel-T). In some embodiments, 3 doses of PROVENGE™ (sipuleucel-T) are administered doses at approximately 2 weeks interval. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered in combination with PROSTVAC™ (rilimogene galvacirepvec/rilimogene glafolivec). In some embodiments, Prostvac is administered by subcutaneous injection.

In one aspect, described herein is a method of treating prostate cancer in a male human comprising administering 4-[7-(6-cyano-5-trifluoromethylpyridin-3-yl)-8-oxo-6-thioxo-5,7-diazaspiro[3.4]oct-5-yl]-2-fluoro-N-methylbenzamide at a dose of about 30 mg per day to about 480 mg per day to a male human with metastatic castration-resistant prostate cancer, or high-risk localized prostate cancer in combination with a taxane or tubulin inhibitor. In some embodiments, the method of treating prostate cancer further comprises administering a therapeutically effective amount of a gonadotropin-releasing hormone agonist or antagonist to the male human. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally at a dose of about 120 mg per day to about 240 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally at a dose of about 240 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally in the form of a softgel capsule. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered in combination with Docetaxel. In some embodiments, Docetaxel is administered by intravenous infusion at a dose of about 35 mg/m$^2$ to about 75 mg/m$^2$ every 3 weeks. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered in combination with Cabazitaxel. In some embodiments, Cabazitaxel is administered by intravenous infusion at a dose of about 13 mg/m$^2$ to about 25 mg/m$^2$ every 3 weeks.

In one aspect, described herein is a method of treating prostate cancer in a male human comprising administering 4-[7-(6-cyano-5-trifluoromethylpyridin-3-yl)-8-oxo-6-thioxo-5,7-diazaspiro[3.4]oct-5-yl]-2-fluoro-N-methylbenzamide at a dose of about 30 mg per day to about 480 mg per day to a male human with metastatic castration-resistant prostate cancer, non-metastatic castration-resistant prostate cancer, metastatic castration-sensitive prostate cancer, non-metastatic castration-sensitive prostate cancer or high-risk localized prostate cancer in combination with an anti-STEAP-1 antibody drug conjugate. In some embodiments, the method of treating prostate cancer further comprises administering a therapeutically effective amount of a gonadotropin-releasing hormone agonist or antagonist to the male human. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally at a dose of about 120 mg per day to about 240 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally at a dose of about 240 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally in the form of a softgel capsule. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered in combination with an anti-STEAP-1 antibody drug conjugate. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered in combination with RG7450 (DSTP3086S).

In one aspect, described herein is a method of treating prostate cancer in a male human comprising administering 4-[7-(6-cyano-5-trifluoromethylpyridin-3-yl)-8-oxo-6-thioxo-5,7-diazaspiro[3.4]oct-5-yl]-2-fluoro-N-methylbenzamide at a dose of about 30 mg per day to about 480 mg per day to a male human with metastatic castration-resistant prostate cancer, non-metastatic castration-resistant prostate cancer, metastatic castration-sensitive prostate cancer, non-metastatic castration-sensitive prostate cancer or high-risk localized prostate cancer in combination with a heat shock protein 90 (HSP90) or heat shock protein 27 (HSP27) pathway modulator. In some embodiments, the method of treating prostate cancer further comprises administering a therapeutically effective amount of a gonadotropin-releasing hormone agonist or antagonist to the male human. In some embodiments, 4-[7-(6-cyano-5-trifluoromethylpyridin-3-yl)-8-oxo-6-thioxo-5,7-diazaspiro[3.4]oct-5-yl]-2-fluoro-N-methyl-benzamide is administered orally at a dose of about 120 mg per day to about 240 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally at a dose of about 240 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally in the form of a softgel capsule. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered in combination with OGX-011 (Custirsen), OGX-427, AUY922, HSP990, PF-04928473, PF-04929113 (SNX-5422), Retaspimycin or AT13387. In some embodiments, 4-[7-(6-cyano-5-trifluoromethylpyridin-3-yl)-8-oxo-6-thioxo-5,7-diazaspiro[3.4]oct-5-yl]-2-fluoro-N-methyl-benzamide is administered in combination with OGX-011 (Custirsen). In some embodiments, OGX-011 (Custirsen) is administered by intravenous infusion at a dose of about 320 mg to about 640 mg every week. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered in combination with OGX-427. In some embodiments, OGX-427 is administered by intravenous infusion at a loading dose of about 300 mg to about 600 mg followed by about 500 mg to about 1000 mg every week.

In one aspect, described herein is a pharmaceutical composition comprising a nonaqueous, lipid-based solution of 4-[7-(6-cyano-5-trifluoromethylpyridin-3-yl)-8-oxo-6-thioxo-5,7-diazaspiro[3.4]oct-5-yl]-2-fluoro-N-methylbenzamide in a softgel capsule. In some embodiments, the nonaqueous, lipid-based solution of 4-[7-(6-cyano-5-trifluoromethylpyridin-3-yl)-8-oxo-6-thioxo-5,7-diazaspiro[3.4]oct-5-yl]-2-fluoro-N-methylbenzamide comprises: 4-[7-(6-cyano-5-trifluoromethylpyridin-3-yl)-8-oxo-6-thioxo-5,7-diazaspiro[3.4]oct-5-yl]-2-fluoro-N-methylbenzamide, vitamin E d-α-tocopheryl polyethylene glycol 1000 succinate NF (Vitamin E TPGS), polyethylene glycol 400 NF/EP (PEG 400), glycerol monocaprylocaprate EP and caprylocaproyl macroglycerides EP/NF. In some embodiments, the nonaqueous, lipid-based solution of 4-[7-(6-cyano-5-trifluoromethylpyridin-3-yl)-8-oxo-6-thioxo-5,7-diazaspiro[3.4]oct-5-yl]-2-fluoro-N-methylbenzamide comprises about 3% of 4-[7-(6-cyano-5-trifluoromethylpyridin-3-yl)-8-oxo-6-thioxo-5,7-diazaspiro[3.4]oct-5-yl]-2-fluoro-N-methylbenzamide. In some embodiments, the softgel capsule shell comprises gelatin NF/EP, a 50:50 sorbitol/glycerin blend USP/EP, and purified water USP/EP. In some embodiments, a single unit dosage of the pharmaceutical composition comprises about 30 mg of 4-[7-(6-cyano-5-trifluoromethylpyridin-3-yl)-8-oxo-6-thioxo-5,7-diazaspiro[3.4]oct-5-yl]-2-fluoro-N-methylbenzamide.

In any of the methods of treatment embodiments described herein, the methods of treatment further comprises administering a gonadotropin-releasing hormone (GnRH) agonist or antagonist. In some embodiments, the GnRH agonist or antagonist is leuprolide, buserelin, nafarelin, histrelin, goserelin, or deslorelin.

In any of the aforementioned aspects the effective amount of 4-[7-(6-cyano-5-trifluoromethylpyridin-3-yl)-8-oxo-6-thioxo-5,7-diazaspiro[3.4]oct-5-yl]-2-fluoro-N-methylbenzamide is: (a) systemically administered to the male human; and/or (b) administered orally to the male human; and/or (c) intravenously administered to the male human; and/or (d) administered by injection to the male human.

In any of the aforementioned aspects, the effective amount of 4-[7-(6-cyano-5-trifluoromethylpyridin-3-yl)-8-oxo-6-thioxo-5,7-diazaspiro[3.4]oct-5-yl]-2-fluoro-N-methylbenzamide is administered (i) once a day; or (ii) multiple times over the span of one day. In some embodiments, the effective amount of 4-[7-(6-cyano-5-trifluoromethylpyridin-3-yl)-8-oxo-6-thioxo-5,7-diazaspiro[3.4]oct-5-yl]-2-fluoro-N-methylbenzamide is administered once a day, twice a day, three times a day or four times a day. In some embodiments, the effective amount of 4-[7-(6-cyano-5-trifluoromethylpyridin-3-yl)-8-oxo-6-thioxo-5,7-diazaspiro[3.4]oct-5-yl]-2-fluoro-N-methylbenzamide is administered every other day, twice a week, once a week, or every two weeks.

In any of the aforementioned aspects the effective amount of 4-[7-(6-cyano-5-trifluoromethylpyridin-3-yl)-8-oxo-6-thioxo-5,7-diazaspiro[3.4]oct-5-yl]-2-fluoro-N-methylbenzamide is administered continuously or intermittently. In some embodiments, the effective amount of 4-[7-(6-cyano-5-trifluoromethylpyridin-3-yl)-8-oxo-6-thioxo-5,7-diazaspiro[3.4]oct-5-yl]-2-fluoro-N-methylbenzamide is administered continuously. In some embodiments, the effective amount of 4-[7-(6-cyano-5-trifluoromethylpyridin-3-yl)-8-oxo-6-thioxo-5,7-diazaspiro[3.4]oct-5-yl]-2-fluoro-N-methylbenzamide is administered daily.

In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is orally administered.

In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the human on a continuous daily dosing schedule.

In some embodiments, described herein is a method of treating cancer in a mammal comprising administering to the mammal a therapeutically effective amount of 4-[7-(6-cyano-5-trifluoromethylpyridin-3-yl)-8-oxo-6-thioxo-5,7-diazaspiro[3.4]oct-5-yl]-2-fluoro-N-methylbenzamide. In some embodiments, the cancer is a hormone dependent cancer. In some embodiments, the hormone dependent cancer is an androgen receptor dependent cancer. In some embodiments, the cancer is advanced prostate cancer. In some embodiments, the cancer is hormone refractory prostate cancer. In some embodiments, the cancer is castration sensitive prostate cancer. In some embodiments, the cancer is castration resistant prostate cancer. In some embodiments, the cancer is high risk localized prostate cancer. In some embodiments, the cancer is androgen receptor positive breast cancer. In some embodiments, the method of treating cancer further comprises administering to the mammal at least one additional therapeutic agent. In some embodiments, the additional therapeutic agent is an anti-cancer agent. In some embodiments, the one or more additional therapeutically active agents other than 4-[7-(6-cyano-5-trifluoromethylpyridin-3-yl)-8-oxo-6- thioxo-5,7-diazaspiro[3.4]oct-5-yl]-2-fluoro-N-methylbenzamide is selected from: TORC inhibitors, PI3K inhibitors, CYP17 inhibitors, GNRH agonists or antagonists, osteoprotective agents, Syk inhibitors; RANKL inhibitors, MET inhibitors, VEGFR inhibitors, EGFR inhibitors, FGFR, MEK inhibitors, Src inhibitors, AKT inhibitors, RAF inhibitors, CDK4 inhibitors, CDK6 inhibitors, mTOR inhibitors; and antibodies (e.g., rituxan), corticosteroids, anti-emetic agents, analgesics, taxanes, tubulin inhibitors, anti-inflammatories, HSP90 inhibitors, histone deacetylase (HDAC) inhibitors or any other chemotherapeutic agent.

Articles of manufacture, which include packaging material, 4-[7-(6-cyano-5-trifluoromethylpyridin-3-yl)-8-oxo-6-thioxo-5,7-diazaspiro[3.4]oct-5-yl]-2-fluoro-N-methylbenzamide within the packaging material, and a label that indicates that the 4-[7-(6-cyano-5-trifluoromethylpyridin-3-yl)-8-oxo-6-thioxo-5,7-diazaspiro[3.4]oct-5-yl]-2-fluoro-N-methylbenzamide or composition thereof, or pharmaceutically acceptable salt, pharmaceutically active metabolite, is used for reducing, diminishing or eliminating the effects of androgen receptors, or for the treatment, prevention or amelioration of one or more symptoms of a disease or condition that would benefit from a reduction or elimination of androgen receptor activity, are provided. In some embodiments, such diseases or conditions include, but are not limited to, metastatic castration-resistant prostate cancer, non-metastatic castration-resistant prostate cancer, metastatic castration-sensitive prostate cancer, non-metastatic castration-sensitive prostate cancer, high-risk localized prostate cancer, breast cancer, androgen dependent hirsutism, androgenic alopecia, uterine fibroids, leiomyoma, endometrial carcinoma or endometriosis.

Other objects, features and advantages of the compound, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

DETAILED DESCRIPTION OF THE INVENTION

Androgen receptor (AR) is a member of the steroid and nuclear receptor superfamily. Among this large family of proteins, only five vertebrate steroid receptors are known and include the androgen receptor, estrogen receptor, progesterone receptor, glucocorticoid receptor, and mineralocorticoid receptor. AR is a soluble protein that functions as an intracellular transcriptional factor. AR function is regulated by the binding of androgens, which initiates sequential conformational changes of the receptor that affect receptor-protein interactions and receptor-DNA interactions.

AR is mainly expressed in androgen target tissues, such as the prostate, skeletal muscle, liver, and central nervous system (CNS), with the highest expression level observed in the prostate, adrenal gland, and epididymis. AR can be activated by the binding of endogenous androgens, including testosterone and 5α-dihydrotestosterone (5α-DHT).

The androgen receptor (AR), located on Xq11-12, is a 110 kD nuclear receptor that, upon activation by androgens, mediates transcription of target genes that modulate growth and differentiation of prostate epithelial cells. Similar to the other steroid receptors, unbound AR is mainly located in the cytoplasm and associated with a complex of heat shock proteins (HSPs) through interactions with the ligand-binding domain.

Upon agonist binding, AR goes through a series of conformational changes: the heat shock proteins dissociate from AR, and the transformed AR undergoes dimerization, phosphorylation, and translocation to the nucleus, which is mediated by the nuclear localization signal. Translocated receptor then binds to the androgen response element (ARE), which is characterized by the six-nucleotide half-site consensus sequence 5'-TGTTCT-3' spaced by three random nucleotides and is located in the promoter or enhancer region of AR gene targets. Recruitment of other transcription co-regulators (including co-activators and co-repressors) and transcriptional machinery further ensures the transactivation of AR-regulated gene expression. All of these processes are initiated by the ligand-induced conformational changes in the ligand-binding domain.

AR signaling is crucial for the development and maintenance of male reproductive organs including the prostate gland, as genetic males harboring loss of function AR mutations and mice engineered with AR defects do not develop prostates or prostate cancer. This dependence of prostate cells on AR signaling continues even upon neoplastic transformation. Androgen depletion (such as using GnRH agonists) continues to be the mainstay of prostate cancer treatment. However androgen depletion is usually effective for a limited duration and prostate cancer evolves to regain the ability to grow despite low levels of circulating androgens. Castration resistant prostate cancer (CRPC) is a lethal phenotype and almost all of patients will die from prostate cancer. Interestingly, while a small minority of CRPC does bypass the requirement for AR signaling, the vast majority of CRPC, though frequently termed "androgen independent prostate cancer" or "hormone refractory prostate cancer," retains its lineage dependence on AR signaling.

Prostate cancer is the second most common cause of cancer death in men in the US, and approximately one in every six American men will be diagnosed with the disease during his lifetime. Treatment aimed at eradicating the tumor is unsuccessful in 30% of men, who develop recurrent disease that is usually manifest first as a rise in plasma prostate-specific antigen (PSA) followed by spread to distant sites. Given that prostate cancer cells depend on androgen receptor (AR) for their proliferation and survival, these men are treated with agents that block production of testosterone (e.g. GnRH agonists), alone or in combination with anti-androgens (e.g. bicalutamide), which antagonize the effect of any residual testosterone on AR. The approach is effective as evidenced by a drop in PSA and regression of visible tumor (if present) in some patients; however, this is followed by regrowth as a castration resistant prostate cancer (CRPC) to which most patients eventually succumb. Recent studies on the molecular basis of CRPC have demonstrated that CRPC continues to depend on AR signaling and that a key mechanism of acquired resistance is an elevated level of AR protein (*Nat. Med*, 2004, 10, 33-39). AR targeting agents with activity in castration sensitive and castration resistant resistant prostate cancer have great promise in treating this lethal disease.

The course of prostate cancer from diagnosis to death is best categorized as a series of clinical states based on the extent of disease, hormonal status, and absence or presence of detectable metastases: localized disease, rising levels of prostate-specific antigen (PSA) after radiation therapy or surgery with no detectable metastases, and clinical metastases in the non-castrate or castrate state. Although surgery, radiation, or a combination of both can be curative for patients with localized disease, a significant proportion of these patients have recurrent disease as evidenced by a rising level of PSA, which can lead to the development of metastases, especially in the high risk group—a transition to the lethal phenotype of the disease.

Androgen depletion is the standard treatment with a generally predictable outcome: decline in PSA, a period of stability in which the tumor does not proliferate, followed by rising PSA and regrowth as castration-resistant disease. Molecular profiling studies of castration-resistance prostate cancers commonly show increased androgen receptor (AR) expression, which can occur through AR gene amplification or other mechanisms.

Anti-androgens are useful for the treatment of prostate cancer during its early stages. However, prostate cancer often advances to a 'hormone-refractory' state in which the disease progresses in the presence of continued androgen ablation or anti-androgen therapy. Instances of antiandrogen withdrawal syndrome have also been reported after prolonged treatment with anti-androgens. Antiandrogen withdrawal syndrome is commonly observed clinically and is defined in terms of the tumor regression or symptomatic relief observed upon cessation of antiandrogen therapy. AR mutations that result in receptor promiscuity and the ability of these anti-androgens to exhibit agonist activity might at least partially account for this phenomenon. For example, hydroxyflutamide and bicalutamide act as AR agonists in T877A and W741L/W741C AR mutants, respectively.

In the setting of prostate cancer cells that were rendered castration resistant via overexpression of AR, it has been demonstrated that certain anti-androgen compounds, such as bicalutamide, have a mixed antagonist/agonist profile (Science, 2009 May 8; 324(5928): 787-90). This agonist activity helps to explain a clinical observation, called the anti-androgen withdrawal syndrome, whereby about 30% of men who progress on AR antagonists experience a decrease in serum PSA when therapy is discontinued (*J Clin Oncol*, 1993. 11(8): p. 1566-72).

Prostate Cancer Stages

In the early stages of prostate cancer, the cancer is localized to the prostate. In these early stages, treatment typically involves either surgical removal of the prostate or radiation therapy to the prostate or observation only with no active intervention therapy in some patients. In the early stages where the prostate cancer is localized and requires intervention, surgery or radiation therapy are curative by eradicating the cancerous cells. About 30% of the time these procedures fail, and the prostate cancer continues to progress, as typically evidenced by a rising PSA level. Men whose prostate cancer has progressed following these early treatment strategies are said to have advanced or recurrent prostate cancer.

Because prostate cancer cells depend on the androgen receptor (AR) for their proliferation and survival, men with advanced prostate cancer are treated with agents that block the production of testosterone (eg, GnRH agonists), alone or in combination with anti-androgens (eg, bicalutamide), which antagonize the effect of any residual testosterone on AR. These treatments reduce serum testosterone to castrate levels, which generally slows disease progression for a period of time. The approach is effective as evidenced by a drop in PSA and the regression of visible tumors in some patients. Eventually, however, this is followed by regrowth referred to as castration-resistant prostate cancer (CRPC), to which most patients eventually succumb.

Castration-resistant prostate cancer (CRPC) is categorized as non-metastatic or metastatic, depending on whether or not the prostate cancer has metastasized to other parts of the body.

In some embodiments, prior to treatment with a second-generation anti-androgen (e.g. 4-[7-(6-cyano-5-trifluoromethylpyridin-3-yl)-8-oxo-6-thioxo-5,7-diazaspiro[3.4]oct-5-yl]-2-fluoro-N-methylbenzamide) men with non-metastatic CRPC are characterized as having the following:
1. Histologically or cytologically confirmed adenocarcinoma of the prostate, with high risk for development of metastases.
2. Castration-resistant prostate cancer demonstrated during continuous androgen deprivation therapy (ADT)/post orchiectomy. For example defined as 3 consecutive rises of PSA, 1 week apart, resulting in two 50% increases over the nadir, with the last PSA>2 ng/mL, with castrated levels of testosterone (<50 ng/dL [1.72 nmol/L]).
3. Absence of distant metastasis by bone scan, CT or MRI scans.

In some embodiments, prior to treatment with a second-generation anti-androgen (e.g. 4-[7-(6-cyano-5-trifluoromethylpyridin-3-yl)-8-oxo-6-thioxo-5,7-diazaspiro[3.4]oct-5-yl]-2-fluoro-N-methylbenzamide) men with metastatic CRPC are characterized as having the following:
1. Histologically or cytologically confirmed adenocarcinoma of the prostate, with progressive metastatic disease based on either PSA or radiographic evidence of progression on bone scan, CT or MRI scans.
2. Castration-resistant prostate cancer demonstrated during continuous androgen deprivation therapy (ADT)/post orchiectomy. For example defined as 3 consecutive rises of PSA, 1 week apart, resulting in two 50% increases over the nadir, with the last PSA>2 ng/mL, with castrated levels of testosterone (<50 ng/dL [1.72 nmol/L]).

In some embodiments, prior to treatment with a second-generation anti-androgen (e.g. 4-[7-(6-cyano-5-trifluoromethylpyridin-3-yl)-8-oxo-6-thioxo-5,7-diazaspiro[3.4]oct-5-yl]-2-fluoro-N-methylbenzamide) men with post-abiraterone acetate treated metastatic CRPC are characterized as having the following:
1. Histologically or cytologically confirmed adenocarcinoma of the prostate, with progressive metastatic disease based on either PSA or radiographic evidence of progression on bone, CT or MRI scan, following at least 6 months of treatment with abiraterone acetate
2. Castration-resistant prostate cancer demonstrated during continuous androgen deprivation therapy (ADT)/post orchiectomy. For example defined as 3 consecutive rises of PSA, 1 week apart, resulting in two 50% increases over the nadir, with the last PSA>2 ng/mL, with castrated levels of testosterone (<50 ng/dL [1.72 nmol/L]).

In some embodiments, prior to treatment with a second-generation anti-androgen (e.g. 4-[7-(6-cyano-5-trifluoromethylpyridin-3-yl)-8-oxo-6-thioxo-5,7-diazaspiro[3.4]oct-5-yl]-2-fluoro-N-methylbenzamide) men with metastatic castration-sensitive prostate cancer are characterized as having the following:
1. Histologically or cytologically confirmed adenocarcinoma of the prostate, with metastatic disease based on radiographic evidence on bone scan, CT or MRI scans.
2. Prostate cancer which is still responsive to androgen deprivation therapy (ADT).

In some embodiments, prior to treatment with a second-generation anti-androgen (e.g. 4-[7-(6-cyano-5-trifluoromethylpyridin-3-yl)-8-oxo-6-thioxo-5,7-diazaspiro[3.4]oct-5-yl]-2-fluoro-N-methylbenzamide) men with non-metastatic castration-sensitive prostate cancer are characterized as having the following:

1. Histologically or cytologically confirmed adenocarcinoma of the prostate, with high risk for development of metastases.
2. Absence of distant metastasis by bone scan, CT or MRI scans.
3. Prostate cancer which is still responsive to androgen deprivation therapy (ADT).

In some embodiments, prior to treatment with a second-generation anti-androgen (e.g. 4-[7-(6-cyano-5-trifluoromethylpyridin-3-yl)-8-oxo-6-thioxo-5,7-diazaspiro[3.4]oct-5-yl]-2-fluoro-N-methylbenzamide) men with high-risk localized prostate cancer are characterized as having the following:
1. Absence of distant metastasis by bone scan, CT or MRI scans.
2. Local-regional prostate cancer which is at high risk for disease recurrence after local treatment with surgery or radiation therapy.

Anti-Androgens

As used herein, the term "anti-androgen" refers to a group of hormone receptor antagonist compounds that are capable of preventing or inhibiting the biologic effects of androgens on normally responsive tissues in the body. In some embodiments, an anti-androgen is a small molecule. In some embodiments, an anti-androgen is an AR antagonist. In some embodiments, an anti-androgen is an AR full antagonist. In some embodiments, an anti-androgen is a first-generation anti-androgen. In some embodiments, an anti-androgen is a second-generation anti-androgen.

As used herein, the term "AR antagonist" or "AR inhibitor" are used interchangeably herein and refer to an agent that inhibits or reduces at least one activity of an AR polypeptide. Exemplary AR activities include, but are not limited to, co-activator binding, DNA binding, ligand binding, or nuclear translocation.

As used herein, a "full antagonist" refers to an antagonist which, at an effective concentration, essentially completely inhibits an activity of an AR polypeptide. As used herein, a "partial antagonist" refers an antagonist that is capable of partially inhibiting an activity of an AR polypeptide, but that, even at a highest concentration is not a full antagonist. By 'essentially completely' is meant at least about 80%, at least about 90%, at least about 95%, at least about 96%, at least about 97%, at least about 98% at least about 99%, or greater inhibition of the activity of an AR polypeptide.

As used herein, the term "first-generation anti-androgen" refers to an agent that exhibits antagonist activity against a wild-type AR polypeptide. However, first-generation anti-androgens differ from second-generation anti-androgens in that first-generation anti-androgens can potentially act as agonists in castration resistant prostate cancers (CRPC). Exemplary first-generation anti-androgens include, but are not limited to, flutamide, nilutamide and bicalutamide.

As used herein, the term "second-generation anti-androgen" refers to an agent that exhibits full antagonist activity against a wild-type AR polypeptide. Second-generation anti-androgens differ from first-generation anti-androgens in that second-generation anti-androgens act as full antagonists in cells expressing elevated levels of AR, such as for example, in castration resistant prostate cancers (CRPC). Exemplary second-generation anti-androgens include 4-[7-(6-cyano-5-trifluoromethylpyridin-3-yl)-8-oxo-6-thioxo-5,7-diazaspiro[3.4]oct-5-yl]-2-fluoro-N-methylbenzamide (also known as ARN-509; CAS No. 956104-40-8); 4-(3-(4-cyano-3-(trifluoromethyl)phenyl)-5,5-dimethyl-4-oxo-2-thioxoimidazolidin-1-yl)-2-fluoro-N-methylbenzamide (also known as MDV3100 or enzalutamide; CAS No: 915087-33-1) and RD162 (CAS No. 915087-27-3). In some embodiments, a second-generation anti-androgen binds to an AR polypeptide at or near the ligand binding site of the AR polypeptide.

In some embodiments, an anti-androgen contemplated in the methods described herein inhibits AR nuclear translocation, DNA binding to androgen response elements, and coactivator recruitment. In some embodiments, an anti-androgen contemplated in the methods described herein exhibits no agonist activity in AR-overexpressing prostate cancer cells.

4-[7-(6-Cyano-5-trifluoromethylpyridin-3-yl)-8-oxo-6-thioxo-5,7-diazaspiro[3.4]oct-5-yl]-2-fluoro-N-methylbenzamide (I) is a second-generation anti-androgen that binds directly to the ligand-binding domain of AR, impairing nuclear translocation, AR binding to DNA and AR target gene modulation, thereby inhibiting tumor growth and promoting apoptosis. 4-[7-(6-Cyano-5-trifluoromethylpyridin-3-yl)-8-oxo-6-thioxo-5,7-diazaspiro[3.4]oct-5-yl]-2-fluoro-N-methylbenzamide binds AR with greater affinity than bicalutamide, and induces partial or complete tumor regression in non-castrate hormone-sensitive and bicalutamide-resistant human prostate cancer xenograft models (Clegg et al. Cancer Res Mar. 15, 2012 72; 1494). 4-[7-(6-Cyano-5-trifluoromethylpyridin-3-yl)-8-oxo-6-thioxo-5,7-diazaspiro[3.4]oct-5-yl]-2-fluoro-N-methylbenzamide lacks the partial agonist activity seen with bicalutamide in the context of AR overexpression.

Disclosed herein is the use of 4-[7-(6-cyano-5-trifluoromethylpyridin-3-yl)-8-oxo-6-thioxo-5,7-diazaspiro[3.4]oct-5-yl]-2-fluoro-N-methylbenzamide in the treatment of metastatic castration-resistant prostate cancer in a human. In some embodiments, the treatment of metastatic castration-resistant prostate cancer in the human comprises at least one additional therapeutic agent in addition to 4-[7-(6-cyano-5-trifluoromethylpyridin-3-yl)-8-oxo-6-thioxo-5,7-diazaspiro[3.4]oct-5-yl]-2-fluoro-N-methylbenzamide (i.e. combination therapy).

Disclosed herein is the use of 4-[7-(6-cyano-5-trifluoromethylpyridin-3-yl)-8-oxo-6-thioxo-5,7-diazaspiro[3.4]oct-5-yl]-2-fluoro-N-methylbenzamide in the treatment of chemotherapy naïve metastatic castration-resistant prostate cancer in a human. In some embodiments, the treatment of chemotherapy naïve metastatic castration-resistant prostate cancer in the human comprises at least one additional therapeutic agent in addition to 4-[7-(6-cyano-5-trifluoromethylpyridin-3-yl)-8-oxo-6-thioxo-5,7-diazaspiro[3.4]oct-5-yl]-2-fluoro-N-methylbenzamide (i.e. combination therapy).

Disclosed herein is the use of 4-[7-(6-cyano-5-trifluoromethylpyridin-3-yl)-8-oxo-6-thioxo-5,7-diazaspiro[3.4]oct-5-yl]-2-fluoro-N-methylbenzamide in the treatment of post-abiraterone acetate treated metastatic castration-resistant prostate cancer in a human. In some embodiments, the treatment of post-abiraterone acetate treated metastatic castration-resistant prostate cancer in the human comprises at least one additional therapeutic agent in addition to 4-[7-(6-cyano-5-trifluoromethylpyridin-3-yl)-8-oxo-6-thioxo-5,7-diazaspiro[3.4]oct-5-yl]-2-fluoro-N-methylbenzamide (i.e. combination therapy).

Disclosed herein is the use of 4-[7-(6-cyano-5-trifluoromethylpyridin-3-yl)-8-oxo-6-thioxo-5,7-diazaspiro[3.4]oct-5-yl]-2-fluoro-N-methylbenzamide in the treatment of castration-sensitive prostate cancer in a human. In some embodiments, the treatment of castration-sensitive prostate cancer in the human comprises at least one additional therapeutic agent in addition to 4-[7-(6-cyano-5-trifluoromethylpyridin-3-yl)-8-oxo-6-thioxo-5,7-diazaspiro[3.4]oct-5-yl]-2-fluoro-N-methylbenzamide (i.e. combination therapy).

Disclosed herein is the use of 4-[7-(6-cyano-5-trifluoromethylpyridin-3-yl)-8-oxo-6-thioxo-5,7-diazaspiro[3.4]oct-5- yl]-2-fluoro-N-methylbenzamide in the treatment of castration-resistant prostate cancer in a human. In some embodiments, the treatment of castration-resistant prostate cancer in the human comprises at least one additional therapeutic agent in addition to 4-[7-(6-cyano-5-trifluoromethylpyridin-3-yl)-8-oxo-6-thioxo-5,7-diazaspiro[3.4]oct-5-yl]-2-fluoro-N-methylbenzamide (i.e. combination therapy).

Disclosed herein is the use of 4-[7-(6-cyano-5-trifluoromethylpyridin-3-yl)-8-oxo-6-thioxo-5,7-diazaspiro[3.4]oct-5-yl]-2-fluoro-N-methylbenzamide in the treatment of high-risk localized prostate cancer in a human. In some embodiments, the treatment of high-risk localized prostate cancer in the human comprises at least one additional therapeutic agent in addition to 4-[7-(6-cyano-5-trifluoromethylpyridin-3-yl)-8-oxo-6-thioxo-5,7-diazaspiro[3.4]oct-5-yl]-2-fluoro-N-methylbenzamide (i.e. combination therapy).

Disclosed herein is the use of 4-[7-(6-cyano-5-trifluoromethylpyridin-3-yl)-8-oxo-6-thioxo-5,7-diazaspiro[3.4]oct-5-yl]-2-fluoro-N-methylbenzamide in the treatment of non-metastatic castration-resistant prostate cancer in a human. In some embodiments, the treatment of non-metastatic castration-resistant prostate cancer in the human comprises at least one additional therapeutic agent in addition to 4-[7-(6-cyano-5-trifluoromethylpyridin-3-yl)-8-oxo-6-thioxo-5,7-diazaspiro[3.4]oct-5-yl]-2-fluoro-N-methylbenzamide (i.e. combination therapy).

Disclosed herein is the use of 4-[7-(6-cyano-5-trifluoromethylpyridin-3-yl)-8-oxo-6-thioxo-5,7-diazaspiro[3.4]oct-5-yl]-2-fluoro-N-methylbenzamide in the treatment of metastatic castration-sensitive prostate cancer in a human. In some embodiments, the treatment of metastatic castration-sensitive prostate cancer in the human comprises at least one additional therapeutic agent in addition to 4-[7-(6-cyano-5-trifluoromethylpyridin-3-yl)-8-oxo-6-thioxo-5,7-diazaspiro[3.4]oct-5-yl]-2-fluoro-N-methylbenzamide (i.e. combination therapy).

Disclosed herein is the use of 4-[7-(6-cyano-5-trifluoromethylpyridin-3-yl)-8-oxo-6-thioxo-5,7-diazaspiro[3.4]oct-5-yl]-2-fluoro-N-methylbenzamide in the treatment of non-metastatic castration-sensitive prostate cancer in a human. In some embodiments, the treatment of non-metastatic castration-sensitive prostate cancer in the human comprises at least one additional therapeutic agent in addition to 4-[7-(6-cyano-5-trifluoromethylpyridin-3-yl)-8-oxo-6-thioxo-5,7-diazaspiro[3.4]oct-5-yl]-2-fluoro-N-methylbenzamide (i.e. combination therapy).

Disclosed herein is the use of 4-[7-(6-cyano-5-trifluoromethylpyridin-3-yl)-8-oxo-6-thioxo-5,7-diazaspiro[3.4]oct-5-yl]-2-fluoro-N-methylbenzamide in the treatment of breast cancer in a human. In some embodiments, the treatment of breast cancer in the human comprises at least one additional therapeutic agent in addition to 4-[7-(6-cyano-5-trifluoromethylpyridin-3-yl)-8-oxo-6-thioxo-5,7-diazaspiro[3.4]oct-5-yl]-2-fluoro-N-methylbenzamide (i.e. combination therapy).

Disclosed herein is the use of 4-[7-(6-cyano-5-trifluoromethylpyridin-3-yl)-8-oxo-6-thioxo-5,7-diazaspiro[3.4]oct-5-yl]-2-fluoro-N-methylbenzamide in the treatment of androgen dependent hirsutism in a human. In some embodiments, the treatment of androgen dependent hirsutism in the human comprises at least one additional therapeutic agent in addition to 4-[7-(6-cyano-5-trifluoromethylpyridin-3-yl)-8-oxo-6-thioxo-5,7-diazaspiro[3.4]oct-5-yl]-2-fluoro-N-methylbenzamide (i.e. combination therapy).

Disclosed herein is the use of 4-[7-(6-cyano-5-trifluoromethylpyridin-3-yl)-8-oxo-6-thioxo-5,7-diazaspiro[3.4]oct-5-yl]-2-fluoro-N-methylbenzamide in the treatment of androgenic alopecia in a human. In some embodiments, the treatment of androgenic alopecia in the human comprises at least one additional therapeutic agent in addition to 4-[7-(6-cyano-5-trifluoromethylpyridin-3-yl)-8-oxo-6-thioxo-5,7-diazaspiro[3.4]oct-5-yl]-2-fluoro-N-methylbenzamide (i.e. combination therapy).

Disclosed herein is the use of 4-[7-(6-cyano-5-trifluoromethylpyridin-3-yl)-8-oxo-6-thioxo-5,7-diazaspiro[3.4]oct-5-yl]-2-fluoro-N-methylbenzamide in the treatment of uterine fibroids in a human. In some embodiments, the treatment of uterine fibroids in the human comprises at least one additional therapeutic agent in addition to 4-[7-(6-cyano-5-trifluoromethylpyridin-3-yl)-8-oxo-6-thioxo-5,7-diazaspiro[3.4]oct-5-yl]-2-fluoro-N-methylbenzamide (i.e. combination therapy).

Disclosed herein is the use of 4-[7-(6-cyano-5-trifluoromethylpyridin-3-yl)-8-oxo-6-thioxo-5,7-diazaspiro[3.4]oct-5-yl]-2-fluoro-N-methylbenzamide in the treatment of leiomyoma in a human. In some embodiments, the treatment of leiomyoma in the human comprises at least one additional therapeutic agent in addition to 4-[7-(6-cyano-5-trifluoromethylpyridin-3-yl)-8-oxo-6-thioxo-5,7-diazaspiro[3.4]oct-5-yl]-2-fluoro-N-methylbenzamide (i.e. combination therapy).

Disclosed herein is the use of 4-[7-(6-cyano-5-trifluoromethylpyridin-3-yl)-8-oxo-6-thioxo-5,7-diazaspiro[3.4]oct-5-yl]-2-fluoro-N-methylbenzamide in the treatment of endometrial carcinoma in a human. In some embodiments, the treatment of endometrial carcinoma in the human comprises at least one additional therapeutic agent in addition to 4-[7-(6-cyano-5-trifluoromethylpyridin-3-yl)-8-oxo-6-thioxo-5,7-diazaspiro[3.4]oct-5-yl]-2-fluoro-N-methylbenzamide (i.e. combination therapy).

Disclosed herein is the use of 4-[7-(6-cyano-5-trifluoromethylpyridin-3-yl)-8-oxo-6-thioxo-5,7-diazaspiro[3.4]oct-5-yl]-2-fluoro-N-methylbenzamide in the treatment of endometriosis in a human. In some embodiments, the treatment of endometriosis in the human comprises at least one additional therapeutic agent in addition to 4-[7-(6-cyano-5-trifluoromethylpyridin-3-yl)-8-oxo-6-thioxo-5,7-diazaspiro[3.4]oct-5-yl]-2-fluoro-N-methylbenzamide (i.e. combination therapy).

In a Phase II clinical trial of male humans with high risk non-metastatic CRPC, treatment-naïve metastatic CRPC and metastatic CRPC that progressed after prior treatment with abiraterone acetate (Zytiga®), oral administration of 240 mg of 4-[7-(6-cyano-5-trifluoromethylpyridin-3-yl)-8-oxo-6-thioxo-5,7-diazaspiro[3.4]oct-5-yl]-2-fluoro-N-methylbenzamide on a continuous daily dosing schedule was very well tolerated and resulted in robust and durable PSA responses, as well as evidence of objective responses. A total of 25 patients with chemotherapy and abiraterone acetate-naïve metastatic CRPC who had progressed on standard androgen deprivation therapy (treatment-naïve (TN) cohort) and 21 patients who progressed after treatment with abiraterone acetate acetate (PA cohort) were orally administered 240 mg of 4-[7-(6-cyano-5-trifluoromethylpyridin-3-yl)-8-oxo-6-thioxo-5,7-diazaspiro[3.4]oct-5-yl]-2-fluoro-N-methylbenzamide on a continuous daily dosing schedule. The primary objective was to assess antitumor activity and PSA kinetics as defined by the Prostate Cancer Clinical Trials Working Group (PCWG2) criteria. Preliminary results demonstrated 12-week PSA declines of ≥50% or more from baseline in 88% and 29% of the TN and PA cohorts, respectively. The median time to PSA progression was not reached for the TN cohort during the preliminary 12-week period, and was 16 weeks in the PA cohort. In addition, the objective response rate (by RECIST) was 63% in the TN patients presenting with measurable disease at baseline, further confirming the antitumor activity of 4-[7-(6-cyano-5-trifluoromethylpyridin-3-yl)-8-oxo-6-thioxo-5,7-diazaspiro[3.4]oct-5-yl]-2-fluoro-N-methylbenzamide.

A total of 47 patients with non-metastatic CRPC were orally administered 240 mg of 4-[7-(6-cyano-5-trifluoromethylpyridin-3-yl)-8-oxo-6-thioxo-5,7-diazaspiro[3.4]oct-5-yl]-2-fluoro-N-methylbenzamide on a continuous daily dosing schedule. At 12 weeks of treatment, 91% of the patients had a ≥50% decline in PSA as compared to baseline. At 24 weeks, the percentage of patients who had ≥50% decline in PSA remained at 91% and the percentage of patients who had ≥90% decline in PSA was 55%, confirming the durability of response to 4-[7-(6-cyano-5-trifluoromethylpyridin-3-yl)-8-oxo-6-thioxo-5,7-diazaspiro[3.4]oct-5-yl]-2-fluoro-N-methylbenzamide. The median time to PSA progression was not reached in this observed time period.

4-[7-(6-Cyano-5-trifluoromethylpyridin-3-yl)-8-oxo-6-thioxo-5,7-diazaspiro[3.4]oct-5-yl]-2-fluoro-N-methylbenzamide is suited as monotherapy and as combination therapy for advanced prostate cancer, as well as other diseases or conditions described herein.

CERTAIN TERMINOLOGY

The term "cancer" as used herein refers to an abnormal growth of cells which tend to proliferate in an uncontrolled way and, in some cases, to metastasize (spread).

The term "prostate cancer" as used herein refers to histologically or cytologically confirmed adenocarcinoma of the prostate.

The term "androgen-deprivation therapy (ADT)" refers to the reduction of androgen levels in a prostate cancer patient to castrated levels of testosterone (<50 ng/dL). Such treatments can include orchiectomy or the use of gonadotropin-releasing hormone agonists or antagonists.

The term "locally advanced prostate cancer" refers to prostate cancer where all actively cancerous cells appear to be confined to the prostate and the associated organs or neighbor organs (e.g. seminal vesicle, bladder neck and rectal wall).

The term "high-risk localized prostate cancer" refers to locally advanced prostate cancer that has a probability of developing metastases or recurrent disease after primary therapy with curative intent. In some embodiments, high risk for development of metastases is defined as prostate specific antigen doubling time (PSADT)≤20 months, ≤19 months, ≤18 months, ≤17 months, ≤16 months, ≤15 months, ≤14 months, ≤13 months, ≤12 months, or ≤11 months, ≤10 months, ≤9 months, ≤8 months, ≤7 months, ≤6 months, ≤5 months, ≤4 months, ≤3 months, ≤2 months, or ≤1 month. In some embodiments, high risk for development of metastases is defined as prostate specific antigen doubling time (PSADT) ≤10 months. In some embodiments, high risk for development of metastases is defined as having a high Gleason score or bulky tumor.

The term "castration-sensitive prostate cancer" refers to cancer that is responsive to androgen-deprivation therapy (ADT) either as localized disease, biochemical relapse or in the metastatic setting.

The term "metastatic castration-sensitive prostate cancer" refers to cancer that has spread (metastasized) to the bone, lymph nodes or other parts of the body in a male, and that is responsive to androgen-deprivation therapy (ADT).

The term "non-metastatic castration-sensitive prostate cancer" refers to cancer that has not spread (metastasized) in a male, and that is responsive to androgen-deprivation therapy (ADT). In some embodiments, non-metastatic castration-sensitive prostate cancer is assessed with bone scan and computed tomography (CT) or magnetic resonance imaging (MRI) scans.

The term "CRPC" as used herein refers to castration-resistant prostate cancer. CRPC is prostate cancer that continues to grow despite the suppression of male hormones that fuel the growth of prostate cancer cells.

The term "metastatic castration-resistant prostate cancer" refers to castration-resistant prostate cancer that has metastasized to other parts of the human body.

The term "NM-CRPC" as used herein refers to non-metastatic castration-resistant prostate cancer. In some embodiments, NM-CRPC is assessed with bone scan and computed tomography (CT) or magnetic resonance imaging (MRI) scans.

The term "chemotherapy naïve metastatic castration-resistant prostate cancer" refers to metastatic castration-resistant prostate cancer that has not been previously treated with a chemotherapeutic agent.

The term "post-abiraterone acetate treated metastatic castration-resistant prostate cancer" refers to metastatic castration-resistant prostate cancer that has already been treated with abiraterone acetate.

The term "high risk NM-CRPC" as used herein refers to probability of a man with NM-CRPC developing metastases. In some embodiments, high risk for development of metastases is defined as prostate specific antigen doubling time (PSADT)≤20 months, ≤19 months, ≤18 months, ≤17 months, ≤16 months, ≤15 months, ≤14 months, ≤13 months, ≤12 months, or ≤11 months, ≤10 months, ≤9 months, ≤8 months, ≤7 months, ≤6 months, ≤5 months, ≤4 months, ≤3 months, ≤2 months, or ≤1 month. In some embodiments, high risk for development of metastases is defined as prostate specific antigen doubling time (PSADT)≤10 months. In some embodiments, high risk for development of metastases is defined as having local-regional recurrence (e.g. primary tumor bed, bladder neck, anastomotic area, pelvic lymph nodes).

The terms "co-administration" or the like, as used herein, are meant to encompass administration of the selected therapeutic agents to a single patient, and are intended to include treatment regimens in which the agents are administered by the same or different route of administration or at the same or different time.

The term "pharmaceutical combination" as used herein, means a product that results from the mixing or combining of more than one active ingredient and includes both fixed and non-fixed combinations of the active ingredients. The term "fixed combination" means that the active ingredients, e.g. 4-[7-(6-cyano-5-trifluoromethylpyridin-3-yl)-8-oxo-6-thioxo-5,7-diazaspiro[3.4]oct-5-yl]-2-fluoro-N-methylbenzamide and a co-agent, are both administered to a patient simultaneously in the form of a single entity or dosage. The term "non-fixed combination" means that the active ingredients, e.g. 4-[7-(6-cyano-5-trifluoromethylpyridin-3-yl)-8-oxo-6-thioxo-5,7-diazaspiro[3.4]oct-5-yl]-2-fluoro-N-methylbenzamide and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The terms "effective amount" or "therapeutically effective amount," as used herein, refer to a sufficient amount of an anti-androgen being administered which will relieve to some extent one or more of the symptoms of the disease or condition being treated. The result can be reduction and/or alleviation of the signs, symptoms, or causes of a disease, or any other desired alteration of a biological system. For example, an effective amount of an anti-androgen is the amount of the anti-androgen that after administration for 3 months to a male human with prostate cancer provides a PSA50 or PSA90 or demonstrates a robust (such as ≥90%) AR blockade (e.g. by FDHT-PET). In some embodiments, an effective amount of an anti-androgen is the amount of the anti-androgen that after administration for 6 months to a male human with prostate cancer provides a PSA50 or PSA90. In some embodiments, an effective amount of an anti-androgen is the amount of the anti-androgen that after administration for 6 months to a male human with prostate cancer delays progression of the prostate cancer. In some embodiments, an effective amount of an anti-androgen is the amount of the anti-androgen that after administration for 6 months to a male human with prostate cancer increases the survival rate of the male human. In some embodiments, the anti-androgen is administered on a continuous daily dosing schedule. An appropriate "effective" amount in any individual case may be determined using techniques, such as a dose escalation study.

The term "FDHT-PET" refers to 18F-16β-fluoro-5α-dihydrotestosterone Positron Emission Tomography and is a technique that uses a tracer based on dihydrotestosterone, and allows for a visual assessment of ligand binding to the androgen receptor in a patient. It may be used to evaluate pharmacodynamics of an androgen receptor directed therapy The term "continuous daily dosing schedule" refers to the administration of a particular therapeutic agent without any drug holidays from the particular therapeutic agent. In some embodiments, a continuous daily dosing schedule of a particular therapeutic agent comprises administration of a particular therapeutic agent everyday at roughly the same time each day.

The terms "treat," "treating" or "treatment," as used herein, include alleviating, abating or ameliorating at least one symptom of a disease disease or condition, preventing additional symptoms, inhibiting the disease or condition, e.g., arresting the development of the disease or condition, relieving the disease or condition, causing regression of the disease or condition, delaying progression of condition, relieving a condition caused by the disease or condition, or stopping the symptoms of the disease or condition either prophylactically and/or therapeutically. In some embodiments, in the context of administering an anti-androgen to a male human with prostate cancer, treating comprises any one, or a combination, of the following: providing a PSA50 or PSA90 in men with prostate cancer as compared to placebo at 3 months; providing a PSA50 or PSA90 in men with prostate cancer as compared to placebo at 6 months; demonstrating superiority in the metastasis-free survival (MFS) of men with prostate cancer as compared to placebo (i.e. not administering a second-generation anti-androgen); increasing the overall survival (OS) of men with prostate cancer as compared to placebo; increasing the time to metastasis (TTM) in men with prostate cancer as compared to placebo; increasing the progression-free survival (PFS) in men with prostate cancer as compared to placebo; increasing the time to PSA progression (TTPP) in men with prostate cancer as compared to placebo; increasing the health-related quality of life and prostate cancer-specific symptoms in men with prostate cancer as compared to placebo. In some embodiments, the prostate cancer is metastatic castration-resistant prostate cancer, non-metastatic castration-resistant prostate cancer, metastatic castration-sensitive prostate cancer, non-metastatic castration-sensitive prostate cancer or high-risk localized prostate cancer.

The term "metastasis-free survival" or "MFS" refers to the percentage of subjects in a study who have survived without cancer spread for a defined period of time or death. MFS is usually reported as time from the beginning of enrollment, randomization or treatment in the study. MFS is reported for an individual or a study population. In the context of treatment of CRPC with an anti-androgen, an increase in the metastasis-free survival is the additional time that is observed without cancer having spread or death, whichever occurs first, as compared to treatment with placebo. In some embodiments, the increase in the metastasis-free survival is about 1 month, about 2 months, about 3 months, about 4 months, about 5 months, about 6 months, about 7 months, about 8 months, about 10 months, about 11 months, about 12 months, about 13 months, about 14 months, about 15 months, about 16 months, about 17 months, about 18 months, about 19 months, about 20 months, or greater than 20 months.

The term "placebo" as used herein means administration of a pharmaceutical composition that does not include a second-generation anti-androgen. In the context of treatment of CRPC, men that are administered an anti-androgen or placebo will need to continue to maintain castrated levels of testosterone by either coadministration of a GnRH agonist/antagonist or orchiectomy.

The term "Survival benefit" as used herein means an increase in survival of the patient from time of randomization on the trial of administered drug to death. In some embodiments, the survival benefit is about 1, about 2, about 3, about 4, about 5, about 6, about 7, about 8, about 9, about 10, about 15, about 20, about 25, about 30, about 35, about 40, about 45, about 50, about 55, about 60, about 80, about 100 months or greater than 100 months.

The term "delay in symptoms related to disease progression" as used herein means an increase in time in the development of symptoms such as pain, urinary obstruction and quality of life considerations from the time of randomization on the trial of administered drug.

The term 'randomization' as it refers to a clinical trial refers to the time when the patient is confirmed eligible for the clinical trial and gets assigned to a treatment arm.

The terms "kit" and "article of manufacture" are used as synonyms.

The term "subject" and "patient" and "human" are used interchangeably.

Routes of Administration and Pharmaceutical Compositions

Therapuetic agents described herein are administered in any suitable manner or suitable formulation. Suitable routes of administration of the therapeutic agents include, but are not limited to, oral and parenteral (e.g., intravenous, subcutaneous, intramuscular). All formulations are in dosages suitable for administration to a human. A summary of pharmaceutical compositions can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

A therapeutically effective amount of the therapeutic agents that are administered can vary widely depending on the severity of the disease, the age and relative health of the subject, the potency of the therapeutic agent used and other factors.

The term "acceptable" with respect to a formulation, composition or ingredient, as used herein, means having no persistent detrimental effect on the general health of the male human being treated.

As described herein, 4-[7-(6-cyano-5-trifluoromethylpyridin-3-yl)-8-oxo-6-thioxo-5,7-diazaspiro[3.4]oct-5-yl]-2-fluoro-N-methylbenzamide is orally administered to a human. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is orally administered to a human in the form of a capsule. In some embodiments, the capsule is a softgel capsule. The pharmaceutical compositions described herein allow for systemic administration 4-[7-(6-cyano-5-trifluoromethylpyridin-3-yl)-8-oxo-6-thioxo-5,7-diazaspiro[3.4]oct-5-yl]-2-fluoro-N-methylbenzamide.

Softgel (also called softgelatin or soft elastic) capsules consist of one-piece hermetically-sealed soft shells. In some embodiments, softgelatin capsules are prepared by adding a plasticizer, such as glycerin or polyhydric alcohol (e.g., sorbitol), to gelatin. The plasticizer makes gelatin elastic. Softgelatin capsules come in various shapes such as spherical, elliptical, and oblong. They can contain non-aqueous liquids or suspensions.

In some embodiments, a softgel capsule comprises component(s) from Component #1 and Component #2:

Component #1: Softgel Capsule Shell—Examples include, but are not limited to, gelatin, starch, and carrageenan.

Component #2: Softgel Capsule Plasticizer—Examples include, but are not limited to, sorbitol, glycerin, xylose, maltitol, and polyethylene glycol (PEG).

In some embodiments, the softgel capsule shell comprises gelatin NF/EP, a 50:50 sorbitol/glycerin blend USP/EP, and purified water USP/EP.

In some embodiments, the outer shell comprises optional ingredients such as color additives or flavor additives.

There are three types of inner fill materials for softgel capsules: neat substance, solution fill and suspension fill.

Neat substance is suited for oily liquids.

Solution fill comprises an active dissolved in a carrier. Carriers include, but are not limited to, oils (such as soybean oil and Miglyol 812 (neutral oil, triglycerides of medium chain fatty acids)), polyethylene glycols (e.g. PEG 400-600), any other solvent which doesn't degrade or solubilize the gelatin shell (dimethyl isosorbide, surfactants, diethylene glycol monoethly ether). Optional ingredients include, but are not limited to, water or alcohol (up to 10% w/w, if needed for solubility), glycerin (1 to 4% w/w to retard the migration of the glycerin out of the shell into the fill), polyvinylpyrrolidone (up to 10% w/w used in combination with PEG, can increase drug solubility, and also improve stability by inhibiting drug recrystallization).

Suspension Fill comprises an active dispersed in a carrier. Carriers include, but are not limited to, oily mixtures, polyethylene glycols, and glycerides. Oily mixtures include, but are not limited to, traditional oily mixtures such as soybean oil with beeswax (4-10% w/w) and lecithin (2-4% w/w); gelified oil (e.g. GELOIL™ SC gelified oil), a ready to use system composed of soybean oil, a suspending agent, and a wetting agent. Polyethylene glycol includes, but is not limited to, PEG 800-1000 for semi-solid fills, PEG 10,000-100,000 for solid fills, or mixtures thereof. Glycerides include, but are not limited to, glycerides of long chain fatty acids. Optional Ingredients include, but are not limited to, surfactant (e.g. sorbitan derivatives such as polysorbate 80 or lecithin).

A pharmaceutical composition of 4-[7-(6-cyano-5-trifluoromethylpyridin-3-yl)-8-oxo-6-thioxo-5,7-diazaspiro[3.4]oct-5-yl]-2-fluoro-N-methylbenzamide refers to a mixture of 4-[7-(6-cyano-5-trifluoromethylpyridin-3-yl)-8-oxo-6-thioxo-5,7-diazaspiro[3.4]oct-5-yl]-2-fluoro-N-methylbenzamide with other chemical components (i.e. pharmaceutically acceptable inactive ingredients). In some embodiments, a softgel capsule pharmaceutical composition of 4-[7-(6-cyano-5-trifluoromethylpyridin-3-yl)-8-oxo-6-thioxo-5,7-diazaspiro[3.4]oct-5-yl]-2-fluoro-N-methylbenzamide includes at least one of the following excipients: a. gelatin; b. softener (plasticizer) (e.g. sorbitol, xylose, maltitol, glycerin, PEG, water); c. preservatives (e.g. methyl paraben, propyl paraben, butylated hydroxyaniline, EDTA, sodium benzoate); d. dyes, pigments (e.g. titanium oxide, ferric oxide); e. polar Solvent(s) (e.g. glycerin, PEG, PEG 400, PEG 3350, ethanol, PPG, water); f. nonpolar solvent(s) (e.g. beeswax, coconut oil, triglycerin, corn oil, mineral oil, soybean oil, D,L-α-tocopherol); g. pH-adjusting additive; h. flavor and fragrance; i. anticaking agent (e.g. Silicone dioxide); j. humectant (e.g. polyol).

In one aspect, described herein is a pharmaceutical composition comprising a nonaqueous, lipid-based solution of 4-[7-(6-cyano-5-trifluoromethylpyridin-3-yl)-8-oxo-6-thioxo-5,7-diazaspiro[3.4]oct-5-yl]-2-fluoro-N-methylbenzamide in a softgel capsule.

In some embodiments, the nonaqueous, lipid-based solution of 4-[7-(6-cyano-5-trifluoromethylpyridin-3-yl)-8-oxo-6-thioxo-5,7-diazaspiro[3.4]oct-5-yl]-2-fluoro-N-methylbenzamide comprises: 4-[7-(6-cyano-5-trifluoromethylpyridin-3-yl)-8-oxo-6-thioxo-5,7-diazaspiro[3.4]oct-5-yl]-2-fluoro-N-methylbenzamide, vitamin E d-α-tocopheryl polyethylene glycol 1000 succinate NF (Vitamin E TPGS), polyethylene glycol 400 NF/EP (PEG 400), glycerol monocaprylocaprate EP (Capmul MCM) and caprylocaproyl macroglycerides EP/NF (Acconon MC8-2).

In some embodiments, the nonaqueous, lipid-based solution of 4-[7-(6-cyano-5-trifluoromethylpyridin-3-yl)-8-oxo-6-thioxo-5,7-diazaspiro[3.4]oct-5-yl]-2-fluoro-N-methylbenzamide comprises about 3% of 4-[7-(6-cyano-5-trifluoromethylpyridin-3-yl)-8-oxo-6-thioxo-5,7-diazaspiro[3.4]oct-5-yl]-2-fluoro-N-methylbenzamide.

In some embodiments, a single unit dosage of the pharmaceutical composition comprises about 30 mg of 4-[7-(6-cyano-5-trifluoromethylpyridin-3-yl)-8-oxo-6-thioxo-5,7-diazaspiro[3.4]oct-5-yl]-2-fluoro-N-methylbenzamide. In some embodiments, multiple doses of the single unit dosage pharmaceutical composition comprising about 30 mg of 4-[7-(6-cyano-5-trifluoromethylpyridin-3-yl)-8-oxo-6-thioxo-5,7-diazaspiro[3.4]oct-5-yl]-2-fluoro-N-methylbenzamide are administered to the human.

In some embodiments, a single unit dosage of the pharmaceutical composition comprises 4-[7-(6-cyano-5-trifluoromethylpyridin-3-yl)-8-oxo-6-thioxo-5,7-diazaspiro[3.4]oct-5-yl]-2-fluoro-N-methylbenzamide and at least one of the following compounds: 4-[7-(6-cyano-5-trifluoromethylpyridin-3-yl)-8-oxo-6-thioxo-5,7-diazaspiro[3.4]oct-5-yl]-N-methylbenzamide, 4-[7-(6-cyano-5-trifluoromethylpyridin-3-yl)-8-thioxo-6-thioxo-5,7-diazaspiro[3.4]oct-5-yl]-2-fluoro-N-methylbenzamide, methyl 4-(7-(6-cyano-5-(trifluoromethyl)pyridin-3-yl)-8-oxo-6-thioxo-5,7-diazaspiro[3.4]octan-5-yl)-2-fluorobenzoate, 4-(7-(6-cyano-5-(trifluoromethyl)pyridin-3-yl)-8-oxo-6-thioxo-5,7-diazaspiro[3.4]octan-5-yl)-2-fluorobenzoic acid, 4-(7-(6-cyano-5-(difluoromethyl)pyridin-3-yl)-8-oxo-6-thioxo-5,7-diazaspiro[3.4]octan-5-yl)-2-fluoro-N-methylbenzamide, 4-(7-(6-cyano-5-(trifluoromethyl)pyridin-3-yl)-8-oxo-6-thioxo-5,7-diazaspiro[3.4]octan-5-yl)-2-fluoro-N-methylbenzothioamide, 2-chloro-4-(7-(6-cyano-5-(trifluoromethyl)pyridin-3-yl)-8-oxo-6-thioxo-5,7-diazaspiro[3.4]octan-5- yl)-N-methylbenzamide, 5-amino-3-(trifluoromethyl)picolinonitrile, 1-((4-(methylcarbamoyl)phenyl)amino)cyclobutanecarboxylic acid or 1-(3-fluoro-4-(methylcarbamoyl)phenylamino)cyclobutanecarboxylic acid.

In some embodiments, a single unit dosage of the pharmaceutical composition comprises about 30 mg of 4-[7-(6-cyano-5-trifluoromethylpyridin-3-yl)-8-oxo-6-thioxo-5,7-diazaspiro[3.4]oct-5-yl]-2-fluoro-N-methylbenzamide and at least one of the following compounds: 4-[7-(6-cyano-5-trifluoromethylpyridin-3-yl)-8-oxo-6-thioxo-5,7-diazaspiro[3.4]oct-5-yl]-N-methylbenzamide, 4-[7-(6-cyano-5-trifluoromethylpyridin-3-yl)-8-thioxo-6-thioxo-5,7-diazaspiro[3.4]oct-5-yl]-2-fluoro-N-methylbenzamide, methyl 4-(7-(6-cyano-5-(trifluoromethyl)pyridin-3-yl)-8-oxo-6-thioxo-5,7-diazaspiro[3.4]octan-5-yl)-2-fluorobenzoate, 4-(7-(6-cyano-5-(trifluoromethyl)pyridin-3-yl)-8-oxo-6-thioxo-5,7-diazaspiro[3.4]octan-5-yl)-2-fluorobenzoic acid, 4-(7-(6-cyano-5-(difluoromethyl)pyridin-3-yl)-8-oxo-6-thioxo-5,7-diazaspiro[3.4]octan-5-yl)-2-fluoro-N-methylbenzamide, 4-(7-(6-cyano-5-(trifluoromethyl)pyridin-3-yl)-8-oxo-6-thioxo-5,7-diazaspiro[3.4]octan-5-yl)-2-fluoro-N-methylbenzothioamide, 2-chloro-4-(7-(6-cyano-5-(trifluoromethyl)pyridin-3-yl)-8-oxo-6-thioxo-5,7-diazaspiro[3.4]octan-5-yl)-N-methylbenzamide, 5-amino-3-(trifluoromethyl)picolinonitrile, 1-((4-(methylcarbamoyl)phenyl)amino)cyclobutanecarboxylic acid or 1-(3-fluoro-4-(methylcarbamoyl)phenylamino)cyclobutanecarboxylic acid.

In some embodiments, a single unit dosage of the pharmaceutical composition comprises about 30 mg of 4-[7-(6-cyano-5-trifluoromethylpyridin-3-yl)-8-oxo-6-thioxo-5,7-diazaspiro[3.4]oct-5-yl]-2-fluoro-N-methylbenzamide and at least one of the following compounds: 4-[7-(6-cyano-5-trifluoromethylpyridin-3-yl)-8-oxo-6-thioxo-5,7-diazaspiro[3.4]oct-5-yl]-N-methylbenzamide, 4-[7-(6-cyano-5-trifluoromethylpyridin-3-yl)-8-thioxo-6-thioxo-5,7-diazaspiro[3.4]oct-5-yl]-2-fluoro-N-methylbenzamide, methyl 4-(7-(6-cyano-5-(trifluoromethyl)pyridin-3-yl)-8-oxo-6-thioxo-5,7-diazaspiro[3.4]octan-5-yl)-2-fluorobenzoate, 4-(7-(6-cyano-5-(trifluoromethyl)pyridin-3-yl)-8-oxo-6-thioxo-5,7-diazaspiro[3.4]octan-5-yl)-2-fluorobenzoic acid, 4-(7-(6-cyano-5-(difluoromethyl)pyridin-3-yl)-8-oxo-6-thioxo-5,7-diazaspiro[3.4]octan-5-yl)-2-fluoro-N-methylbenzamide, 5-amino-3-(trifluoromethyl)picolinonitrile, 1-((4-(methylcarbamoyl)phenyl)amino)cyclobutanecarboxylic acid or 1-(3-fluoro-4-(methylcarbamoyl)phenylamino)cyclobutanecarboxylic acid.

In one aspect, described herein is a softgel pharmaceutical composition comprising a softgel capsule that is filled with a nonaqueous, lipid-based solution comprising 4-[7-(6-cyano-5-trifluoromethylpyridin-3-yl)-8-oxo-6-thioxo-5,7-diazaspiro[3.4]oct-5-yl]-2-fluoro-N-methylbenzamide and 4-[7-(6-cyano-5-trifluoromethylpyridin-3-yl)-8-thioxo-6-thioxo-5,7-diazaspiro[3.4]oct-5-yl]-N-methylbenzamide.

In one aspect, described herein is a softgel pharmaceutical composition comprising a softgel capsule that is filled with a nonaqueous, lipid-based solution comprising 4-[7-(6-cyano-5-trifluoromethylpyridin-3-yl)-8-oxo-6-thioxo-5,7-diazaspiro[3.4]oct-5-yl]-2-fluoro-N-methylbenzamide and methyl 4-(7-(6-cyano-5-(trifluoromethyl)pyridin-3-yl)-8-oxo-6-thioxo-5,7-diazaspiro[3.4]octan-5-yl)-2-fluorobenzoate.

In one aspect, described herein is a softgel pharmaceutical composition comprising a softgel capsule that is filled with a nonaqueous, lipid-based solution comprising 4-[7-(6-cyano-5-trifluoromethylpyridin-3-yl)-8-oxo-6-thioxo-5,7-diazaspiro[3.4]oct-5-yl]-2-fluoro-N-methylbenzamide and 4-(7-(6-cyano-5-(trifluoromethyl)pyridin-3-yl)-8-oxo-6-thioxo-5,7-diazaspiro[3.4]octan-5-yl)-2-fluorobenzoic acid.

In one aspect, described herein is a softgel pharmaceutical composition comprising a softgel capsule that is filled with a nonaqueous, lipid-based solution comprising 4-[7-(6-cyano-5-trifluoromethylpyridin-3-yl)-8-oxo-6-thioxo-5,7-diazaspiro[3.4]oct-5-yl]-2-fluoro-N-methylbenzamide and 4-(7-(6-cyano-5-(difluoromethyl)pyridin-3-yl)-8-oxo-6-thioxo-5,7-diazaspiro[3.4]octan-5-yl)-2-fluoro-N-methylbenzamide.

In one aspect, described herein is a softgel pharmaceutical composition comprising a softgel capsule that is filled with a nonaqueous, lipid-based solution comprising 4-[7-(6-cyano-5-trifluoromethylpyridin-3-yl)-8-oxo-6-thioxo-5,7-diazaspiro[3.4]oct-5-yl]-2-fluoro-N-methylbenzamide and 1-((4-(methylcarbamoyl)phenyl)amino)cyclobutanecarboxylic acid.

In one aspect, described herein is a softgel pharmaceutical composition comprising a softgel capsule that is filled with a nonaqueous, lipid-based solution comprising 4-[7-(6-cyano-5-trifluoromethylpyridin-3-yl)-8-oxo-6-thioxo-5,7-diazaspiro[3.4]oct-5-yl]-2-fluoro-N-methylbenzamide and 1-(3-fluoro-4-(methylcarbamoyl)phenylamino)cyclobutanecarboxylic acid.

These formulations are manufactured by conventional formulation techniques. There are several procedures to prepare softgelatin capsules, such as the plate process, the rotary die process, and reciprocating die process. In some embodiments, softgel capsules of 4-[7-(6-cyano-5-trifluoromethylpyridin-3-yl)-8-oxo-6-thioxo-5,7-diazaspiro[3.4]oct-5-yl]-2-fluoro-N-methylbenzamide are prepared as outlined in the Examples.

All formulations for oral administration are in dosages suitable for such administration.

In one aspect, described is the compound 1-(3-(6-cyano-5-(trifluoromethyl)pyridin-3-yl)-1-(3-fluoro-4-(methylcarbamoyl)phenyl)ureido)-cyclobutanecarboxylic acid. In some embodiments, described is a pharmaceutically acceptable salt of 1-(3-(6-cyano-5-(trifluoromethyl)pyridin-3-yl)-1-(3-fluoro-4-(methylcarbamoyl)phenyl)ureido)-cyclobutanecarboxylic acid. In some embodiments, described is a pharmaceutical composition comprising 1-(3-(6-cyano-5-(trifluoromethyl)pyridin-3-yl)-1-(3-fluoro-4-(methylcarbamoyl)phenyl)ureido)-cyclobutanecarboxylic acid, or a pharmaceutically acceptable salt thereof.

In another aspect, described is the compound 4-(7-(6-cyano-5-(difluoromethyl)pyridin-3-yl)-8-oxo-6-thioxo-5,7-diazaspiro[3.4]octan-5-yl)-2-fluoro-N-methylbenzamide. In some embodiments, described is a pharmaceutically acceptable salt of 4-(7-(6-cyano-5-(difluoromethyl)pyridin-3-yl)-8-oxo-6-thioxo-5,7-diazaspiro[3.4]octan-5-yl)-2-fluoro-N-methylbenzamide. In some embodiments, described is a pharmaceutical composition comprising 4-(7-(6-cyano-5-(difluoromethyl)pyridin-3-yl)-8-oxo-6-thioxo-5,7-diazaspiro[3.4]octan-5-yl)-2-fluoro-N-methylbenzamide, or a pharmaceutically acceptable salt thereof.

In any of the embodiments described herein, 4-[7-(6-cyano-5-trifluoromethylpyridin-3-yl)-8-oxo-6-thioxo-5,7-diazaspiro[3.4]oct-5-yl]-2-fluoro-N-methylbenzamide is replaced with 1-(3-(6-cyano-5-(trifluoromethyl)pyridin-3- yl)-1-(3-fluoro-4-(methylcarbamoyl)phenyl)ureido)-cyclobutanecarboxylic acid, or a pharmaceutically acceptable salt thereof.

In any of the embodiments described herein, 4-[7-(6-cyano-5-trifluoromethylpyridin-3-yl)-8-oxo-6-thioxo-5,7-diazaspiro[3.4]oct-5-yl]-2-fluoro-N-methylbenzamide is replaced with 4-(7-(6-cyano-5-(trifluoromethyl)pyridin-3-yl)-6,8-dioxo-5,7-diazaspiro[3.4]octan-5-yl)-2-fluoro-N-methylbenzamide, or a pharmaceutically acceptable salt thereof.

In any of the embodiments described herein, 4-[7-(6-cyano-5-trifluoromethylpyridin-3-yl)-8-oxo-6-thioxo-5,7-diazaspiro[3.4]oct-5-yl]-2-fluoro-N-methylbenzamide is replaced with 4-(7-(6-cyano-5-(trifluoromethyl)pyridin-3-yl)-8-oxo-6-thioxo-5,7-diazaspiro[3.4]octan-5-yl)-2-fluorobenzamide, or a pharmaceutically acceptable salt thereof.

In any of the embodiments described herein, 4-[7-(6-cyano-5-trifluoromethylpyridin-3-yl)-8-oxo-6-thioxo-5,7-diazaspiro[3.4]oct-5-yl]-2-fluoro-N-methylbenzamide is replaced with 4-(7-(6-cyano-5-(trifluoromethyl)pyridin-3-yl)-8-oxo-6-thioxo-5,7-diazaspiro[3.4]octan-5-yl)-2-fluorobenzoic acid, or a pharmaceutically acceptable salt thereof.

In any of the embodiments described herein, 4-[7-(6-cyano-5-trifluoromethylpyridin-3-yl)-8-oxo-6-thioxo-5,7-diazaspiro[3.4]oct-5-yl]-2-fluoro-N-methylbenzamide is replaced with 4-(7-(6-cyano-5-(difluoromethyl)pyridin-3-yl)-8-oxo-6-thioxo-5,7-diazaspiro[3.4]octan-5-yl)-2-fluoro-N-methylbenzamide, or a pharmaceutically acceptable salt thereof.

Methods of Dosing and Treatment Regimens

In one aspect, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered daily to humans in need of therapy with 4-[7-(6-cyano-5-trifluoromethylpyridin-3-yl)-8-oxo-6-thioxo-5,7-diazaspiro[3.4]oct-5-yl]-2-fluoro-N-methylbenzamide. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is orally administered to the humans. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered once-a-day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered twice-a-day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered three times-a-day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered every other day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered twice a week. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered weekly. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered every other week.

In general, doses of a 4-[7-(6-cyano-5-trifluoromethylpyridin-3-yl)-8-oxo-6-thioxo-5,7-diazaspiro[3.4]oct-5-yl]-2-fluoro-N-methylbenzamide employed for treatment of the diseases or conditions described herein in humans are typically in the range of 10 mg to 1000 mg per day. In one embodiment, the desired dose is conveniently presented in a single dose or in divided doses administered simultaneously (or over a short period of time) or at appropriate intervals, for example as two, three, four or more sub-doses per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is conveniently presented in divided doses that are administered simultaneously (or over a short period of time) once a day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is conveniently presented in divided doses that are administered in equal portions twice-a-day.

In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered daily to the human. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the human. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the human at a dose of about 30 mg per day to about 960 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the human at a dose of about 30 mg per day to about 480 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the human at a dose of about 180 mg per day to about 480 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the human at a dose of about 30 mg per day, about 60 mg per day, about 90 mg per day, about 120 mg per day, about 180 mg per day, about 240 mg per day, about 300 mg per day, about 390 mg per day, about 480 mg per day, about 600 mg per day, about 780 mg per day, or about 960 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the human at a dose of about 240 mg per day. In some embodiments, greater than 240 mg per day of 4-[7-(6-cyano-5-trifluoromethylpyridin-3-yl)-8-oxo-6-thioxo-5,7-diazaspiro[3.4]oct-5-yl]-2-fluoro-N-methylbenzamide is administered to the human. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the human on a continuous daily dosing schedule.

In some embodiments, the amount of 4-[7-(6-cyano-5-trifluoromethylpyridin-3-yl)-8-oxo-6-thioxo-5,7-diazaspiro[3.4]oct-5-yl]-2-fluoro-N-methylbenzamide is administered once-a-day. In some other embodiments, the amount of 4-[7-(6-cyano-5-trifluoromethylpyridin-3-yl)-8-oxo-6-thioxo-5,7-diazaspiro[3.4]oct-5-yl]-2-fluoro-N-methylbenzamide is administered twice-a-day.

In certain embodiments wherein improvement in the status of the disease or condition in the human is not observed, the daily dose of 4-(3-(4-cyano-3-(trifluoromethyl)phenyl)-5,5-dimethyl-4-oxo-2-thioxoimidazolidin-1-yl)-2-fluoro-N-methylbenzamide is increased. In some embodiments, a once-a-day dosing schedule is changed to a twice-a-day dosing schedule. In some embodiments, a three times a day dosing schedule is employed to increase the amount of 4-(3-(4-cyano-3-(trifluoromethyl)phenyl)-5,5-dimethyl-4-oxo-2-thioxoimidazolidin-1-yl)-2-fluoro-N-methylbenzamide that is administered.

In some embodiments, the amount of 4-(3-(4-cyano-3-(trifluoromethyl)phenyl)-5,5-dimethyl-4-oxo-2-thioxoimidazolidin-1-yl)-2-fluoro-N-methylbenzamide that is given to the human varies depending upon factors such as, but not limited to, condition and severity of the disease or condition, and the identity (e.g., weight) of the human, and the particular additional therapeutic agents that are administered (if applicable).

Combination Therapies

In certain instances, it is appropriate to administer a second generation anti-androgen (e.g. 4-[7-(6-cyano-5-trifluoromethylpyridin-3-yl)-8-oxo-6-thioxo-5,7-diazaspiro[3.4]oct-5-yl]-2-fluoro-N-methylbenzamide), in combination with another therapeutic agent.

In one specific embodiment, the second generation anti-androgen is co-administered with an additional therapeutic agent, wherein the second generation anti-androgen and the additional therapeutic agent modulate different aspects of the disease or condition being treated, thereby providing a greater overall benefit than administration of either therapeutic agent alone.

In any case, regardless of the disease, disorder or condition being treated, the overall benefit experienced by the patient may simply be additive of the two therapeutic agents or the patient may experience a synergistic benefit.

It is understood that the dosage regimen to treat, prevent, or ameliorate the condition(s) for which relief is sought, is modified in accordance with a variety of factors. These factors include the disease, disorder or condition from which the subject suffers, as well as the age, weight, sex, diet, and medical condition of the subject. Thus, in some instances, the dosage regimen actually employed varies and, in some embodiments, deviates from the dosage regimens set forth herein.

In combination therapies, the multiple therapeutic agents (one of which is one of the compounds described herein) are administered in any order or even simultaneously. Combination therapies are not to be limited to the use of only two agents; the use of multiple therapeutic combinations is also envisioned.

In some embodiments, methods for treatment of prostate cancer described herein comprise administration of a second generation anti-androgen to a human in combination with at least one additional therapeutic agent. In some embodiments, the cancer is advanced prostate cancer. In a further embodiment, the cancer is castration-sensitive. In a further embodiment, the cancer is castration-resistant prostate cancer. In a further embodiment, the cancer is high-risk localized prostate cancer. In some embodiments, the combination therapy is targeted toward patients identified with castration-resistant prostate cancer (CRPC) that exhibits intrinsic or acquired resistance to abiraterone acetate and/or MDV-3100.

In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is used to treat prostate cancer in a human in combination with another therapeutic agent. In one embodiment, the prostate cancer is metastatic castration-resistant prostate cancer, non-metastatic castration-resistant prostate cancer, metastatic castration-sensitive prostate cancer, non-metastatic castration-sensitive prostate cancer or high-risk localized prostate cancer. Given the central role of AR in prostate cancer development and progression, 4-[7-(6-cyano-5-trifluoromethylpyridin-3-yl)-8-oxo-6-thioxo-5,7-diazaspiro[3.4]oct-5-yl]-2-fluoro-N-methylbenzamide is useful in the treatment of advanced prostate cancer, either alone or in combination with other agents that can modulate other critical pathways in prostate cancer, including but not limited to those that target IGF1R, the PI3K/AKT/mTOR axis, or HSP90.

In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide or a pharmaceutical composition thereof is administered in combination with an additional therapeutic agent including but not limited to: PI3K inhibitors, TORC inhibitors, CYP17 inhibitors, GNRH/LHRH agonists/antagonists, osteoprotective agents, radiation, kinase inhibitors (e.g. MET, VEGFR, EGFR, MEK, SRC, AKT, RAF, FGFR, CDK4/6), immunotherapy, taxanes, tubuin inhibitors, STEAP-1 anti-body drug conjugate (ADC), HSP90/HSP27 pathway modulators.

In certain instances, it is appropriate to administer a second generation anti-androgen (e.g. 4-[7-(6-cyano-5-trifluoromethylpyridin-3-yl)-8-oxo-6-thioxo-5,7-diazaspiro[3.4]oct-5-yl]-2-fluoro-N-methylbenzamide), in combination with a TORC inhibitor, PI3K inhibitor, CYP17 inhibitor, GNRH agonist or antagonist, osteoprotective agent, Syk inhibitor, RANKL inhibitor, MET inhibitor, VEGFR inhibitor, EGFR inhibitor, FGFR inhibitor, MEK inhibitor, Src inhibitor, AKT inhibitor, RAF inhibitor, CDK4 inhibitor, or CDK6 inhibitor.

In certain instances, it is appropriate to administer a second generation anti-androgen (e.g. 4-[7-(6-cyano-5-trifluoromethylpyridin-3-yl)-8-oxo-6-thioxo-5,7-diazaspiro[3.4]oct-5-yl]-2-fluoro-N-methylbenzamide), in combination with abiraterone acetate, Everolimus, GDC-0980, GDC-0068, (GDC-0980+GDC-0068), GSK-2636771, BEZ-235, BKM120, BGT226, BYL-719, GDC0941, GDC0032, INK1117, MK-2206, OSI-027, CC-223, AZD8055, SAR245408, SAR245409, PF04691502, WYE125132, GSK2126458, BAY806946, PF-05212384, SF1126, PX866, AMG319, ZSTK474, Cal101, PWT33597, LY-317615 (Enzastaurin hydrochloride), CU-906, CUDC-907, Abi, TAK700, TOK-001 (Galeterone), VT-464, Lupron, Zoladex (Goserelin-LHRH agonist), Degarelix (GNRH antagonist), Ozarelix, ABT-620 (Elagolix), TAK-385 (Relugolix), TAK-448, EP-100, KLH-2109, Denosumab (RANKL Ab), Zolendronic acid (bisphosphonate), OCIF (OPG), AMG-0007, CEP-37251, ALX-0141, Alendronate sodium (Fosamax), Pamidronate sodium (Aredia), Neridronic acid (Nerixia), Minodronic acid (Recalbon), Risedronate sodium (Actonel), Alpharadin, 177Lu-J59 (PSMA monoclonal AbJ591-radioimmunoconjugate), External beam radiation therapy, brachytherapy, Cabozantinib (XL184) Met/VEGR2, PF-2341066 (Crizotinib), ARQ-197 (Tivantinib), MK-2461, JNJ-38877605, MK-8033, INCB-28060, BMS-777607, AMG-208, LY-2801653, EMD-1214063, EMD-1204831, AMG-337, HM-5016504 (Volitinib), SAR-125844, LY2875358, ABR-215050 (Tasquinimod), CHIR-258 (Dovitinib), EXEL-7647, OSI-930, BIBF-1120, BAY-73-4506, BAY-73-4506, BMS-582664 (Brivanib), RO-4929097, JNJ-26483327, AZD-2171 (Cediranib), Sorafenib, Aflibercept, Enzastaurin, AG-013736 (Axitinib), GSK-786034 (Pazopanib), GSK-786034 (Pazopanib), AP-23573, BMS-354825 (Dasatinib), PROVENGE™ (sipuleucel-T), PROSTVAC™ (rilimogene galvacirepvec/rilimogene glafolivec)-VF, Ipilimumab, CTLA4 inhibitors, PD-1 inhibitors, ChK inhibitors, Docetaxel, Cabazitaxel, taxanes, tubulin inhibitors, Anti-STEAP1 ADC, STEAP-1, Tarceva (EGFR1), Trametinib (MEK inhibitor GSK), Cetuximab, Gefitinib, Canertinib, Panitumumab, Nimotuzumab, OSI-632, Lapatinib, Vandetanib, Afatinib, MP-412, AEE-788, Neratinib, XL-647, AC-480, Dacomitinib, AZD-8931, CUDC-101, AP-26113, CO-1686, Selumetinib, MEK-162, Refametinib, TAK-733, RO-5126766, BI-847325, AZD6244, GSK1120212, PF-5208763 (Bosutinib), AZD-0530 (Saracatinib), OGX-11

(Custirsen, anti-clusterin), OGX-427 (Anti-HSP27), AUY922, HSP990, AT13387, GDC0068, MK-2206, AT7867, GSK2110183, GSK2141795, GSK690693, PLX4032/RG7204, GSK2118436, GSK208436, LGX818, RAF265, LY2780301, LY2584702, Dovitinib (TKI258), BGJ398, AZD4547, PD-0332991 or LEE011; or combinations thereof.

In certain instances, it is appropriate to administer a second generation anti-androgen (e.g. 4-[7-(6-cyano-5-trifluoromethylpyridin-3-yl)-8-oxo-6-thioxo-5,7-diazaspiro[3.4]oct-5-yl]-2-fluoro-N-methylbenzamide), in combination with an anti-estrogen (e.g., tamoxifen), an anti-androgen (e.g., bicalutamide, flutamide), gonadotropin releasing hormone analog (e.g., leuprolide).

In certain instances, it is appropriate to administer a second generation anti-androgen (e.g. 4-[7-(6-cyano-5-trifluoromethylpyridin-3-yl)-8-oxo-6-thioxo-5,7-diazaspiro[3.4]oct-5-yl]-2-fluoro-N-methylbenzamide), in combination with anti-emetic agents to treat nausea or emesis, which may result from the use of the second generation anti-androgen, anti-cancer agent(s) and/or radiation therapy. Anti-emetic agents include, but are not limited to: neurokinin-1 receptor antagonists, 5HT3 receptor antagonists (such as ondansetron, granisetron, tropisetron, Palonosetron, and zatisetron), $GABA_B$ receptor agonists (such as baclofen), corticosteroids (such as dexamethasone, prednisone, prednisolone, or others), dopamine antagonists (such as, but not limited to, domperidone, droperidol, haloperidol, chlorpromazine, promethazine, prochlorperazine, metoclopramide), antihistamines (H1 histamine receptor antagonists, such as but not limited to, cyclizine, diphenhydramine, dimenhydrinate, meclizine, promethazine, hydroxyzine), cannabinoids (such as but not limited to, cannabis, marinol, dronabinol), and others (such as, but not limited to, trimethobenzamide; ginger, emetrol, propofol).

Combination with a PI3K/TORC Inhibitor

In some embodiments, patients with prostate may exhibit intrinsic or acquired resistance to 2nd generation anti-hormonal therapies such as abiraterone acetate, MDV-3100 & 4-[7-(6-cyano-5-trifluoromethylpyridin-3-yl)-8-oxo-6-thioxo-5,7-diazaspiro[3.4]oct-5-yl]-2-fluoro-N-methylbenzamide. In both intrinsic and acquired endocrine resistance, signaling via other critical pathways is thought to be a key determinant of the resistant phenotype. Deregulation of the PI3K pathway (e.g. PTEN deletion) is one of the most prevalent alterations found in prostate cancer. Recently, activation of the PI3K pathway has been shown to confer intrinsic resistance to hormonal therapy in the PTEN KO model of prostate cancer (Carver et al. "Reciprocal feedback regulation of PI3K and androgen receptor signaling in PTEN-deficient prostate cancer." Cancer Cell. 2011 May 17; 19(5):575-86; Mulholland et at "Cell autonomous role of PTEN in regulating castration-resistant prostate cancer growth." Cancer Cell. 2011 June 14; 19(6):792-804). In some embodiments, combination of Complete Androgen Blockade (CAB) (GNRH+ 4-[7-(6-cyano-5-trifluoromethylpyridin-3-yl)-8-oxo-6-thioxo-5,7-diazaspiro[3.4]oct-5-yl]-2-fluoro-N-methylbenzamide)+PI3K pathway inhibition in CRPC patients has the potential to overcome both intrinsic and extrinsic resistance to 2nd generation hormonal therapies.

In some embodiments, overexpression of wild type androgen receptor 3-5 fold in the LNCaP (LNCaP/AR) cell line confers a castration resistant phenotype both in vitro and in vivo. In some embodiments, it was observed that 4-[7-(6-cyano-5-trifluoromethylpyridin-3-yl)-8-oxo-6-thioxo-5,7-diazaspiro[3.4]oct-5-yl]-2-fluoro-N-methylbenzamide at doses from 10-30 mg/kg/day causes nearly full regression of all treated LNCaP/AR tumors, whereas a dose of 1 mg/kg/day results in a mean response of tumor stasis. In some embodiments, treatment with PI3K inhibitors SAR245408 or BKM120 or the TORC1 inhibitor everoliomus (all at or near their respective maximally efficacious dose) exhibit a range of efficacy from tumor growth inhibition to tumor stasis. In some embodiments, combining 4-[7-(6-cyano-5-trifluoromethylpyridin-3-yl)-8-oxo-6-thioxo-5,7-diazaspiro[3.4]oct-5-yl]-2-fluoro-N-methylbenzamide 1 mg/kg/day+PI3K pathway inhibition via the compounds noted above, resulted in increased efficacy (tumor regression) compared to either agent alone.

In some embodiments, in the PTEN KO genetically engineered mouse model of prostate cancer, combined androgen blockage or CAB (castration+MDV3100 or castration+4-[7-(6-cyano-5-trifluoromethylpyridin-3-yl)-8-oxo-6-thioxo-5, 7-diazaspiro[3.4]oct-5-yl]-2-fluoro-N-methylbenzamide) exhibits minimal efficacy. In some embodiments, monotherapy with pan-PI3K pathway inhibition with BEZ-235 also has minimal anti-tumor activity. In contrast, in some embodiments the combination of CAB with BEZ-235 resulted in significant reduction in tumor volume in all animals treated.

In one aspect, described herein is a method of treating prostate cancer in a male human comprising administering a second generation anti-androgen to a male human with post-abiraterone acetate treated metastatic castration-resistant prostate cancer, metastatic castration-resistant prostate cancer, non-metastatic castration-resistant prostate cancer, metastatic castration-sensitive prostate cancer, non-metastatic castration-sensitive prostate cancer or high-risk localized prostate cancer in combination with a phosphoinositide 3-kinase (PI3K) inhibitor, TORC inhibitor, or dual PI3K/TORC inhibitor. In some embodiments, the second generation anti-androgen is MDV-3100 or 4-[7-(6-cyano-5-trifluoromethylpyridin-3-yl)-8-oxo-6-thioxo-5,7-diazaspiro[3.4]oct-5-yl]-2-fluoro-N-methylbenzamide. In some embodiments, the second generation anti-androgen is MDV-3100. In some embodiments, the second generation anti-androgen is 4-[7-(6-cyano-5-trifluoromethylpyridin-3-yl)-8-oxo-6-thioxo-5, 7-diazaspiro[3.4]oct-5-yl]-2-fluoro-N-methylbenzamide.

In one aspect, described herein is a method of treating prostate cancer in a male human comprising administering 4-[7-(6-cyano-5-trifluoromethylpyridin-3-yl)-8-oxo-6-thioxo-5,7-diazaspiro[3.4]oct-5-yl]-2-fluoro-N-methylbenzamide at a dose of about 30 mg per day to about 480 mg per day to a male human with post-abiraterone acetate treated metastatic castration-resistant prostate cancer, metastatic castration-resistant prostate cancer, non-metastatic castration-resistant prostate cancer, metastatic castration-sensitive prostate cancer, non-metastatic castration-sensitive prostate cancer or high-risk localized prostate cancer in combination with a phosphoinositide 3-kinase (PI3K) inhibitor, TORC inhibitor, or dual PI3K/TORC inhibitor. In some embodiments, the method of treating prostate cancer further comprises administering a therapeutically effective amount of a gonadotropin-releasing hormone agonist or antagonist to the male human.

In some embodiments, the phosphoinositide 3-kinase (PI3K) inhibitor, TORC inhibitor, or dual PI3K/TORC inhibitor is everolimus, BEZ-235, BKM120, BGT226, BYL-719, GDC0068, GDC-0980, GDC0941, GDC0032, MK-2206, OSI-027, CC-223, AZD8055, SAR245408, SAR245409, PF04691502, WYE125132, GSK2126458, GSK-2636771, BAY806946, PF-05212384, SF1126, PX866, AMG319, ZSTK474, Cal101, PWT33597, LY-317615 (enzastaurin hydrochloride), CU-906, or CUDC-907.

In some embodiments, the TORC inhibitor is everolimus. In some embodiments, everolimus is administered at a dose of about 5 mg per day to about 20 mg per day. In some embodiments, everolimus is administered at a dose of about 5 mg per day or about 10 mg per day.

In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally at a dose of about 120 mg per day to about 240 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally at a dose of about 240 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally in the form of a softgel capsule.

Combination with a CYP17 Inhibitor

In some embodiments, incomplete target or pathway suppression can result in less than optimal therapeutic response. One way to overcome this and maximize treatment outcomes is inhibit multiple nodes within a given pathway. In some embodiments, hormonal treatment in prostate cancer include a GNRH agonist (e.g. Lupron) in combination with an anti-androgen (bicalutamide, MDV3100 or 4-[7-(6-cyano-5-trifluoromethylpyridin-3-yl)-8-oxo-6-thioxo-5,7-diazaspiro[3.4]oct-5-yl]-2-fluoro-N-methylbenzamide). In some embodiments, further suppression of androgen levels to below castrate levels comprises the combination of a CYP17 inhibitor with a GNRH agonist and an anti-androgen.

In one aspect, described herein is a method of treating prostate cancer in a male human comprising administering a second generation anti-androgen to a male human with metastatic castration-resistant prostate cancer, non-metastatic castration-resistant prostate cancer, metastatic castration-sensitive prostate cancer, non-metastatic castration-sensitive prostate cancer or high-risk localized prostate cancer in combination with a CYP17 inhibitor. In some embodiments, the second generation anti-androgen is MDV-3100 or 4-[7-(6-cyano-5-trifluoromethylpyridin-3-yl)-8-oxo-6-thioxo-5,7-diazaspiro[3.4]oct-5-yl]-2-fluoro-N-methylbenzamide. In some embodiments, the second generation anti-androgen is MDV-3100. In some embodiments, the second generation anti-androgen is 4-[7-(6-cyano-5-trifluoromethylpyridin-3-yl)-8-oxo-6-thioxo-5,7-diazaspiro[3.4]oct-5-yl]-2-fluoro-N-methylbenzamide.

In some embodiments, described herein is a method of treating prostate cancer in a male human comprising administering 4-[7-(6-cyano-5-trifluoromethylpyridin-3-yl)-8-oxo-6-thioxo-5,7-diazaspiro[3.4]oct-5-yl]-2-fluoro-N-methylbenzamide at a dose of about 30 mg per day to about 480 mg per day to a male human with metastatic castration-resistant prostate cancer, non-metastatic castration-resistant prostate cancer, metastatic castration-sensitive prostate cancer, non-metastatic castration-sensitive prostate cancer or high-risk localized prostate cancer in combination with a CYP17 inhibitor.

In some embodiments, the method of treating prostate cancer further comprises administering a therapeutically effective amount of a gonadotropin-releasing hormone agonist or antagonist to the male human.

In some embodiments, the CYP17 inhibitor is abiraterone acetate (Zytiga), TAK-700 (orteronel), TOK-001 (galeterone) or VT-464.

In some embodiments, the CYP17 inhibitor is abiraterone acetate (Zytiga). In some embodiments, abiraterone acetate (Zytiga) is administered at a dose of about 500 mg per day to about 1000 mg per day. In some embodiments, abiraterone acetate (Zytiga) is administered at a dose of about 1000 mg per day. In some embodiments, abiraterone acetate is administered in combination with prednisone. In some embodiments, abiraterone acetate is administered once a day and prednisone is administered twice a day.

In some embodiments, the CYP17 inhibitor is TAK-700 (orteronel). In some embodiments, TAK-700 (orteronel) is administered at a dose of about 300 mg twice per day to about 600 mg twice per day.

In some embodiments, TAK-700 (orteronel) is administered at a dose of about 300 mg twice per day to about 600 mg twice per day, together with prednisone at about 5 mg twice per day.

In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally at a dose of about 120 mg per day to about 240 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally at a dose of about 240 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally in the form of a softgel capsule.

Combination with a GnRH Agonist or Antagonist

In one aspect, described herein is a method of treating prostate cancer in a male human comprising administering a second generation anti-androgen to a male human with metastatic castration-resistant prostate cancer, non-metastatic castration-resistant prostate cancer, metastatic castration-sensitive prostate cancer, non-metastatic castration-sensitive prostate cancer or high-risk localized prostate cancer in combination with a gonadotropin-releasing hormone agonist or antagonist. In some embodiments, the second generation anti-androgen is MDV-3100 or 4-[7-(6-cyano-5-trifluoromethylpyridin-3-yl)-8-oxo-6-thioxo-5,7-diazaspiro[3.4]oct-5-yl]-2-fluoro-N-methylbenzamide. In some embodiments, the second generation anti-androgen is MDV-3100. In some embodiments, the second generation anti-androgen is 4-[7-(6-cyano-5-trifluoromethylpyridin-3-yl)-8-oxo-6-thioxo-5,7-diazaspiro[3.4]oct-5-yl]-2-fluoro-N-methylbenzamide.

In one aspect, described herein is a method of treating prostate cancer in a male human comprising administering 4-[7-(6-cyano-5-trifluoromethylpyridin-3-yl)-8-oxo-6-thioxo-5,7-diazaspiro[3.4]oct-5-yl]-2-fluoro-N-methylbenzamide at a dose of about 30 mg per day to about 480 mg per day to a male human with metastatic castration-resistant prostate cancer, non-metastatic castration-resistant prostate cancer, metastatic castration-sensitive prostate cancer, non-metastatic castration-sensitive prostate cancer or high-risk localized prostate cancer in combination with a gonadotropin-releasing hormone agonist or antagonist.

Gonadotropin-releasing hormone (GnRH) is also known as Luteinizing-hormone-releasing hormone (LHRH).

In some embodiments, the gonadotropin-releasing hormone agonist or antagonist is Lupron, Zoladex (Goserelin), Degarelix, Ozarelix, ABT-620 (Elagolix), TAK-385 (Relugolix), EP-100 or KLH-2109.

In some embodiments, the gonadotropin-releasing hormone agonist or antagonist is Lupron. In some embodiments, Lupron is administered as a depot injection at a dose of about 7.5 mg every 4 weeks, or 22.5 mg every 3 months, or about 30 mg every 4 months, or about 45 mg every 6 months.

In some embodiments, the gonadotropin-releasing hormone agonist or antagonist is Zoladex (Goserelin). In some embodiments, Zoladex (Goserelin) is administered as a subcutaneous implant at a dose of about 3.6 mg every 4 weeks or about 10.8 mg every 12 weeks.

In some embodiments, the gonadotropin-releasing hormone agonist or antagonist is Degarelix. In some embodiments, Degarelix is administered as a subcutaneous injection at a dose of about 240 mg followed by about 80 mg administered every 4 weeks.

In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally at a dose of about 120 mg per day to about 240 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally at a dose of about 240 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally in the form of a softgel capsule.

Combination with an Osteoprotective Agent

Skeletal morbidity via bone metastases is a major cause of death in patients with castration resistance prostate cancer. In addition, long term androgen deprivation therapy results in loss of bone mineral density and increase in potential fractures. In some embodiments, osteoprotective agents prevent/delay skeletal events in men on androgen deprivation therapy (ADT) and have the potential to prevent/delay skeletal events in men on ADT+4-[7-(6-cyano-5-trifluoromethylpyridin-3-yl)-8-oxo-6-thioxo-5,7-diazaspiro[3.4]oct-5-yl]-2-fluoro-N-methylbenzamide. Osteoclasts, through paracrine effects, can influence the growth of bone mets. In some embodiments, combining a second generation anti-androigen with an osteoprotective agent may prevent formation of bones metastases and/or the growth of already established bone metastases.

In one aspect, described herein is a method of treating prostate cancer in a male human comprising administering a second generation anti-androgen to a male human with metastatic castration-resistant prostate cancer, non-metastatic castration-resistant prostate cancer, metastatic castration-sensitive prostate cancer, non-metastatic castration-sensitive prostate cancer or high-risk localized prostate cancer in combination with an osteoprotective agent. In some embodiments, the second generation anti-androgen is MDV-3100 or 4-[7-(6-cyano-5-trifluoromethylpyridin-3-yl)-8-oxo-6-thioxo-5,7-diazaspiro[3.4]oct-5-yl]-2-fluoro-N-methylbenzamide. In some embodiments, the second generation anti-androgen is MDV-3100. In some embodiments, the second generation anti-androgen is 4-[7-(6-cyano-5-trifluoromethylpyridin-3-yl)-8-oxo-6-thioxo-5,7-diazaspiro[3.4]oct-5-yl]-2-fluoro-N-methylbenzamide.

In one aspect, described herein is a method of treating prostate cancer in a male human comprising administering 4-[7-(6-cyano-5-trifluoromethylpyridin-3-yl)-8-oxo-6-thioxo-5,7-diazaspiro[3.4]oct-5-yl]-2-fluoro-N-methylbenzamide at a dose of about 30 mg per day to about 480 mg per day to a male human with metastatic castration-resistant prostate cancer, non-metastatic castration-resistant prostate cancer, metastatic castration-sensitive prostate cancer, non-metastatic castration-sensitive prostate cancer or high-risk localized prostate cancer with an osteoprotective agent.

In some embodiments, the method of treating prostate cancer further comprises administering a therapeutically effective amount of a gonadotropin-releasing hormone agonist or antagonist to the male human.

In some embodiments, the osteoprotective agent is Denosumab, AMG-0007, CEP-37251, ALX-0141, Zoledronic acid, Alendronate sodium (Fosamax), Pamidronate disodium (Aredia), Neridronic acid (Nerixia), Minodronic acid (Recalbon) or Risedronate sodium (Actonel).

In some embodiments, the osteoprotective agent is Denosumab. In some embodiments, Denosumab is administered by subcutaneous injection at a dose of about 60 mg to about 120 mg every 4 weeks to every 6 months.

In some embodiments, the osteoprotective agent is zoledronic acid. In some embodiments, zoledronic acid is administered by intravenous infusion at a dose of about 4 mg every 4 weeks to every 12 weeks.

In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally at a dose of about 120 mg per day to about 240 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally at a dose of about 240 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally in the form of a softgel capsule.

Combination with Radiation Therapy

Radiation induces tumor cell death via DNA damage subsequent induction of apoptosis. Induction of apoptosis in prostatic epithelium and prostate cancer cells through inhibition of the androgen receptor signaling pathway is well established in both pre-clinical models and in patients. Recently, it has been shown that the androgen receptor may regulate DNA repair mechanisms and thus combination of radiation and AR inhibition has the potential to increase DNA damage mediated apoptosis and thus anti-tumor efficacy.

A technique for delivering radiation to cancer cells is to place radioactive implants directly in a tumor or body cavity. This is called internal radiotherapy (brachytherapy, interstitial irradiation, and intracavitary irradiation are types of internal radiotherapy). Using internal radiotherapy, the radiation dose is concentrated in a small area.

The term "radiotherapy" or "ionizing radiation" include all forms of radiation, including but not limited to $\alpha$, $\beta$, and $\gamma$ radiation and ultraviolet light.

Another way of delivering radiation is by use of radiopharmaceuticals. Radiopharmaceuticals induce tumor cell death via DNA damage and subsequent induction of apoptosis. Alpharadin (Radium-223 Chloride) is an alpha-particle emitter that acts as calcium mimic and thus has propensity to home to bone and thus close proximity to bone metastases. It has been shown to prolong survival in castration resistant prostate cancer patients in a recently completed Phase 3 study. $^{177}$Lu-J591 is a deimmunized monoclonal antibody specific to the extracellular domain of prostate specific membrane antigen (PSMA) conjugated to the radiometal $^{177}$Lutium (beta emitter). The restricted expression pattern of PSMA results in selective delivery of $^{177}$Lutium to prostate cancer cells and thus in theory increased efficacy and decreased side effects.

Androgen receptor signaling provides prostate cancer cells with survival signals necessary for primary and metastatic tumor growth. Anti-androgen therapy has been shown to increase tumor apoptosis in preclinical models of CRPC and exhibit anti-tumor efficacy in man. Decrease in survival signaling via anti-androgen treatment will lower apoptotic threshold, increasing cell death inducing effects of radiopharmaceuticals. In some embodiments, combining an anti-androgen with $^{177}$Lu-J591 has an added benefit in that PSMA is under negative transcriptional control of the androgen receptor (in the absence of androgen PSMA levels increase). Thus, treatment of prostate cancer with a second generation antiandrogen will increase PSMA protein levels resulting in more $^{177}$Lu-J591 binding per cell and thus potentially increasing radiation induced cell death.

In one aspect, described herein is a method of treating prostate cancer in a male human comprising administering a second generation anti-androgen to a male human with metastatic castration-resistant prostate cancer, non-metastatic castration-resistant prostate cancer, metastatic castration-sensitive prostate cancer, non-metastatic castration-sensitive prostate cancer or high-risk localized prostate cancer in combination with a radiation therapy. In some embodiments, the second generation anti-androgen is MDV-3100 or 4-[7-(6-cyano-5-trifluoromethylpyridin-3-yl)-8-oxo-6-thioxo-5,7-diazaspiro[3.4]oct-5-yl]-2-fluoro-N-methylbenzamide. In some embodiments, the second generation anti-androgen is MDV-3100. In some embodiments, the second generation anti-androgen is 4-[7-(6-cyano-5-trifluoromethylpyridin-3-yl)-8-oxo-6-thioxo-5,7-diazaspiro[3.4]oct-5-yl]-2-fluoro-N-methylbenzamide.

In one aspect, described herein is a method of treating prostate cancer in a male human comprising administering 4-[7-(6-cyano-5-trifluoromethylpyridin-3-yl)-8-oxo-6-thioxo-5,7-diazaspiro[3.4]oct-5-yl]-2-fluoro-N-methylbenzamide at a dose of about 30 mg per day to about 480 mg per day to a male human with metastatic castration-resistant prostate cancer, non-metastatic castration-resistant prostate cancer, metastatic castration-sensitive prostate cancer, non-metastatic castration-sensitive prostate cancer or high-risk localized prostate cancer in combination with a radiation therapy.

In some embodiments, the method of treating prostate cancer further comprises administering a therapeutically effective amount of a gonadotropin-releasing hormone agonist or antagonist to the male human.

In some embodiments, the radiation therapy is Alpharadin, $^{177}$Lu-J591, external beam radiation therapy (including Proton beam), or brachytherapy.

In some embodiments, the radiation therapy is Alpharadin. In some embodiments, Alpharadin is administered by intravenous infusion at a dose of about 25 to about 50 kBq/kg every 4 weeks.

In some embodiments, the radiation therapy is $^{177}$Lu-J591. In some embodiments, $^{177}$Lu-J591 is administered by intravenous infusion at a dose of about 30 mCi/m2 to about 70 mCi/m2.

In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally at a dose of about 120 mg per day to about 240 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally at a dose of about 240 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally in the form of a softgel capsule.

Combination with a Kinase Inhibitor

Growth factor signaling pathways such as EGFR and RAS/RAF/Mek are mediators of tumor cell growth and survival. In some embodiments, these pathways are deregulated in prostate cancer (or at least a subset) and function in parallel to androgen receptor signaling to promote disease progression. In some embodiments, simultaneous inhibition of AR signaling and growth factor signaling increases efficacy of treatment across the spectrum of prostate cancer disease.

Metastasis to the bone in prostate cancer patients is associated with significant pain and mortality. cMet is involved in both tumor cell growth, survival and metastasis and VEGFR2 signaling promotes tumor angiogenesis. In some embodiments, combining a second generation anti-androgen with a suitable kinase inhibitor will simultaneously inhibit the activity of the androgen receptor and cMet signaling in the tumor, and VEGFR2 in the tumor endothelium, potentially resulting in robust inhibition of both formation of prostate cancer associated bone metastases as well as growth of established bone metastases In one aspect, described herein is a method of treating prostate cancer in a male human comprising administering a second generation anti-androgen to a male human with post-abiraterone acetate treated metastatic castration-resistant prostate cancer, metastatic castration-resistant prostate cancer, non-metastatic castration-resistant prostate cancer, metastatic castration-sensitive prostate cancer, non-metastatic castration-sensitive prostate cancer or high-risk localized prostate cancer in combination with a kinase inhibitor. In some embodiments, the second generation anti-androgen is MDV-3100 or 4-[7-(6-cyano-5-trifluoromethylpyridin-3-yl)-8-oxo-6-thioxo-5,7-diazaspiro[3.4]oct-5-yl]-2-fluoro-N-methylbenzamide. In some embodiments, the second generation anti-androgen is MDV-3100. In some embodiments, the second generation anti-androgen is 4-[7-(6-cyano-5-trifluoromethylpyridin-3-yl)-8-oxo-6-thioxo-5,7-diazaspiro[3.4]oct-5-yl]-2-fluoro-N-methylbenzamide.

In one aspect, described herein is a method of treating prostate cancer in a male human comprising administering 4-[7-(6-cyano-5-trifluoromethylpyridin-3-yl)-8-oxo-6-thioxo-5,7-diazaspiro[3.4]oct-5-yl]-2-fluoro-N-methylbenzamide at a dose of about 30 mg per day to about 480 mg per day to a male human with post-abiraterone acetate treated metastatic castration-resistant prostate cancer, metastatic castration-resistant prostate cancer, non-metastatic castration-resistant prostate cancer, metastatic castration-sensitive prostate cancer, non-metastatic castration-sensitive prostate cancer or high-risk localized prostate cancer in combination with a kinase inhibitor.

In some embodiments, the method of treating prostate cancer further comprises administering a therapeutically effective amount of a gonadotropin-releasing hormone agonist or antagonist to the male human.

In some embodiments, the kinase inhibitor targets angiogenesis or bone metastases. In some embodiments, the kinase inhibitor is a MET or VEGFR kinase inhibitor. In some embodiments, the kinase inhibitor is Cabozantinib (XL184), PF-2341066 (Crizotinib), ARQ-197 (Tivantinib), MK-2461, JNJ-38877605, MK-8033, INCB-28060, BMS-777607, AMG-208, LY-2801653, EMD-1214063, EMD-1204831, AMG-337, HMPL-504 (Volitinib), SAR-125844, LY2875358, ABR-215050 (Tasquinimod), CHIR-258 (Dovitinib), EXEL-7647, OSI-930, BIBF-1120, BAY-73-4506 (Regorafenib), BMS-582664 (Brivanib), JNJ-26483327, AZD-2171 (Cediranib), Sorafenib, Aflibercept, Enzastaurin, AG-013736 (Axitinib), OSI-632, or GSK-786034 (Pazopanib). In some embodiments, the kinase inhibitor is Cabozantinib. In some embodiments, Cabozantinib is administered orally at a dose of about 40 mg per day to about 100 mg per day.

In some embodiments, the kinase inhibitor is an EGFR, MEK, or SRC kinase inhibitor. In some embodiments, the kinase inhibitor is Erlotinib, Cetuximab, Gefitinib, Canertinib, Panitumumab, Nimotuzumab, Lapatinib, Vandetanib, Afatinib, MP-412, AEE-788, Neratinib, XL-647, AC-480, Dacomitinib, AZD-8931, CUDC-101, AP-26113, CO-1686, Trametinib, Selumetinib, MEK-162, Refametinib, TAK-733, RO-5126766, BI-847325, AZD6244, GSK1120212, PF-5208763 (Bosutinib), or AZD-0530 (Saracatinib).

In some embodiments, the kinase inhibitor is Erlotinib. In some embodiments, Erlotinib is administered orally at a dose of about 100 mg to about 150 mg.

In some embodiments, the kinase inhibitor is Gefitinib. In some embodiments, Gefitinib is administered orally at a dose of about 250 mg.

In some embodiments, the kinase inhibitor is Trametinib. In some embodiments, Trametinib is administered orally at a dose of about 1 mg to about 2 mg.

In some embodiments, the kinase inhibitor is a AKT, RAF, FGFR, or CDK4/6 kinase inhibitor. In some embodiments, the kinase inhibitor is GDC0068, MK-2206, AT7867, GSK2110183, GSK2141795, GSK690693, Vemurafenib (PLX4032/RG7204), GSK2118436, Dabrafenib (GSK208436), LGX818, RAF265, LY2780301, Dovitinib (TKI258), BGJ398, AZD4547, PD-0332991 or LEE011.

In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally at a dose of about 120 mg per day to about 240 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally at a dose of about 240 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally in the form of a softgel capsule.

Combination with Immunotherapy

Augmentation of cytotoxic T-cell responses is the cornerstone of most immunotherapies. Androgen ablation has been shown to result in modulation of immune function which in turn could further augment tumor targeted immune therapy. These effects include, but are not limited to: Increased CD4+ T cell infiltration into the prostate gland; Increased in CD8+ T cell and macrophage number in the prostate gland; Increased thymic production of T cells and overall enhancement of immunotherapy in various animal models. In some embodiments, combination of a second generation anti-androgen (on top of androgen ablation) could further increase the androgen ablation induced immunological effects increasing the efficacy of the immunotherapy. In addition, given that immunotherapies function via the cytotoxic T cell response resulting in induction of tumor cell apoptosis, the proapoptotic activity of a second generation anti-androgen should lower the apoptotic threshold of the immunotherapy based T-cell responses In one aspect, described herein is a method of treating prostate cancer in a male human comprising administering a second generation anti-androgen to a male human with metastatic castration-resistant prostate cancer, non-metastatic castration-resistant prostate cancer, metastatic castration-sensitive prostate cancer, non-metastatic castration-sensitive prostate cancer or high-risk localized prostate cancer in combination with PROVENGE™ (sipuleucel-T), PROSTVAC™ (rilimogene galvacirepvec/rilimogene glafolivec), Ipilimumab, or a PD-1 inhibitor. In some embodiments, the second generation anti-androgen is MDV-3100 or 4-[7-(6-cyano-5-trifluoromethylpyridin-3-yl)-8-oxo-6-thioxo-5,7-diazaspiro[3.4]oct-5-yl]-2-fluoro-N-methylbenzamide. In some embodiments, the second generation anti-androgen is MDV-3100. In some embodiments, the second generation anti-androgen is 4-[7-(6-cyano-5-trifluoromethylpyridin-3-yl)-8-oxo-6-thioxo-5,7-diazaspiro[3.4]oct-5-yl]-2-fluoro-N-methylbenzamide.

In one aspect, described herein is a method of treating prostate cancer in a male human comprising administering 4-[7-(6-cyano-5-trifluoromethylpyridin-3-yl)-8-oxo-6-thioxo-5,7-diazaspiro[3.4]oct-5-yl]-2-fluoro-N-methylbenzamide at a dose of about 30 mg per day to about 480 mg per day to a male human with metastatic castration-resistant prostate cancer, non-metastatic castration-resistant prostate cancer, metastatic castration-sensitive prostate cancer, non-metastatic castration-sensitive prostate cancer or high-risk localized prostate cancer in combination with PROVENGE™ (sipuleucel-T), Prostvac, Ipilimumab, or a PD-1 inhibitor.

In some embodiments, the method of treating prostate cancer further comprises administering a therapeutically effective amount of a gonadotropin-releasing hormone agonist or antagonist to the male human.

In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered in combination with Ipilimumab. In some embodiments, Ipilimumab is administered by intravenous infusion at a dose of about 1.5 mg/Kg to about 3.0 mg/kg IV every 3 weeks for a total of 4 doses.

In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered in combination with PD-1 inhibitor. In some embodiments, the PD-1 inhibitor is BMS-936558. In some embodiments, the PD-1 inhibitor is BMS-936558 and is administered by intravenous infusion at a dose of about 1.0 mg/kg to about 10 mg/kg on days 1, 15 and 29 of 6-week cycles.

In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered in combination with PROVENGE™ (sipuleucel-T). In some embodiments, 3 doses of PROVENGE™ (sipuleucel-T) are administered doses at approximately 2 weeks interval.

In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered in combination with Prostvac. In some embodiments, PROSTVAC™ (rilimogene galvacirepvec/rilimogene glafolivec) is administered by subcutaneous injection.

In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally at a dose of about 120 mg per day to about 240 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally at a dose of about 240 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally in the form of a softgel capsule.

Combination with a Taxane or Tubulin Inhibitor

Taxanes such as Docetaxel and Cabazitaxel are anti-mitotic drugs that inhibit tumor cell proliferation and also induce tumor cell apoptosis. In some embodiments, the combination of a second generation anti-androgen with a taxane or tubulin inhibitor increases increases apoptotic and antiproliferative response in CRPC resulting in an increase in antitumor response to the therapy.

In one aspect, described herein is a method of treating prostate cancer in a male human comprising administering a second generation anti-androgen to a male human with metastatic castration-resistant prostate cancer, or high-risk localized prostate cancer in combination with a taxane or tubulin inhibitor. In some embodiments, the second generation anti-androgen is MDV-3100 or 4-[7-(6-cyano-5-trifluoromethylpyridin-3-yl)-8-oxo-6-thioxo-5,7-diazaspiro[3.4]oct-5-yl]-2-fluoro-N-methylbenzamide. In some embodiments, the second generation anti-androgen is MDV-3100. In some embodiments, the second generation anti-androgen is 4-[7-(6-cyano-5-trifluoromethylpyridin-3-yl)-8-oxo-6-thioxo-5,7-diazaspiro[3.4]oct-5-yl]-2-fluoro-N-methylbenzamide.

In one aspect, described herein is a method of treating prostate cancer in a male human comprising administering 4-[7-(6-cyano-5-trifluoromethylpyridin-3-yl)-8-oxo-6-thioxo-5,7-diazaspiro[3.4]oct-5-yl]-2-fluoro-N-methylbenzamide at a dose of about 30 mg per day to about 480 mg per day to a male human with metastatic castration-resistant prostate cancer, or high-risk localized prostate cancer in combination with a taxane or tubulin inhibitor.

In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered in combination with Docetaxel. In some embodiments, Docetaxel is administered by intravenous infusion at a dose of about 35 mg/m$^2$ to about 75 mg/m$^2$ every 3 weeks.

In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered in combination with Cabazitaxel. In some embodiments, Cabazitaxel is administered by intravenous infusion at a dose of about 13 mg/m$^2$ to about 25 mg/m$^2$ every 3 weeks.

In some embodiments, the method of treating prostate cancer further comprises administering a therapeutically effective amount of a gonadotropin-releasing hormone agonist or antagonist to the male human.

In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally at a dose of about 120 mg per day to about 240 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally at a dose of about 240 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally in the form of a softgel capsule.

Combination with an Anti-STEAP-1 Antibody Drug Conjugate

An anti-STEAP1 antibody drug conjugate (ADC) selectively delivers an anti-mitotic agent to prostate cells expressing STEAP1. This results in a tumor selective increase in tumor cell apoptosis.

In one aspect, described herein is a method of treating prostate cancer in a male human comprising administering a second generation anti-androgen to a male human with metastatic castration-resistant prostate cancer, non-metastatic castration-resistant prostate cancer, metastatic castration-sensitive prostate cancer, non-metastatic castration-sensitive prostate cancer or high-risk localized prostate cancer in combination with an anti-STEAP-1 antibody drug conjugate. In some embodiments, the second generation anti-androgen is MDV-3100 or 4-[7-(6-cyano-5-trifluoromethylpyridin-3-yl)-8-oxo-6-thioxo-5,7-diazaspiro[3.4]oct-5-yl]-2-fluoro-N-methylbenzamide. In some embodiments, the second generation anti-androgen is MDV-3100. In some embodiments, the second generation anti-androgen is 4-[7-(6-cyano-5-trifluoromethylpyridin-3-yl)-8-oxo-6-thioxo-5,7-diazaspiro[3.4]oct-5-yl]-2-fluoro-N-methylbenzamide.

In one aspect, described herein is a method of treating prostate cancer in a male human comprising administering 4-[7-(6-cyano-5-trifluoromethylpyridin-3-yl)-8-oxo-6-thioxo-5,7-diazaspiro[3.4]oct-5-yl]-2-fluoro-N-methylbenzamide at a dose of about 30 mg per day to about 480 mg per day to a male human with metastatic castration-resistant prostate cancer, non-metastatic castration-resistant prostate cancer, metastatic castration-sensitive prostate cancer, non-metastatic castration-sensitive prostate cancer or high-risk localized prostate cancer in combination with an anti-STEAP-1 antibody drug conjugate.

In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered in combination with an anti-STEAP-1 antibody drug conjugate. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered in combination with RG7450 (DSTP3086S).

In some embodiments, the method of treating prostate cancer further comprises administering a therapeutically effective amount of a gonadotropin-releasing hormone agonist or antagonist to the male human.

In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally at a dose of about 120 mg per day to about 240 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally at a dose of about 240 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally in the form of a softgel capsule.

Combination with a HSP Inhibitor

The heat shock protein family is a critical regulator tumor cell growth and survival via its regulation of client protein function. These client proteins include oncoproteins such as HER2 and Raf as well the androgen receptor (AR), all of which are key drivers of prostate cancer growth and survival.

In some embodiments, combination therapy of a HSP90/HSP27 (OGX-427) inhibitor with a second generation anti-androgen results in inhibition of the AR signaling pathway at 2 distinct nodes and thus has potential to increase therapeutic outcomes across the spectrum of CRPC.

In one aspect, described herein is a method of treating prostate cancer in a male human comprising administering a second generation anti-androgen to a male human with metastatic castration-resistant prostate cancer, non-metastatic castration-resistant prostate cancer, metastatic castration-sensitive prostate cancer, non-metastatic castration-sensitive prostate cancer or high-risk localized prostate cancer in combination with a heat shock protein 90 (HSP90) or heat shock protein 27 (HSP27) pathway modulator. In some embodiments, the second generation anti-androgen is MDV-3100 or 4-[7-(6-cyano-5-trifluoromethylpyridin-3-yl)-8-oxo-6-thioxo-5,7-diazaspiro[3.4]oct-5-yl]-2-fluoro-N-methylbenzamide. In some embodiments, the second generation anti-androgen is MDV-3100. In some embodiments, the second generation anti-androgen is 4-[7-(6-cyano-5-trifluoromethylpyridin-3-yl)-8-oxo-6-thioxo-5,7-diazaspiro[3.4]oct-5-yl]-2-fluoro-N-methylbenzamide.

In one aspect, described herein is a method of treating prostate cancer in a male human comprising administering 4-[7-(6-cyano-5-trifluoromethylpyridin-3-yl)-8-oxo-6-thioxo-5,7-diazaspiro[3.4]oct-5-yl]-2-fluoro-N-methylbenzamide at a dose of about 30 mg per day to about 480 mg per day to a male human with metastatic castration-resistant prostate cancer, non-metastatic castration-resistant prostate cancer, metastatic castration-sensitive prostate cancer, non-metastatic castration-sensitive prostate cancer or high-risk localized prostate cancer in combination with a heat shock protein 90 (HSP90) or heat shock protein 27 (HSP27) pathway modulator.

In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered in combination with OGX-011 (Custirsen), OGX-427, AUY922, HSP990, PF-04928473, PF-04929113 (SNX-5422), Retaspimycin or AT13387.

In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered in combination with OGX-011 (Custirsen). In some embodiments, OGX-011 (Custirsen) is administered by intravenous infusion at a dose of about 320 mg to about 640 mg every week.

In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered in combination with OGX-427. In some embodiments, OGX-427 is administered by intravenous infusion at a loading dose of about 300 mg to about 600 mg followed by about 500 mg to about 1000 mg every week.

In some embodiments, the method of treating prostate cancer further comprises administering a therapeutically effective amount of a gonadotropin-releasing hormone agonist or antagonist to the male human.

In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally at a dose of about 120 mg per day to about 240 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally at a dose of about 240 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally in the form of a softgel capsule.

Other Combination Strategies

In one aspect, disclosed herein is the use of 4-[7-(6-cyano-5-trifluoromethylpyridin-3-yl)-8-oxo-6-thioxo-5,7-diazaspiro[3.4]oct-5-yl]-2-fluoro-N-methylbenzamide in the treatment of breast cancer in a human in combination with at least one additional treatment option for the breast cancer. In some embodiments, the at least one additional treatment option comprises breast cancer surgery. In some embodiments, breast cancer surgery comprises lumpectomy, mastectomy, sentinel node biopsy, or axillary node dissection. In some embodiments, the at least one additional treatment option comprises radiation therapy. In some embodiments, radiation comprises external beam radiation or brachytherapy. In some embodiments, the at least one additional treatment option comprises hormone therapy (i.e. hormone blocking therapy). In some embodiments, hormone therapy comprises the use of a selective estrogen receptor modulator (SERM) (e.g. tamoxifen), aromatase inhibitor (e.g. anastrozole (Arimidex), letrozole (Femara) and exemestane (Aromasin)), or fulvestrant (Faslodex). In some embodiments, the at least one additional treatment option comprises surgery to remove the ovaries or medications to stop the ovaries from making estrogen. In some embodiments, the at least one additional treatment option comprises the use of trastuzumab (Herceptin), lapatinib (Tykerb), or bevacizumab (Avastin). In some embodiments, the at least one additional treatment option comprises the use of bone-building drugs to prevent breast cancer recurrence (e.g. zoledronic acid (Reclast, Zometa)).

In one aspect, disclosed herein is the use of 4-[7-(6-cyano-5-trifluoromethylpyridin-3-yl)-8-oxo-6-thioxo-5,7-diazaspiro[3.4]oct-5-yl]-2-fluoro-N-methylbenzamide in the treatment of uterine fibroids in a human in combination with at least one additional treatment option for the uterine fibroids. In some embodiments, the at least one additional treatment option comprises the use of a gonadotropin-releasing hormone (GnRH) agonist or antagonist, a progestin-releasing intrauterine device (IUD), an androgen, nonsteroidal anti-inflammatory drug (NSAIDs), a hysterectomy, or a myomectomy.

In one aspect, disclosed herein is the use of 4-[7-(6-cyano-5-trifluoromethylpyridin-3-yl)-8-oxo-6-thioxo-5,7-diazaspiro[3.4]oct-5-yl]-2-fluoro-N-methylbenzamide in the treatment of endometriosis in a human in combination with at least one additional treatment option for the endometriosis. In some embodiments, the at least one additional treatment option comprises the use of pain medications, and/or hormone therapies. In some embodiments, hormone therapies comprise hormonal contraceptives, gonadotropin-releasing hormone (GnRH) agonists and antagonists, Danazol, medroxyprogesterone (Depo-Provera) and aromatase inhibitors.

Kits/Articles of Manufacture

For use in the therapeutic methods of use described herein, kits and articles of manufacture are also described herein. Such kits include a package or container that is compartmentalized to receive one or more dosages of the pharmaceutical compositions disclosed herein. Suitable containers include, for example, bottles. In one embodiment, the containers are formed from a variety of materials such as glass or plastic.

The articles of manufacture provided herein contain packaging materials. Packaging materials for use in packaging pharmaceutical products include, e.g., U.S. Pat. Nos. 5,323,907, 5,052,558 and 5,033,252. Examples of pharmaceutical packaging materials include, but are not limited to, blister packs, bottles, tubes, bags, containers, bottles, and any packaging material suitable for a selected formulation and intended mode of administration and treatment.

A kit typically includes labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

In certain embodiments, the pharmaceutical compositions are presented in a pack or dispenser device which contains one or more unit dosage forms containing a compound provided herein. The pack, for example, contains metal or plastic foil, such as a blister pack. In one embodiment, the pack or dispenser device is accompanied by instructions for administration. In one embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In one embodiment, compositions containing a compound provided herein formulated in a compatible pharmaceutical carrier are also prepared, placed in an appropriate container, and labeled for treatment of an indicated condition.

Biomarkers

In some embodiments, efficacy of treatment with a second generation anti-androgen (e.g 4-[7-(6-cyano-5-trifluoromethylpyridin-3-yl)-8-oxo-6-thioxo-5,7-diazaspiro[3.4]oct-5-yl]-2-fluoro-N-methylbenzamide) is assessed by monitoring any one of the following: circulating tumor cell's (CTC's); [18F]-fluorodihydrotestosterone-positron emission tomography (FDHT-PET); PSA kinetics; AR target gene modulation in primary tumor (neoadjuvent/presurgical studies), tumor biopsies and in CTCs; Ki67, TUNEL and other markers of proliferation and apoptosis in primary tumor (neoadjuvent/presurgical studies), tumor biopsies and in CTCs; transmembrane protease, serine 2 (TMPRSS2)-v-ets erythroblastosis virus E26 oncogene homolog (ERG) fusion (TMPRSS2: ERG fusion); or any of the preceding in primary tumor upon radical prostatectomy or in CT-guided biopsies.

In some embodiments, enumeration of circulating tumor cell's (CTC's) themselves are a biomarker and maybe predictive of outcome. The number of CTC at baseline and change over time from unfavorable (≥5 CTCs/7.5 ml of blood) to favorable (<5 CTCs/7.5 ml of blood) has been shown to be correlated with statistically improved survival in patient with metastatic CRPC. The number of CTCs at baseline has also been associated with risk of death. The higher the number of CTCs at baseline correlates with higher risk of dying from prostate cancer. In some embodiments, using CTC's to determine PTEN/PI3K, PHLPP1, or AR status, is used to stratify patients as well as an indication of outcome. In some embodiments, interrogating CTCs for genetic alterations is feasible. In some embodiments, assessing PTEN/PI3K and or AR status at baseline has the potential to personalize treatment plan for a patient with metastatic prostate cancer by designing a proper combination therapy (e.g. with PI3K inhibitor in patients with PTEN loss in the tumor) or choosing other treatment for patients with AR alterations that render them unlikely to respond to the a second generation anti-androgen (e.g. 4-[7-(6-cyano-5-trifluoromethylpyridin-3-yl)-8-oxo-6-thioxo-5,7-diazaspiro[3.4]oct-5-yl]-2-fluoro-N-methylbenzamide).

FDHT-PET has been shown to be a useful pharmacodynamic biomarker for antiandrogen drugs. In some embodiments, it can guide as to the minimal dose level that will result in a robust androgen blockade by a second generation anti-androgen (e.g. 4-[7-(6-cyano-5-trifluoromethylpyridin-3-yl)-8-oxo-6-thioxo-5,7-diazaspiro[3.4]oct-5-yl]-2-fluoro-N-methylbenzamide).

Similar to CTCs, changes in PSA kinetics during treatment of prostate cancer may be a prognostic factor for clinical benefit. Men with metastatic prostate cancer with PSA levels of 4 ng/ml or less after 7 months on hormonal therapy have been shown to have longer survival and 30% PSA decline at 3 months of chemotherapy has been associated with better survival.

The following listing of embodiments in intended to complement, rather than displace or supersede, the previous descriptions.

Embodiment 1

A method of treating advanced prostate cancer in a male human comprising administering 4-[7-(6-cyano-5-trifluoromethylpyridin-3-yl)-8-oxo-6-thioxo-5,7-diazaspiro[3.4]oct-5-yl]-2-fluoro-N-methylbenzamide (I), or a pharmaceutically acceptable salt thereof, at a dose of about 30 mg per day to about 480 mg per day to a male human with castration-sensitive prostate cancer, castration-resistant prostate cancer, or high-risk localized prostate cancer.

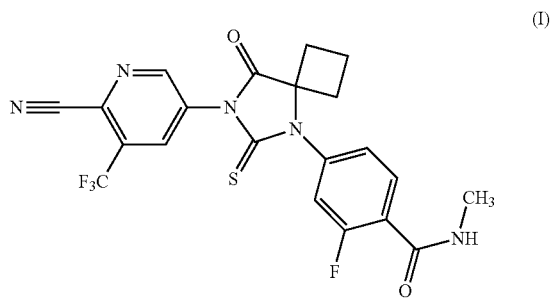 [SMILES: CNC(=O)c1ccc(N2C(=S)N(c3cnc(C#N)c(C(F)(F)F)c3)C(=O)C23CCC3)cc1F]

(I)

Embodiment 2

The method of Embodiment 1, wherein the castration-resistant prostate cancer is metastatic castration-resistant prostate cancer.

Embodiment 3

The method of Embodiment 2, wherein the metastatic castration-resistant prostate cancer is chemotherapy naïve metastatic castration-resistant prostate cancer or post-abiraterone acetate treated metastatic castration-resistant prostate cancer.

Embodiment 4

A method of decreasing prostate-specific antigen levels in a male human with advanced prostate cancer comprising administering 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, at a dose of about 30 mg per day to about 480 mg per day to the male human with castration-sensitive prostate cancer, castration-resistant prostate cancer, or high-risk localized prostate cancer.

Embodiment 5

The method of Embodiment 4, wherein the prostate-specific antigen levels in the male human are decreased by at least 50% from baseline after 3 months of administering 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, on a continuous daily dosing schedule.

Embodiment 6

A method of treating breast cancer, androgen dependent hirsutism, androgenic alopecia, uterine fibroids, leiomyoma, endometrial carcinoma or endometriosis in a human comprising administering 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, at a dose of about 30 mg per day to about 480 mg per day to a human with breast cancer, androgen dependent hir-

47 sutism, androgenic alopecia, uterine fibroids, leiomyoma, endometrial carcinoma or endometriosis.

Embodiment 7

The method of any one of Embodiments 1 to 6, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, is administered orally to the human in the form of soft-gel capsules.

Embodiment 8

The method of any one of Embodiments 1 to 7, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, is administered orally to the human in the form of soft-gel capsules at a dose of about 180 mg per day to about 480 mg per day.

Embodiment 9

The method of any one of Embodiments 1 to 8, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, is administered orally to the human in the form of soft-gel capsules at a dose of about 180 mg per day, about 240 mg per day, about 300 mg per day, about 390 mg per day, or about 480 mg per day.

Embodiment 10

The method of any one of Embodiments 1 to 8, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, is administered orally to the human in the form of soft-gel capsules at a dose of about 240 mg per day.

Embodiment 11

The method of any one of Embodiments 7 to 10, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, is administered orally to the human on a continuous daily dosing schedule.

Embodiment 12

A method of treating prostate cancer in a male human comprising administering 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, at a dose of about 30 mg per day to about 480 mg per day to a male human with post-abiraterone acetate treated metastatic castration-resistant prostate cancer, metastatic castration-resistant prostate cancer, non-metastatic castration-resistant prostate cancer, metastatic castration-sensitive prostate cancer, non-metastatic castration-sensitive prostate cancer or high-risk localized prostate cancer in combination with a phosphoinositide 3-kinase (PI3K) inhibitor, TORC inhibitor, or dual PI3K/TORC inhibitor.

48

Embodiment 13

The method of Embodiment 12, further comprising administering a therapeutically effective amount of a gonadotropin-releasing hormone agonist or antagonist to the male human.

Embodiment 14

The method of Embodiment 12 or Embodiment 13, wherein the phosphoinositide 3-kinase (PI3K) inhibitor, TORC inhibitor, or dual PI3K/TORC inhibitor is everolimus, BEZ-235, BKM120, BGT226, BYL-719, GDC0068, GDC-0980, GDC0941, GDC0032, MK-2206, OSI-027, CC-223, AZD8055, SAR245408, SAR245409, PF04691502, WYE125132, GSK2126458, GSK-2636771, BAY806946, PF-05212384, SF1126, PX866, AMG319, ZSTK474, Cal101, PWT33597, LY-317615 (enzastaurin hydrochloride), CU-906, or CUDC-907.

Embodiment 15

The method of any one of Embodiments 12 to 14, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, is administered orally at a dose of about 120 mg per day to about 240 mg per day.

Embodiment 16

The method of any one of Embodiments 12 to 15, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, is administered orally at a dose of about 240 mg per day.

Embodiment 17

The method of any one of Embodiments 12 to 16, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, is administered orally in the form of a softgel capsule.

Embodiment 18

The method of any one of Embodiments 12 to 17, wherein the TORC inhibitor is everolimus.

Embodiment 19

The method of Embodiment 18, wherein everolimus is administered at a dose of about 5 mg per day to about 20 mg per day.

Embodiment 20

The method of Embodiment 18, wherein everolimus is administered at a dose of about 5 mg per day or about 10 mg per day.

Embodiment 21

A method of treating prostate cancer in a male human comprising administering 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, at a dose of about 30 mg per day to about 480 mg per day to a male human with metastatic castration-resistant prostate cancer, non-metastatic castration-resistant prostate cancer, metastatic castration-sensitive prostate cancer, non-metastatic castration-sensitive prostate cancer or high-risk localized prostate cancer in combination with a CYP17 inhibitor.

Embodiment 22

The method of Embodiment 21, further comprising administering a therapeutically effective amount of a gonadotropin-releasing hormone agonist or antagonist to the male human.

Embodiment 23

The method of Embodiment 21 or Embodiment 22, wherein the CYP17 inhibitor is abiraterone acetate (Zytiga), TAK-700 (orteronel), TOK-001 (galeterone) or VT-464.

Embodiment 24

The method of any one of Embodiments 21 to 23, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, is administered orally at a dose of about 120 mg per day to about 240 mg per day.

Embodiment 25

The method of any one of Embodiments 21 to 24, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, is administered orally at a dose of about 240 mg per day.

Embodiment 26

The method of any one of Embodiments 21 to 25, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, is administered orally in the form of a softgel capsule.

Embodiment 27

The method of any one of Embodiment 21 to 26, wherein the CYP17 inhibitor is abiraterone acetate (Zytiga).

Embodiment 28

The method of Embodiment 27, wherein abiraterone acetate (Zytiga) is administered at a dose of about 500 mg per day to about 1000 mg per day together with prednisone at a dose of about 5 mg twice per day.

Embodiment 29

The method of Embodiment 28, wherein abiraterone acetate (Zytiga) is administered at a dose of about 1000 mg per day.

Embodiment 30

The method of any one of Embodiment 21 to 26, wherein the CYP17 inhibitor is TAK-700 (orteronel).

Embodiment 31

The method of Embodiment 30, TAK-700 (orteronel) is administered at a dose of about 300 mg twice per day to about 600 mg twice per day.

Embodiment 32

The method of Embodiment 30 or Embodiment 31, where TAK-700 (orteronel) is administered at a dose of about 300 mg twice per day to about 600 mg twice per day, together with prednisone at about 5 mg twice per day Embodiment 33

A method of treating prostate cancer in a male human comprising administering 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, at a dose of about 30 mg per day to about 480 mg per day to a male human with metastatic castration-resistant prostate cancer, non-metastatic castration-resistant prostate cancer, metastatic castration-sensitive prostate cancer, non-metastatic castration-sensitive prostate cancer or high-risk localized prostate cancer in combination with a gonadotropin-releasing hormone agonist or antagonist.

Embodiment 34

The method of Embodiment 33, wherein the gonadotropin-releasing hormone agonist or antagonist is Lupron, Zoladex (Goserelin), Degarelix, Ozarelix, ABT-620 (Elagolix), TAK-385 (Relugolix), EP-100 or KLH-2109.

Embodiment 35

The method of Embodiment 33 or Embodiment 34, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, is administered orally at a dose of about 120 mg per day to about 240 mg per day.

Embodiment 36

The method of any one of Embodiments 33 to 35, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, is administered orally at a dose of about 240 mg per day.

Embodiment 37

The method of any one of Embodiments 33 to 36, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, is administered orally in the form of a softgel capsule.

Embodiment 38

The method of any one of Embodiments 33 to 37, wherein the gonadotropin-releasing hormone agonist or antagonist is Lupron.

Embodiment 39

The method of Embodiment 38, wherein Lupron is administered as a depot injection at a dose of about 7.5 mg every 4

Embodiment 40

The method of any one of Embodiments 33 to 37, wherein the gonadotropin-releasing hormone agonist or antagonist is Zoladex (Goserelin).

Embodiment 41

The method of Embodiment 40, wherein Zoladex (Goserelin) is administered as a subcutaneous implant at a dose of about 3.6 mg every 4 weeks or about 10.8 mg every 12 weeks.

Embodiment 42

The method of any one of Embodiment 33 to 37, wherein the gonadotropin-releasing hormone agonist or antagonist is Degarelix.

Embodiment 43

The method of Embodiment 42, wherein Degarelix is administered as a subcutaneous injection at a dose of about 240 mg followed by about 80 mg administered every 4 weeks.

Embodiment 44

A method of treating prostate cancer in a male human comprising administering 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, at a dose of about 30 mg per day to about 480 mg per day to a male human with metastatic castration-resistant prostate cancer, non-metastatic castration-resistant prostate cancer, metastatic castration-sensitive prostate cancer, non-metastatic castration-sensitive prostate cancer or high-risk localized prostate cancer in combination with an osteoprotective agent.

Embodiment 45

The method of Embodiment 44, further comprising administering a therapeutically effective amount of a gonadotropin-releasing hormone agonist or antagonist to the male human.

Embodiment 46

The method of Embodiment 44 or Embodiment 45, wherein the osteoprotective agent is Denosumab, AMG-0007, CEP-37251, ALX-0141, Zoledronic acid, Alendronate sodium (Fosamax), Pamidronate disodium (Aredia), Neridronic acid (Nerixia), Minodronic acid (Recalbon) or Risedronate sodium (Actonel).

Embodiment 47

The method of any one of Embodiments 44 to 46, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, is administered orally at a dose of about 120 mg per day to about 240 mg per day.

Embodiment 48

The method of any one of Embodiments 44 to 47, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, is administered orally at a dose of about 240 mg per day.

Embodiment 49

The method of any one of Embodiment 44 to 48, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, is administered orally in the form of a softgel capsule.

Embodiment 50

The method of any one of Embodiment 44 to 49, wherein the osteoprotective agent is Denosumab.

Embodiment 51

The method of Embodiment 50, wherein Denosumab is administered by subcutaneous injection at a dose of about 60 mg to about 120 mg every 4 weeks to every 6 months.

Embodiment 52

The method of any one of Embodiment 44 to 49, wherein the osteoprotective agent is Zoledronic acid.

Embodiment 53

The method of Embodiment 52, wherein Zoledronic acid is administered by intravenous infusion at a dose of about 4 mg every 4 weeks to every 12 weeks.

Embodiment 54

A method of treating prostate cancer in a male human comprising administering 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, at a dose of about 30 mg per day to about 480 mg per day to a male human with metastatic castration-resistant prostate cancer, non-metastatic castration-resistant prostate cancer, metastatic castration-sensitive prostate cancer, non-metastatic castration-sensitive prostate cancer or high-risk localized prostate cancer in combination with a radiation therapy.

Embodiment 55

The method of Embodiment 54, further comprising administering a therapeutically effective amount of a gonadotropin-releasing hormone agonist or antagonist to the male human.

Embodiment 56

The method of Embodiment 54 or Embodiment 55, wherein the radiation therapy is Alpharadin, $^{177}$Lu-J591, external beam radiation therapy (including Proton beam), or brachytherapy.

Embodiment 57

The method of any one of Embodiment 54 to 56, wherein 4-[7-(6-cyano-5-trifluoromethylpyridin-3-yl)-8-oxo-6-thioxo-5,7-diazaspiro[3.4]oct-5-yl]-2-fluoro-N-methylben-

Embodiment 58

The method of any one of Embodiment 54 to 57, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, is administered orally at a dose of about 240 mg per day.

Embodiment 59

The method of any one of Embodiment 54 to 58, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, is administered orally in the form of a softgel capsule.

Embodiment 60

The method of any one of Embodiments 54 to 59, wherein the radiation therapy is Alpharadin.

Embodiment 61

The method of claim 60, wherein Alpharadin is administered by intravenous infusion at a dose of about 25 to about 50 kBq/kg every 4 weeks.\

Embodiment 62

The method of any one of Embodiment 54 to 59, wherein the radiation therapy is $^{177}$Lu-J591.

Embodiment 63

The method of Embodiment 62, wherein $^{177}$Lu-J591 is administered by intravenous infusion at a dose of about 30 mCi/m$^2$ to about 70 mCi/m$^2$.

Embodiment 64

A method of treating prostate cancer in a male human comprising administering 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, at a dose of about 30 mg per day to about 480 mg per day to a male human with post-abiraterone acetate treated metastatic castration-resistant prostate cancer, metastatic castration-resistant prostate cancer, non-metastatic castration-resistant prostate cancer, metastatic castration-sensitive prostate cancer, non-metastatic castration-sensitive prostate cancer or high-risk localized prostate cancer in combination with a kinase inhibitor.

Embodiment 65

The method of Embodiment 64, further comprising administering a therapeutically effective amount of a gonadotropin-releasing hormone agonist or antagonist to the male human.

Embodiment 66

The method of any one of Embodiment 64 or Embodiment 65, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, is administered orally at a dose of about 120 mg per day to about 240 mg per day.

Embodiment 67

The method of any one of Embodiments 64 to 66, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, is administered orally at a dose of about 240 mg per day.

Embodiment 68

The method of any one of Embodiments 64 to 67, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, is administered orally in the form of a softgel capsule.

Embodiment 69

The method of any one of Embodiments 64 to 68, wherein the kinase inhibitor targets angiogenesis or bone metastases.

Embodiment 70

The method of any one of Embodiments 64 to 69, wherein the kinase inhibitor is a MET or VEGFR kinase inhibitor.

Embodiment 71

The method of Embodiment 70, wherein the kinase inhibitor is Cabozantinib (XL184), PF-2341066 (Crizotinib), ARQ-197 (Tivantinib), MK-2461, JNJ-38877605, MK-8033, INCB-28060, BMS-777607, AMG-208, LY-2801653, EMD-1214063, EMD-1204831, AMG-337, HMPL-504 (Volitinib), SAR-125844, LY2875358, ABR-215050 (Tasquinimod), CHIR-258 (Dovitinib), EXEL-7647, OSI-930, BIBF-1120, BAY-73-4506 (Regorafenib), BMS-582664 (Brivanib), JNJ-26483327, AZD-2171 (Cediranib), Sorafenib, Aflibercept, Enzastaurin, AG-013736 (Axitinib), OSI-632, or GSK-786034 (Pazopanib).

Embodiment 72

The method of any one of Embodiment 64 to 71, wherein the kinase inhibitor is Cabozantinib.

Embodiment 73

The method of Embodiment 72, wherein Cabozantinib is administered orally at a dose of about 40 mg per day to about 100 mg per day.

Embodiment 74

The method of any one of Embodiment 64 to 69, wherein the kinase inhibitor is an EGFR, MEK, or SRC kinase inhibitor.

Embodiment 75

The method of Embodiment 74, wherein the kinase inhibitor is Erlotinib, Cetuximab, Gefitinib, Canertinib, Panitumumab, Nimotuzumab, Lapatinib, Vandetanib, Afatinib, MP-412, AEE-788, Neratinib, XL-647, AC-480, Dacomitinib, AZD-8931, CUDC-101, AP-26113, CO-1686, Trametinib, Selumetinib, MEK-162, Refametinib, TAK-733, RO-5126766, BI-847325, AZD6244, GSK1120212, PF-5208763 (Bosutinib), or AZD-0530 (Saracatinib).

Embodiment 76

The method of any one of Embodiments 64 to 69, 74 or 75, wherein the kinase inhibitor is Erlotinib.

Embodiment 77

The method of Embodiment 76, wherein Erlotinib is administered orally at a dose of about 100 mg to about 150 mg.

Embodiment 78

The method of any one of Embodiments 64 to 69, 74 or 75, wherein the kinase inhibitor is Gefitinib.

Embodiment 79

The method of Embodiment 78, wherein Gefitinib is administered orally at a dose of about 250 mg.

Embodiment 80

The method of any one of Embodiments 64 to 69, 74 or 75, wherein the kinase inhibitor is Trametinib.

Embodiment 81

The method of Embodiment 80, wherein Trametinib is administered orally at a dose of about 1 mg to about 2 mg.

Embodiment 82

The method of any one of Embodiment 64 to 69, wherein the kinase inhibitor is an AKT, RAF, FGFR, or CDK4/6 kinase inhibitor.

Embodiment 83

The method of Embodiment 82, wherein the kinase inhibitor is GDC0068, MK-2206, AT7867, GSK2110183, GSK2141795, GSK690693, Vemurafenib (PLX4032/RG7204), GSK2118436, Dabrafenib (GSK208436), LGX818, RAF265, LY2780301, Dovitinib (TKI258), BGJ398, AZD4547, PD-0332991 or LEE011.

Embodiment 84

A method of treating prostate cancer in a male human comprising administering 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, at a dose of about 30 mg per day to about 480 mg per day to a male human with metastatic castration-resistant prostate cancer, non-metastatic castration-resistant prostate cancer, metastatic castration-sensitive prostate cancer, non-metastatic castration-sensitive prostate cancer or high-risk localized prostate cancer in combination with PROVENGE™ (sipuleucel-T), Prostvac, Ipilimumab, or a PD-1 inhibitor.

Embodiment 85

The method of Embodiment 84, further comprising administering a therapeutically effective amount of a gonadotropin-releasing hormone agonist or antagonist to the male human.

Embodiment 86

The method of any one of Embodiment 84 or Embodiment 85, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, is administered orally at a dose of about 120 mg per day to about 240 mg per day.

Embodiment 87

The method of any one of Embodiment 84 to 86, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, is administered orally at a dose of about 240 mg per day.

Embodiment 88

The method of any one of Embodiment 84 to 87, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, is administered orally in the form of a softgel capsule.

Embodiment 89

The method of any one of Embodiment 84 to 88, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, is administered in combination with Ipilimumab.

Embodiment 90

The method of Embodiment 89, wherein Ipilimumab is administered by intravenous infusion at a dose of about 1.5 mg/Kg to about 3.0 mg/kg IV every 3 weeks for a total of 4 doses.

Embodiment 91

The method of any one of Embodiment 84 to 88, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, is administered in combination with a PD-1 inhibitor.

Embodiment 92

The method of Embodiment 91, wherein the PD-1 inhibitor is BMS-936558 and is administered by intravenous infusion at a dose of about 1.0 mg/kg to about 10 mg/kg on days 1, 15 and 29 of 6-week cycles.

Embodiment 93

The method of any one of Embodiment 84 to 88, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, is administered in combination with PROVENGE™ (sipuleucel-T).

Embodiment 94

The method of Embodiment 93, wherein 3 doses of PROVENGE™ (sipuleucel-T) are administered doses at approximately 2 weeks interval.

Embodiment 95

The method of any one of Embodiment 84 to 88, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, is administered in combination with PROSTVAC™ (rilimogene galvacirepvec/rilimogene glafolivec).

Embodiment 96

The method of Embodiment 95, wherein PROSTVAC™ (rilimogene galvacirepvec/rilimogene glafolivec) is administered by subcutaneous injection.

Embodiment 97

A method of treating prostate cancer in a male human comprising administering 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, at a dose of about 30 mg per day to about 480 mg per day to a male human with metastatic castration-resistant prostate cancer, or high-risk localized prostate cancer in combination with a taxane or tubulin inhibitor.

Embodiment 98

The method of Embodiment 97, further comprising administering a therapeutically effective amount of a gonadotropin-releasing hormone agonist or antagonist to the male human.

Embodiment 99

The method of any one of Embodiment 97 or Embodiment 98, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, is administered orally at a dose of about 120 mg per day to about 240 mg per day.

Embodiment 100

The method of any one of Embodiments 97 to 99, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, is administered orally at a dose of about 240 mg per day.

Embodiment 101

The method of any one of Embodiments 97 to 100, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, is administered orally in the form of a softgel capsule.

Embodiment 102

The method of any one of Embodiment 97 to 101, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, is administered in combination with Docetaxel.

Embodiment 103

The method of Embodiment 102, wherein Docetaxel is administered by intravenous infusion at a dose of about 35 mg/m$^2$ to about 75 mg/m$^2$ every 3 weeks.

Embodiment 104

The method of any one of Embodiments 97 to 101, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, is administered in combination with Cabazitaxel Embodiment 105

The method of claim 104, wherein Cabazitaxel is administered by intravenous infusion at a dose of about 13 mg/m$^2$ to about 25 mg/m$^2$ every 3 weeks.

Embodiment 106

A method of treating prostate cancer in a male human comprising administering 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, at a dose of about 30 mg per day to about 480 mg per day to a male human with metastatic castration-resistant prostate cancer, non-metastatic castration-resistant prostate cancer, metastatic castration-sensitive prostate cancer, non-metastatic castration-sensitive prostate cancer or high-risk localized prostate cancer in combination with an anti-STEAP-1 antibody drug conjugate.

Embodiment 107

The method of Embodiment 106, further comprising administering a therapeutically effective amount of a gonadotropin-releasing hormone agonist or antagonist to the male human.

Embodiment 108

The method of Embodiment 106 or Embodiment 107, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, is administered orally at a dose of about 120 mg per day to about 240 mg per day.

Embodiment 109

The method of any one of Embodiments 106 to 108, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, is administered orally at a dose of about 240 mg per day.

Embodiment 110

The method of any one of Embodiment 106 to 109, wherein 4-[7-(6-cyano-5-trifluoromethylpyridin-3-yl)-8- oxo-6-thioxo-5,7-diazaspiro[3.4]oct-5-yl]-2-fluoro-N-methylbenzamide, or a pharmaceutically acceptable salt thereof, is administered orally in the form of a softgel capsule.

Embodiment 111

The method of any one of Embodiments 106 to 110, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, is administered in combination with an anti-STEAP-1 antibody drug conjugate.

Embodiment 112

The method of any one of Embodiment 106 to 111, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, is administered in combination with RG7450 (DSTP3086S).

Embodiment 113

A method of treating prostate cancer in a male human comprising administering 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, at a dose of about 30 mg per day to about 480 mg per day to a male human with metastatic castration-resistant prostate cancer, non-metastatic castration-resistant prostate cancer, metastatic castration-sensitive prostate cancer, non-metastatic castration-sensitive prostate cancer or high-risk localized prostate cancer in combination with a HSP90 or HSP27 pathway modulator.

Embodiment 114

The method of Embodiment 113, further comprising administering a therapeutically effective amount of a gonadotropin-releasing hormone agonist or antagonist to the male human.

Embodiment 115

The method of Embodiment 113 or Embodiment 114, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, is administered orally at a dose of about 120 mg per day to about 240 mg per day.

Embodiment 116

The method of any one of Embodiment 113 to 115, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, is administered orally at a dose of about 240 mg per day.

Embodiment 117

The method of any one of Embodiments 113 to 116, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, is administered orally in the form of a softgel capsule.

Embodiment 118

The method of any one of Embodiment 113 to 117, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, is administered in combination with OGX-011 (Custirsen), OGX-427, AUY922, HSP990, PF-04928473, PF-04929113 (SNX-5422), Retaspimycin or AT13387.

Embodiment 119

The method of any one of Embodiment 113 to 118, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, is administered in combination with OGX-011 (Custirsen).

Embodiment 120

The method of Embodiment 119, wherein OGX-011 (Custirsen) is administered by intravenous infusion at a dose of about 320 mg to about 640 mg every week.

Embodiment 121

The method of any one of Embodiment 113 to 118, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, is administered in combination with OGX-427.

Embodiment 122

The method of Embodiment 121, wherein OGX-427 is administered by intravenous infusion at a loading dose of about 300 mg to about 600 mg followed by about 500 mg to about 1000 mg every week.

Embodiment 123

A pharmaceutical composition comprising a nonaqueous, lipid-based solution of 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, in a softgel capsule.

Embodiment 124

The pharmaceutical composition of Embodiment 123, wherein the nonaqueous, lipid-based solution of 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, comprises: 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof, vitamin E d-α-tocopheryl polyethylene glycol 1000 succinate NF (Vitamin E TPGS), polyethylene glycol 400 NF/EP (PEG 400), glycerol monocaprylocaprate EP and caprylocaproyl macroglycerides EP/NF.

Embodiment 125

The pharmaceutical composition of Embodiment 123 or Embodiment 124, wherein the nonaqueous, lipid-based solution of 4-[7-(6-cyano-5-trifluoromethylpyridin-3-yl)-8-oxo- 6-thioxo-5,7-diazaspiro[3.4]oct-5-yl]-2-fluoro-N-methylbenzamide, or a pharmaceutically acceptable salt thereof, comprises about 3% of 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof.

Embodiment 126

The pharmaceutical composition of any one of Embodiment 123 to 125, wherein the softgel capsule shell comprises gelatin NF/EP, a 50:50 sorbitol/glycerin blend USP/EP, and purified water USP/EP.

Embodiment 127

The pharmaceutical composition of any one of Embodiment 123 to 126, wherein a single unit dosage comprises about 30 mg of 4-[7-(6-cyano-5-trifluoromethylpyridin-3-yl)-8-oxo-6-thioxo-5,7-diazaspiro[3.4]oct-5-yl]-2-fluoro-N-methylbenzamide, or a pharmaceutically acceptable salt thereof.

EXAMPLES

These examples are provided for illustrative purposes only and not to limit the scope of the claims provided herein.

Example 1

Anhydrous Lipid-Based Formulation

In one embodiment, an anhydrous lipid-based formulation of 4-[7-(6-cyano-5-trifluoromethylpyridin-3-yl)-8-oxo-6-thioxo-5,7-diazaspiro[3.4]oct-5-yl]-2-fluoro-N-methylbenzamide is prepared with the following list of ingredients:

TABLE 1

Anhydrous Lipid-Based Formulation

| Ingredient | Final Concentration |
|---|---|
| 4-[7-(6-cyano-5-trifluoromethylpyridin-3-yl)-8-oxo-6-thioxo-5,7-diazaspiro[3.4]oct-5-yl]-2-fluoro-N-methylbenzamide | 3-30 mg/mL |
| Capmul MCM | 45% w/w |
| PEG-400 | 30% w/w |
| Vit E-TPGS | 15% w/w |
| Acconon MC8-2 | 10% w/w |

In some embodiments, the lipid-based solution is placed into oral hard gelatin capsules.

Example 2

Softgel Capsule Formulation

4-[7-(6-cyano-5-trifluoromethylpyridin-3-yl)-8-oxo-6-thioxo-5,7-diazaspiro[3.4]oct-5-yl]-2-fluoro-N-methylbenzamide is formulated as a nonaqueous, lipid-based solution that is filled into size 18 oblong softgel capsules for oral administration. The fill solution is composed of 4-[7-(6-cyano-5-trifluoromethylpyridin-3-yl)-8-oxo-6-thioxo-5,7-diazaspiro[3.4]oct-5-yl]-2-fluoro-N-methylbenzamide in vitamin E d-α-tocopheryl polyethylene glycol 1000 succinate NF (Vitamin E TPGS), polyethylene glycol 400 NF/EP (PEG 400), glycerol monocaprylocaprate EP (Capmul MCM), and caprylocaproyl macroglycerides EP/NF (Acconon MC8-2). The softgel capsule shell, contains gelatin NF/EP, a 50:50 sorbitol/glycerin blend USP/EP, and purified water USP/EP. The softgel capsules (where each capsule includes 30 mg of 4-[7-(6-cyano-5-trifluoromethylpyridin-3-yl)-8-oxo-6-thioxo-5,7-diazaspiro[3.4]oct-5-yl]-2-fluoro-N-methylbenzamide) are packaged in 30-ct, 100 cc HDPE bottles with child-resistant closures and tamper proof heat induction seals.

TABLE 2

Softgel Capsule Formulation

| Component | Amount per Unit (mg/Capsule) | w/w (%) |
|---|---|---|
| 4-[7-(6-cyano-5-trifluoromethylpyridin-3-yl)-8-oxo-6-thioxo-5,7-diazaspiro[3.4]oct-5-yl]-2-fluoro-N-methylbenzamide | 30.00 | 3.00 |
| PEG 400 | 291.00 | 29.10 |
| Capmul MCM | 436.50 | 43.65 |
| Acconon MC8-2 | 97.00 | 9.70 |
| Vitamin E TPGS | 144.50 | 14.55 |
| Softgel Capsule Shell | Size 18 Oblong Softgel Capsules | N/A |
| Total Fill Formulation Weight | 1000.00 | 100.00 |

Manufacturing Process for Softgel Capsule:

Fill Formulation Manufacturing

Polyethylene glycol 400 NF/EP (PEG 400) and caprylocaproyl macroglycerides EP/NF (Acconon MC8-2) are transferred under vacuum to a preheated (30° C.) 30 L Becomix mixer and homogenizer. The mixture is warmed to 35° C. under vacuum with agitation and homogenization. Vitamin E d-α-tocopheryl polyethylene glycol 1000 succinate NF (vitamin E TPGS) is warmed to 35-45° C. in a stainless steel vessel then transferred under vacuum to the 30 L Becomix. The mixture is agitated and homogenized under vacuum at 35° C. for NLT 15 minutes. 4-[7-(6-Cyano-5-trifluoromethylpyridin-3-yl)-8-oxo-6-thioxo-5,7-diazaspiro[3.4]oct-5-yl]-2-fluoro-N-methylbenzamide and one third of the total quantity of glycerol monocaprylocaprate EP (Capmul MCM) are transferred to a nitrogen purged glove bag. 4-[7-(6-Cyano-5-trifluoromethylpyridin-3-yl)-8-oxo-6-thioxo-5,7-diazaspiro[3.4]oct-5-yl]-2-fluoro-N-methylbenzamide is transferred to a stainless steel beaker and wetted with Capmul MCM (aliquot 1) to afford a suspension. The mixture is homogenized for no less than 15 minutes to afford a fine suspension with no aggregates. The suspension is removed from the glove bag then transferred under vacuum to the 30 L Becomix. The 4-[7-(6-cyano-5-trifluoromethylpyridin-3-yl)-8-oxo-6-thioxo-5,7-diazaspiro[3.4]oct-5-yl]-2-fluoro-N-methylbenzamide and Capmul MCM stainless vessel is rinsed with the second one third portion of Capmul MCM (aliquot 2) then transferred under vacuum to the 30 L Becomix. This process is repeated with the final one third portion of Capmul MCM (aliquot 3). The mixture is agitated and homogenized under vacuum at 35° C. for no less than 60 minutes. Once a clear solution is obtained, the homogenizer is turned off and the solution is deaerated under vacuum with agitation at 35° C. for NLT 60 minutes. The solution is then filtered through a 75 mm stainless steel in-line filter and transferred to a suitable in-process storage container. The final 4-[7-(6-cyano-5-trifluoromethylpyridin-3-yl)-8-oxo-6-thioxo-5,7-diazaspiro[3.4]oct-5-yl]-2-fluoro-N-methylbenzamide fill solution is weighed and reconciled.

Softgel Capsule Encapsulation

The 4-[7-(6-cyano-5-trifluoromethylpyridin-3-yl)-8-oxo-6-thioxo-5,7-diazaspiro[3.4]oct-5-yl]-2-fluoro-N-methylbenzamide fill solution and softgel mass (Gelatin) are transferred to the softgel encapsulation machine. The softgel mass is cast into two ribbons while lubricating. The lubricated softgel ribbons are passed between the rotating dies and the 4-[7-(6-cyano-5-trifluoromethylpyridin-3-yl)-8-oxo-6-thioxo-5,7-diazaspiro[3.4]oct-5-yl]-2-fluoro-N-methylbenzamide fill solution is fed by gravity to the encapsulation pump under nitrogen gas NF. The pump operates by positive displacement and delivers the target fill weight through a heated (30° C.) filling wedge between rotating dies resulting in the expansion of the gel ribbons to form the size 18, oblong softgel capsules. The dies form seals and cut capsules out from the ribbons in a continuous, hermetically sealed process. Following the encapsulation, the 4-[7-(6-cyano-5-trifluoromethylpyridin-3-yl)-8-oxo-6-thioxo-5,7-diazaspiro[3.4]oct-5-yl]-2-fluoro-N-methylbenzamide softgel capsules are air-dried in a tumble drier then transferred to shallow drying trays. The softgel capsules are spread into single layers in the drying trays and dried in environmentally controlled drying tunnels. After drying, the softgel capsules are transferred to deep holding trays. The softgel capsules are processed through a finishing process to remove the surface lubricant used in the encapsulation and to help reduce size variability in the finished product prior to manually packing into a bulk storage carton containing two polyethylene liners. The softgel capsules are weighed, reconciled and stored under refrigerated conditions (2-8° C.) until clinical packaging is performed.

Softgel Capsule Packaging

The 4-[7-(6-cyano-5-trifluoromethylpyridin-3-yl)-8-oxo-6-thioxo-5,7-diazaspiro[3.4]oct-5-yl]-2-fluoro-N-methylbenzamide softgel capsules are packaged in 30-count, 100 cc HDPE bottles with a child-resistance closure (CRC). An appropriate torque is applied to seal each bottle, the induction seal is activated and the closure retorqued to achieve an immediate removal range of 10-16 inch-pounds. The bottle label is applied to the filled, sealed bottles. The bottles are reconciled, inspected and stored under refrigerated conditions [2° C.-8° C. (36° F.-46° F.)].

Example 3

MDA MB 453: Breast Cancer Xenograft Assay

Time release pellets (12.5 mg 5α-Dihydrotestosterone/60 days) were subcutaneously implanted into female SCID Hairless Outbred (SHO) mice. MDA MB 453 cells were grown in RPMI containing 10% FBS, 10 µg/ml insulin, 10 mM Sodium Pyruvate, 10 mM Non-Essential Amino Acids at 5% $CO_2$, 37° C. Cells were spun down and re-suspended in 50% RPMI (serum free) and 50% Matrigel (BD, high concentration containing phenol red) at $1 \times 10^7$ cells/ml. MDA MB 453 cells were subcutaneously injected (100 µl/animal) on the right flank 2-3 days post pellet implantation. Tumor volume (length×width²/2) was monitored bi-weekly. When tumors reached an average volume of ~350 mm³, animals were randomized and treatment was started. Animals were treated with vehicle or 4-[7-(6-cyano-5-trifluoromethylpyridin-3-yl)-8-oxo-6-thioxo-5,7-diazaspiro[3.4]oct-5-yl]-2-fluoro-N-methylbenzamide daily for 28 days. Tumor volume and body weight were monitored bi-weekly throughout the study. At the conclusion of the treatment period; plasma and tumor samples were taken for pharmacokinetic and pharmacodynamic analyses, respectively.

TABLE 3

Breast Cancer Xenograft Assay Results

| Compound | Number of Tumor Regressions |
|---|---|
| Vehicle (+5α-Dihydrotestosterone (DHT)) | 1/8 |
| Vehicle (−DHT) | 3/8 |
| 4-[7-(6-cyano-5-trifluoromethylpyridin-3-yl)-8-oxo-6-thioxo-5,7-diazaspiro[3.4]oct-5-yl]-2-fluoro-N-methylbenzamide 30 mg/kg/day (−DHT) | 5/10 |
| 4-[7-(6-cyano-5-trifluoromethylpyridin-3-yl)-8-oxo-6-thioxo-5,7-diazaspiro[3.4]oct-5-yl]-2-fluoro-N-methylbenzamide 30 mg/kg/day (+DHT) | 9/9 |

Example 4

Hirsutism Model

Approximately 11 weeks old female Syrian Golden Hamsters [Lak: LVG (SYR) (Outbred)] are purchased. On each of 5 successive days, the dorsal hair on and around the flank organs of ten animals is clipped with electric clippers, and the stubble is removed with Surgex Hair Remover Cream. The hamsters are under ether anesthesia during this procedure, as well as during subsequent treatments. Each group of ten hamsters receive one of the following doses of testosterone propionate (TP) per animal in 0.05 ml of peanut oil injected subcutaneously in the dorsal neck or scapular region: 400 µg, 135 µg, 45 µg, 15 µg, 0 µg. Injections are given daily, except weekends, for 3 weeks. The hamsters are terminated on the $22^{nd}$ day after the initial treatment day by carbon dioxide inhalation. All of the pelage hair within 1 cm of the regrown flank organ hair is cut as close to the skin as possible with fine scissors. The TP-stimulated flank organ hair, distinguished by its coarseness and pigmentation from the pelage hair, is then plucked with wax. The hair is recovered by dissolving the wax in xylene and trapping the hair on humidity-equilibrated, tarred, glass fibre filters. After the hairs have been washed free of wax and the residual xylene has been evaporated, the hairs and filters are again humidity-equilibrated and weighed. Hamsters used to determine the effect of topical 4-[7-(6-cyano-5-trifluoromethylpyridin-3-yl)-8-oxo-6-thioxo-5,7-diazaspiro[3.4]oct-5-yl]-2-fluoro-N-methylbenzamide on flank organ hair growth in TP-stimulated animals are 12 weeks old at the start of the experiment. These hamsters are stimulated with a subcutaneous injection of 200 µg of TP daily, for approximately 3 weeks, a dose estimated by probit analysis to produce at least a doubling of the flank organ hair mass in the test animals. Immediately following injection, each hamster receives a topical treatment of 4-[7-(6-cyano-5-trifluoromethylpyridin-3-yl)-8-oxo-6-thioxo-5,7-diazaspiro[3.4]oct-5-yl]-2-fluoro-N-methylbenzamide in a carrier such as acetone on one flank organ and control (i.e. acetone only) on the contralateral flank organ. The control group received no TP and the acetone vehicle only. The hair from the treatment and control groups is recovered as described above and weighed.

Example 5

Uterine Leiomyoma Studies

Healthy female Eker rats at 12 months of age are randomized into study article and vehicle groups to study the effect of 4-[7-(6-cyano-5-trifluoromethylpyridin-3-yl)-8-oxo-6-thioxo-5,7-diazaspiro[3.4]oct-5-yl]-2-fluoro-N-methylbenzamide on uterine leiomyoma. In the 4-[7-(6-cyano-5-trifluoromethylpyridin-3-yl)-8-oxo-6-thioxo-5,7-diazaspiro[3.4]oct-5-yl]-2-fluoro-N-methylbenzamide treatment group, 4-[7-(6-cyano-5-trifluoromethylpyridin-3-yl)-8-oxo-6-thioxo-5,7-diazaspiro[3.4]oct-5-yl]-2-fluoro-N-methylbenzamide is dosed daily in twelve-month-old and 10 fourteen-month-old rats. 4-[7-(6-Cyano-5-trifluoromethylpyridin-3-yl)-8-oxo-6-thioxo-5,7-diazaspiro[3.4]oct-5-yl]-2-fluoro-N-methylbenzamide treated animals are individually tracked using nonsurgically inserted subcutaneous transponders. Statistical analysis of tumor incidence data is performed using chi-square analysis and the comparison of tumor size between groups is performed by a contingency table analysis using Fisher exact method. Two hours before sacrifice, rats from each group are injected with 5'-bromo-2'-deoxyuridine (BrdU) at 100 mg/kg. Animals are euthanized by $CO_2$ (g) and examined for grossly observable tumors of the reproductive tract. Vaginas, ovaries, and uteri are fixed in 10%, neutral-buffered formalin (NBF). Measurements of grossly observable uterine tumors are taken and sections of tumors fixed in 10%, NBF. Portions from tumors of sufficient size are quick-frozen in liquid nitrogen. Tissues remain in 10%, NBF for 48 hours and are paraffin embedded by routine methods. All samples are sectioned and stained with hematoxylin and eosin. Microscopic lesions of the uteri are recorded and all tumors are classified based on their morphology Histologic slides are coded and read by two independent pathologists.

Example 6

Breast Cancer Clinical Trial

A non-limiting example of a breast cancer clinical trial in humans involving the use of 4-[7-(6-cyano-5-trifluoromethylpyridin-3-yl)-8-oxo-6-thioxo-5,7-diazaspiro[3.4]oct-5-yl]-2-fluoro-N-methylbenzamide is described below.

Purpose:

The purposes of this study is to assess the efficacy of 4-[7-(6-cyano-5-trifluoromethylpyridin-3-yl)-8-oxo-6-thioxo-5,7-diazaspiro[3.4]oct-5-yl]-2-fluoro-N-methylbenzamide as single agent or in combination, as first- or second-line treatment of breast cancer in which AR could be the driver of tumor growth, collect information on any side effects the compound may cause as single agent or in combination, and evaluate the pharmacokinetic properties of the compound as single agent or in combination.

Intervention:

Patients are administered up to 480 mg of 4-[7-(6-cyano-5-trifluoromethylpyridin-3-yl)-8-oxo-6-thioxo-5,7-diazaspiro[3.4]oct-5-yl]-2-fluoro-N-methylbenzamide per day as single agent or in combination.

Outcome Measures:

Primary Outcome Measures: tumor response and/or disease control.

Secondary Outcome Measures:

(a) side-effects; (b) pharmacokinetic properties; (c) time to progression and overall survival; and (d) biomarkers predictive of clinical response.

Detailed Description:

Patients will be given 4-[7-(6-cyano-5-trifluoromethylpyridin-3-yl)-8-oxo-6-thioxo-5,7-diazaspiro[3.4]oct-5-yl]-2-fluoro-N-methylbenzamide, orally once a day as single agent or in combination. Prior to each dosing cycle, a physical exam, blood work and assessment of any side effects will be performed. Every 8-12 weeks the patient's cancer will be re-evaluated with either a CT scan or MRI to determine whether the treatment is working. Participation in this study will last until disease progression or unacceptable toxicity.

Eligibility:

Female subjects that are 18 years and older.

Inclusion Criteria:

Histologically or cytologically confirmed diagnosis of invasive breast cancer, stage IV disease; at least one measurable target lesion as defined by RECIST that has not been previously treated with local therapy; post-menopausal status; AR positive breast cancer; HER2-negative breast cancer or HER2-positive breast cancer (following treatment with HER-2 targeting agent(s)); up to one prior hormonal therapy for advanced or metastatic disease; ECOG performance status 0-1; life expectancy >12 weeks; adequate liver and bone marrow function: AST<2.5×ULN; Bilirubin<1.5×ULN; ANC>1,500/ul; platelet count>100,000/ul; normal PT and PTT; at least 2 weeks since prior radiation and recovered from treatment-related toxicity.

Exclusion Criteria:

Prior chemotherapy regimen for metastatic disease; history of, or presence of brain metastases; concurrent investigational drug treatment; history of other malignancy within the last 5 years, not including curatively-treated carcinoma in situ of the cervix or non-melanoma skin cancer; uncontrolled infection; active bleeding, or history of bleeding requiring transfusion; active cardiac disease; serious medical or psychiatric illness.

Example 7

Endometrial Carcinoma Clinical Trial

A non-limiting example of an endometrial carcinoma clinical trial in humans involving the use of 4-[7-(6-cyano-5-trifluoromethylpyridin-3-yl)-8-oxo-6-thioxo-5,7-diazaspiro[3.4]oct-5-yl]-2-fluoro-N-methylbenzamide is described below.

Purpose:

The purposes of this study is to assess the efficacy of 4-[7-(6-cyano-5-trifluoromethylpyridin-3-yl)-8-oxo-6-thioxo-5,7-diazaspiro[3.4]oct-5-yl]-2-fluoro-N-methylbenzamide as single agent or in combination in the treatment of advanced or metastatic endometrial carcinoma, collect information on any side effects the compound as single agent or in combination may cause, and evaluate the pharmacokinetic properties of the compound as single agent or in combination.

Intervention:

Patients are administered up to 480 mg of 4-[7-(6-cyano-5-trifluoromethylpyridin-3-yl)-8-oxo-6-thioxo-5,7-diazaspiro[3.4]oct-5-yl]-2-fluoro-N-methylbenzamide per day as single agent or in combination.

Outcome Measures:

Primary Outcome Measures: tumor response and/or disease control Secondary Outcome Measures: (a) side-effects; (b) pharmacokinetic properties; (c) time to progression and overall survival; and (d) biomarkers predictive of clinical response.

Detailed Description:

Patients will be given 4-[7-(6-cyano-5-trifluoromethylpyridin-3-yl)-8-oxo-6-thioxo-5,7-diazaspiro[3.4]oct-5-yl]-2-fluoro-N-methylbenzamide orally once a day as single agent or in combination. Prior to each dosing cycle, a physical exam, blood work and assessment of any side effects will be performed. Every 8-12 weeks the patient's cancer will be re-evaluated with either a CT scan or MRI to determine whether the treatment is working Participation in this study will last until disease progression or unacceptable toxicity.

Eligibility:
Female subjects that are 18 years and older.

Inclusion Criteria:
Histologically or cytologically confirmed diagnosis of advanced or metastatic endometrial carcinoma; at least one measurable target lesion as defined by RECIST that has not been previously treated with local therapy; hormone receptor positive endometrial carcinoma; ECOG performance status 0-1; life expectancy >12 weeks; adequate liver and bone marrow function: AST<2.5×ULN; Bilirubin<1.5×ULN; ANC>1,500/ul; platelet count>100,000/ul; normal PT and PTT; at least 2 weeks since prior radiation and recovered from prior surgery or treatment-related toxicity.

Exclusion Criteria:
History of, or presence of brain metastases; concurrent investigational drug treatment; history of other malignancy within the last 5 years, not including curatively-treated carcinoma in situ of the cervix or non-melanoma skin cancer; uncontrolled infection; active bleeding, or history of bleeding requiring transfusion; active cardiac disease; serious medical or psychiatric illness.

Example 8

Endometriosis Clinical Trial

A non-limiting example of an endometriosis clinical trial in humans involving the use of 4-[7-(6-cyano-5-trifluoromethylpyridin-3-yl)-8-oxo-6-thioxo-5,7-diazaspiro[3.4]oct-5-yl]-2-fluoro-N-methylbenzamide is described below.

Purpose:
The purposes of this study is to assess the efficacy of a compound of 4-[7-(6-cyano-5-trifluoromethylpyridin-3-yl)-8-oxo-6-thioxo-5,7-diazaspiro[3.4]oct-5-yl]-2-fluoro-N-methylbenzamide as single agent or in combination in the treatment of patients with symptomatic/severe endometriosis, collect information on any side effects the compound may cause as single agent or in combination, and evaluate the pharmacokinetic properties of the compound as single agent or in combination.

Intervention:
Patients are administered up to 480 mg of 4-[7-(6-Cyano-5-trifluoromethylpyridin-3-yl)-8-oxo-6-thioxo-5,7-diazaspiro[3.4]oct-5-yl]-2-fluoro-N-methylbenzamide per day as single agent or in combination.

Outcome Measures:
The outcome measures of this study are symptoms improvement and/or pain relief, amount of menstrual blood loss, and shrinkage of endometrial tissue.

Detailed Description:
Patients will be given 4-[7-(6-cyano-5-trifluoromethylpyridin-3-yl)-8-oxo-6-thioxo-5,7-diazaspiro[3.4]oct-5-yl]-2-fluoro-N-methylbenzamide orally once or twice a day as single agent or in combination. Prior to each dosing cycle, a physical exam, blood work and assessment of any side effects will be performed.

Eligibility:
Female subjects that are 18 years and older.

Inclusion Criteria:
Diagnosis of symptomatic endometriosis; pre- or peri-menopausal status; ECOG performance status 0-1; adequate liver and bone marrow function: AST<2.5×ULN; Bilirubin<1.5×ULN; ANC>1,500/ul; platelet count>100,000/ul; normal PT and PTT; at least 2 weeks since prior surgery or treatment-related toxicity.

Exclusion Criteria:
Pregnancy or lactating; history of other malignancy within the last 5 years, not including curatively-treated carcinoma in situ of the cervix or non-melanoma skin cancer; concurrent investigational drug treatment; uncontrolled infection; active cardiac disease; aerious medical or psychiatric illness.

Example 9

Uterine Leiomyoma Clinical Trial

A non-limiting example of an uterine leiomyoma clinical trial in humans involving the use of 4-[7-(6-cyano-5-trifluoromethylpyridin-3-yl)-8-oxo-6-thioxo-5,7-diazaspiro[3.4]oct-5-yl]-2-fluoro-N-methylbenzamide is described below.

Purpose:
The purposes of this study is to assess the efficacy of 4-[7-(6-cyano-5-trifluoromethylpyridin-3-yl)-8-oxo-6-thioxo-5,7-diazaspiro[3.4]oct-5-yl]-2-fluoro-N-methylbenzamide as single agent or in combination in the treatment of patients with symptomatic uterine leiomyoma, collect information on any side effects the compound may cause as single agent or in combination, and evaluate the pharmacokinetic properties of the compound as single agent or in combination.

Intervention:
Patients are administered 480 mg of 4-[7-(6-cyano-5-trifluoromethylpyridin-3-yl)-8-oxo-6-thioxo-5,7-diazaspiro[3.4]oct-5-yl]-2-fluoro-N-methylbenzamide per day as single agent or in combination.

Outcome Measures:
The outcome measures of this study are symptoms improvement and/or pain relief and shrinkage of leiomyomas.

Detailed Description:
Patients will be given 4-[7-(6-cyano-5-trifluoromethylpyridin-3-yl)-8-oxo-6-thioxo-5,7-diazaspiro[3.4]oct-5-yl]-2-fluoro-N-methylbenzamide orally once or twice a day as single agent or in combination. Prior to each dosing cycle, a physical exam, blood work and assessment of any side effects will be performed.

Eligibility:
Female subjects that are 18 years and older.

Inclusion Criteria:
Diagnosis of symptomatic uterine leiomyoma; pre- or peri-menopausal status; ECOG performance status 0-1; adequate liver and bone marrow function: AST<2.5×ULN; Bilirubin<1.5×ULN; ANC>1,500/ul; platelet count>100,000/ul; normal PT and PTT; at least 2 weeks since prior surgery or treatment-related toxicity.

Exclusion Criteria:
Pregnancy or lactating; history of other malignancy within the last 5 years, not including curatively-treated carcinoma in situ of the cervix or non-melanoma skin cancer; concurrent investigational drug treatment; uncontrolled infection; active cardiac disease; serious medical or psychiatric illness.

Example 10

LNCaP/AR Model for Castrate Resistant Prostate Cancer Xenograft Studies in Combination Therapy Six to Seven week old male SCID Hairless Outbred mice (SHO, Charles Rivers Laboratories) underwent bilateral orchiectomy under isoflurane anesthesia. LNCaP/AR cells were grown in RPMI at 5% $CO_2$, 37° C. Cells were spun down and re-suspended in 50% serum-free RPMI and 50% Matrigel at $1 \times 10^7$ cells/ml. LNCaP/AR cells were subcutaneously injected (100 μl/animal) on the right flank 3-5 days post castration. Tumor volume (length×width$^2$/2) was monitored weekly. When tumors reached an average volume of ~200 mm$^3$ animals were randomized into treatment groups. During the treatment period tumor volume was monitored bi-weekly. At the termination of the study, tumors were collected and stored for further analyses. All compounds were administered daily by oral gavage. Statistical analyses were performed using Graphpad Prism.

By way of example, in one embodiment, 4-[7-(6-cyano-5-trifluoromethylpyridin-3-yl)-8-oxo-6-thioxo-5,7-diazaspiro[3.4]oct-5-yl]-2-fluoro-N-methylbenzamide (ARN-509) was administered in combination with BKM120 (a PI3K inhibitor that is also known as 5-(2,6-dimorpholinopyrimidin-4-yl)-4-(trifluoromethyl)pyridin-2-amine) in this LNCaP/AR Model of CRPC.

TABLE 4

Combination with a PI3K inhibitor

| Compound 1 | Compound 2 | Number of regressions > 50% |
|---|---|---|
| 4-[7-(6-cyano-5-trifluoromethylpyridin-3-yl)-8-oxo-6-thioxo-5,7-diazaspiro[3.4]oct-5-yl]-2-fluoro-N-methylbenzamide 3 mg/kg/day | — | 2/10 |
| BKM120 20 mg/kg | — | 1/10 |
| BKM120 40 mg/kg | — | 0/9 |
| 4-[7-(6-cyano-5-trifluoromethylpyridin-3-yl)-8-oxo-6-thioxo-5,7-diazaspiro[3.4]oct-5-yl]-2-fluoro-N-methylbenzamide 3 mg/kg/day | BKM120 20 mg/kg | 0/9 |
| 4-[7-(6-cyano-5-trifluoromethylpyridin-3-yl)-8-oxo-6-thioxo-5,7-diazaspiro[3.4]oct-5-yl]-2-fluoro-N-methylbenzamide 3 mg/kg/day | BKM120 40 mg/kg | 5/10 |

In another embodiment, 4-[7-(6-cyano-5-trifluoromethylpyridin-3-yl)-8-oxo-6-thioxo-5,7-diazaspiro[3.4]oct-5-yl]-2-fluoro-N-methylbenzamide (ARN-509) was administered in combination with Everolimus in this LNCaP/AR Model of CRPC.

TABLE 5

Combination with a TORC inhibitor

| Compound 1 | Compound 2 | Number of regressions > 50% |
|---|---|---|
| 4-[7-(6-cyano-5-trifluoromethylpyridin-3-yl)-8-oxo-6-thioxo-5,7-diazaspiro[3.4]oct-5-yl]-2-fluoro-N-methylbenzamide 3 mg/kg/day | — | 1/10 |
| Everolimus 5 mg/kg/day | — | 0/8 |
| Everolimus 10 mg/kg/day | — | 2/10 |
| 4-[7-(6-cyano-5-trifluoromethylpyridin-3-yl)-8-oxo-6-thioxo-5,7-diazaspiro[3.4]oct-5-yl]-2-fluoro-N-methylbenzamide 3 mg/kg/day | Everolimus 5 mg/kg/day | 4/9 |
| 4-[7-(6-cyano-5-trifluoromethylpyridin-3-yl)-8-oxo-6-thioxo-5,7-diazaspiro[3.4]oct-5-yl]-2-fluoro-N-methylbenzamide 3 mg/kg/day | Everolimus 10 mg/kg/day | 6/10 |

Example 11

PTEN KO Model of Prostate Cancer

Ptenlox/lox; PB-Cre mice (age 6-8 months) are imaged by small animal MRI imaging core prior to and at the completion of treatment. All mice are castrated. Surgical castration is performed under anesthesia with isoflurane. Mice are monitored postoperatively for recovery.

Mice are administered control vehicle or test article by oral gavage daily Monday through Friday schedule for a total of 35 days. MRI tumor volumes are reported for each mouse at time point zero (T0) at initiation of study and time point 35 days (T35) at completion of study. Changes in tumor volumes between T0 and T35 are calculated for individual mice and reported in waterfall plots. At study end, mice were euthanized by $CO_2$ asphyxiation, and tissue was collected for histology, mRNA analysis, protein analysis and other analyses.

Example 12

Clinical Trial for the Combination of an Anti-Androgen with a PI3K Inhibitor, TORC Inhibitor, or Dual PI3K/TORC Inhibitor A non-limiting example of a prostate cancer clinical trial in humans involving the combination of 4-[7-(6-cyano-5-trifluoromethylpyridin-3-yl)-8-oxo-6-thioxo-5,7-diazaspiro[3.4]oct-5-yl]-2-fluoro-N-methylbenzamide and a PI3K inhibitor, TORC inhibitor, or dual PI3K/TORC inhibitor is described below.

Purpose:

The purposes of this study is to assess the safety and efficacy of a combination of 4-[7-(6-cyano-5-trifluoromethylpyridin-3-yl)-8-oxo-6-thioxo-5,7-diazaspiro[3.4]oct-5-yl]-2-fluoro-N-methylbenzamide and a PI3K inhibitor, TORC inhibitor, or dual PI3K/TORC inhibitor in humans with prostate cancer (e.g. post-abiraterone acetate treated metastatic castration-resistant prostate cancer, metastatic castration-resistant prostate cancer, non-metastatic castration-resistant prostate cancer, metastatic castration-sensitive prostate cancer, non-metastatic castration-sensitive prostate cancer or high-risk localized prostate cancer), collect information on any side effects the combination therapy may cause, and evaluate the pharmacokinetic properties of the compounds in the context of combination therapy.

Intervention:

Patients are administered 4-[7-(6-cyano-5-trifluoromethylpyridin-3-yl)-8-oxo-6-thioxo-5,7-diazaspiro[3.4]oct-5-yl]-2-fluoro-N-methylbenzamide at a dose of 240 mg per day. However, dose adjustment of 4-[7-(6-cyano-5-trifluoromethylpyridin-3-yl)-8-oxo-6-thioxo-5,7-diazaspiro[3.4]oct-5-yl]-2-fluoro-N-methylbenzamide (120 mg to 480 mg per day) will be considered during the trial if deemed necessary. The TORC inhibitor everolimus will be administered at a dose of 5 mg per day. However, dose adjustment of everolimus (5 mg to 20 mg per day) will be considered during the trial if deemed necessary.

Outcome Measures:

Overall and 12-week PSA response (decrease of PSA by ≥50% from baseslilne); Time to PSA Progression; overall survival (OS); PFS (Progression-free survival by CT/MRI/radio-tracer); quality of life (QOL); side-effects; pharmacokinetics (PK); tumor response and/or disease control; proportion of patients that have complete or partial response or stable disease at defined time points; biomarkers predictive of clinical response.

Eligibility:

Male subjects that are 18 years and older.

Inclusion Criteria:

Histologically or cytologically confirmed adenocarcinoma of the prostate (e.g. post-abiraterone acetate treated metastatic castration-resistant prostate cancer, metastatic castration-resistant prostate cancer, non-metastatic castration-resistant prostate cancer, metastatic castration-sensitive prostate cancer, non-metastatic castration-sensitive prostate cancer or high-risk localized prostate cancer); castration-resistant prostate cancer demonstrated during continuous androgen deprivation therapy (ADT)/post orchiectomy, defined as 3 consecutive rises of PSA, 1 week apart, resulting in two 50% increases over the nadir, with the last PSA>2 ng/mL; maintain castrate levels of testosterone (<50 ng/dL [1.72 nmol/L]) within 4 weeks of randomization and throughout the study; patients currently receiving bone loss prevention treatment with bone-sparing agents (e.g., bisphosphonates, denosumab [PROLIA™ denosumab]) must be on stable doses for at least 4 weeks prior to randomization; patients who received a first generation anti-androgen (e.g., bicalutamide, flutamide, nilutamide) as part of an initial combined androgen blockade therapy or as second-line hormonal therapy must show continuing disease (PSA) progression off the anti-androgen for at least 4 weeks prior to randomization; at least 4 weeks must have elapsed from the use of 5-α reductase inhibitors (e.g., dutasteride, finasteride, aminoglutethamide), estrogens, and any other anti-cancer therapy prior to randomization, including chemotherapy given in the adjuvant/neoadjuvant setting (e.g., clinical trial); at least 4 weeks must have elapsed from major surgery or radiation therapy prior to randomization.

Exclusion Criteria:

History of seizure, CNS metastasis.

Example 13

Clinical Trial for the Combination of an Anti-Androgen with a CYP17 Inhibitor

A non-limiting example of a prostate cancer clinical trial in humans involving the combination of 4-[7-(6-cyano-5-trifluoromethylpyridin-3-yl)-8-oxo-6-thioxo-5,7-diazaspiro[3.4]oct-5-yl]-2-fluoro-N-methylbenzamide and a CYP17 inhibitor is described below.

Purpose:

The purposes of this study is to assess the safety and efficacy of a combination of 4-[7-(6-cyano-5-trifluoromethylpyridin-3-yl)-8-oxo-6-thioxo-5,7-diazaspiro[3.4]oct-5-yl]-2-fluoro-N-methylbenzamide and a CYP17 inhibitor in humans with prostate cancer (e.g. metastatic castration-resistant prostate cancer, non-metastatic castration-resistant prostate cancer, metastatic castration-sensitive prostate cancer, non-metastatic castration-sensitive prostate cancer or high-risk localized prostate cancer), collect information on any side effects the combination therapy may cause, and evaluate the pharmacokinetic properties of the compounds in the context of combination therapy.

Intervention:

Patients are administered 4-[7-(6-cyano-5-trifluoromethylpyridin-3-yl)-8-oxo-6-thioxo-5,7-diazaspiro[3.4]oct-5-yl]-2-fluoro-N-methylbenzamide at a dose of 240 mg per day. However, dose adjustment of 4-[7-(6-cyano-5-trifluoromethylpyridin-3-yl)-8-oxo-6-thioxo-5,7-diazaspiro[3.4]oct-5-yl]-2-fluoro-N-methylbenzamide (120 mg to 480 mg per day) will be considered during the trial if deemed necessary. The CYP17 inhibitor abiraterone acetate will be administered at a dose of 1000 mg once per day. However, dose adjustment of abiraterone acetate (500 mg to 1000 mg per day) will be considered during the trial if deemed necessary. Patients that are administered abiraterone acetate will also be administered prednisone (5 mg) twice per day.

Outcome Measures:

Overall and 12-week PSA response (decrease of PSA by ≥50% from basesline); Time to PSA Progression; overall survival (OS); PFS (Progression-free survival by CT/MRI/radio-tracer); quality of life (QOL); side-effects; pharmacokinetics (PK); tumor response and/or disease control; proportion of patients that have complete or partial response or stable disease at defined time points; biomarkers predictive of clinical response.

Eligibility:

Male subjects that are 18 years and older.

Inclusion Criteria:

Histologically or cytologically confirmed adenocarcinoma of the prostate (e.g. metastatic castration-resistant prostate cancer, non-metastatic castration-resistant prostate cancer, metastatic castration-sensitive prostate cancer, non-metastatic castration-sensitive prostate cancer or high-risk localized prostate cancer); castration-resistant prostate cancer demonstrated during continuous androgen deprivation therapy (ADT)/post orchiectomy, defined as 3 consecutive rises of PSA, 1 week apart, resulting in two 50% increases over the nadir, with the last PSA>2 ng/mL; maintain castrate levels of testosterone (<50 ng/dL [1.72 nmol/L]) within 4 weeks of randomization and throughout the study; patients currently receiving bone loss prevention treatment with bone-sparing agents (e.g., bisphosphonates, denosumab [PROLIA™ denosumab]) must be on stable doses for at least 4 weeks prior to randomization; patients who received a first generation anti-androgen (e.g., bicalutamide, flutamide, nilutamide) as part of an initial combined androgen blockade therapy or as second-line hormonal therapy must show continuing disease (PSA) progression off the anti-androgen for at least 4 weeks prior to randomization; at least 4 weeks must have elapsed from the use of 5-.alpha. reductase inhibitors (e.g., dutasteride, finasteride, aminoglutethamide), estrogens, and any other anti-cancer therapy prior to randomization, including chemotherapy given in the adjuvant/neoadjuvant setting (e.g., clinical trial); at least 4 weeks must have elapsed from major surgery or radiation therapy prior to randomization.

Exclusion Criteria:

Prior chemotherapy, prior CYP17 or second-generation antiandrogen therapy, CNS metastasis, prior history of seizure.

Example 14

Clinical Trial for the Combination of an Anti-Androgen with a GnRH/LHRH Agonist/Antagonist A non-limiting example of a prostate cancer clinical trial in humans involving the combination of 4-[7-(6-cyano-5-trifluoromethylpyridin-3-yl)-8-oxo-6-thioxo-5,7-diazaspiro[3.4]oct-5-yl]-2-fluoro-N-methylbenzamide and a GnRH/LHRH agonist/antagonist is described below.

Purpose:

The purposes of this study is to assess the efficacy of a combination of 4-[7-(6-cyano-5-trifluoromethylpyridin-3-yl)-8-oxo-6-thioxo-5,7-diazaspiro[3.4]oct-5-yl]-2-fluoro-N-methylbenzamide and a GnRH/LHRH agonist/antagonist in humans with prostate cancer (e.g. metastatic castration-resistant prostate cancer, non-metastatic castration-resistant prostate cancer, metastatic castration-sensitive prostate cancer, non-metastatic castration-sensitive prostate cancer or high-risk localized prostate cancer), collect information on any side effects the combination therapy may cause, and evaluate the pharmacokinetic properties of the compounds in the context of combination therapy.

Intervention:

Patients are administered 4-[7-(6-cyano-5-trifluoromethylpyridin-3-yl)-8-oxo-6-thioxo-5,7-diazaspiro[3.4]oct-5-yl]-2-fluoro-N-methylbenzamide at a dose of 240 mg per day. However, dose adjustment of 4-[7-(6-cyano-5-trifluoromethylpyridin-3-yl)-8-oxo-6-thioxo-5,7-diazaspiro[3.4]oct-5-yl]-2-fluoro-N-methylbenzamide (120 mg to 480 mg per day) will be considered during the trial if deemed necessary. The patients will also be administered a GnRH/LHRH agonist/antagonist in addition to 4-[7-(6-cyano-5-trifluoromethylpyridin-3-yl)-8-oxo-6-thioxo-5,7-diazaspiro[3.4]oct-5-yl]-2-fluoro-N-methylbenzamide. In some embodiments, the GnRH/LHRH agonist/antagonist is Lupron which is administered as a depot injection at a dose of about 7.5 mg every 4 weeks, or 22.5 mg every 3 months, or about 30 mg every 4 months, or about 45 mg every 6 months. In other embodiments, the GnRH/LHRH agonist/antagonist is zoladex (Goserelin) which is administered as a subcutaneous implant at a dose of about 3.6 mg every 4 weeks or about 10.8 mg every 12 weeks. In some other embodiments, the GnRH/LHRH agonist/antagonist is Degarelix which is administered as a subcutaneous injection at a dose of about 240 mg followed by about 80 mg administered every 4 weeks.

Outcome Measures:

Overall and 12-week PSA response (decrease of PSA by ≥50% from basesline); Time to PSA Progression; overall survival (OS); PFS (Progression-free survival by CT/MRI/radio-tracer); quality of life (QOL); side-effects; pharmacokinetics (PK); tumor response and/or disease control; proportion of patients that have complete or partial response or stable disease at defined time points; biomarkers predictive of clinical response.

Eligibility:

Male subjects that are 18 years and older.

Inclusion Criteria:

Histologically or cytologically confirmed adenocarcinoma of the prostate (e.g. metastatic castration-resistant prostate cancer, non-metastatic castration-resistant prostate cancer, metastatic castration-sensitive prostate cancer, non-metastatic castration-sensitive prostate cancer or high-risk localized prostate cancer); patients currently receiving bone loss prevention treatment with bone-sparing agents (e.g., bisphosphonates, denosumab [PROLIA™ denosumab]) must be on stable doses for at least 4 weeks prior to randomization; patients who received prior anti-cancer therapy prior to randomization, including chemotherapy given in the adjuvant/neoadjuvant setting (e.g., clinical trial) must have recovered from the acute toxicities of the treatment; at least 4 weeks must have elapsed from major surgery or radiation therapy prior to randomization.

Exclusion Criteria:

Prior CYP17 or second-generation antiandrogen therapy, CNS metastasis, prior history of seizure.

Example 15

Clinical Trial for the Combination of an Anti-Androgen with an Osteoprotective Agent A non-limiting example of a prostate cancer clinical trial in humans involving the combination of 4-[7-(6-cyano-5-trifluoromethylpyridin-3-yl)-8-oxo-6-thioxo-5,7-diazaspiro[3.4]oct-5-yl]-2-fluoro-N-methylbenzamide and an osteoprotective agent is described below.

Purpose:

The purposes of this study is to assess the safety and efficacy of a combination of 4-[7-(6-cyano-5-trifluoromethylpyridin-3-yl)-8-oxo-6-thioxo-5,7-diazaspiro[3.4]oct-5-yl]-2-fluoro-N-methylbenzamide and an osteoprotective agent in humans with prostate cancer (e.g. metastatic castration-resistant prostate cancer, non-metastatic castration-resistant prostate cancer, metastatic castration-sensitive prostate cancer, non-metastatic castration-sensitive prostate cancer or high-risk localized prostate cancer), collect information on any side effects the combination therapy may cause, and evaluate the pharmacokinetic properties of the compounds in the context of combination therapy.

Intervention:

Patients are administered 4-[7-(6-cyano-5-trifluoromethylpyridin-3-yl)-8-oxo-6-thioxo-5,7-diazaspiro[3.4]oct-5-yl]-2-fluoro-N-methylbenzamide at a dose of 240 mg per day. However, dose adjustment of 4-[7-(6-cyano-5-trifluoromethylpyridin-3-yl)-8-oxo-6-thioxo-5,7-diazaspiro[3.4]oct-5-yl]-2-fluoro-N-methylbenzamide (120 mg to 480 mg per day) will be considered during the trial if deemed necessary. The patients will also be administered an osteoprotective agent in addition to 4-[7-(6-cyano-5-trifluoromethylpyridin-3-yl)-8-oxo-6-thioxo-5,7-diazaspiro[3.4]oct-5-yl]-2-fluoro-N-methylbenzamide. In some embodiments, the osteoprotective agent is denosumab which is administered by subcutaneous injection at a dose of about 60 mg to about 120 mg every 4 weeks to every 6 months. In other embodiments, the osteoprotective agent is zoledronic acid which is administered by intravenous infusion at a dose of about 4 mg every 4 weeks to every 12 weeks.

Outcome Measures:

Overall and 12-week PSA response (decrease of PSA by ≥50% from basesline); Time to PSA Progression; overall survival (OS); PFS (Progression-free survival by CT/MRI/radio-tracer); quality of life (QOL); side-effects; pharmacokinetics (PK); tumor response and/or disease control; proportion of patients that have complete or partial response or stable disease at defined time points; biomarkers predictive of clinical response.

Eligibility:

Male subjects that are 18 years and older.

Inclusion Criteria:

Histologically or cytologically confirmed adenocarcinoma of the prostate (e.g. metastatic castration-resistant prostate cancer, non-metastatic castration-resistant prostate cancer, metastatic castration-sensitive prostate cancer, non-metastatic castration-sensitive prostate cancer or high-risk localized prostate cancer); metastatic castration-resistant prostate cancer demonstrated during continuous androgen deprivation therapy (ADT)/post orchiectomy, defined as 3 consecutive rises of PSA, 1 week apart, resulting in two 50% increases over the nadir, with the last PSA>2 ng/mL; maintain castrate levels of testosterone (<50 ng/dL [1.72 nmol/L]) within 4 weeks of randomization and throughout the study; patients who received a first generation anti-androgen (e.g., bicalutamide, flutamide, nilutamide) as part of an initial combined androgen blockade therapy or as second-line hormonal therapy must show continuing disease (PSA) progression off the anti-androgen for at least 4 weeks prior to randomization; at least 4 weeks must have elapsed from the use of 5-α reductase inhibitors (e.g., dutasteride, finasteride, aminoglutethamide), estrogens, and any other anti-cancer therapy prior to randomization, including chemotherapy given in the adjuvant/neoadjuvant setting (e.g., clinical trial); at least 4 weeks must have elapsed from major surgery or radiation therapy prior to randomization.

Exclusion Criteria:

Prior second-generation antiandrogen therapy, CNS metastasis, prior history of seizure.

Example 16

Clinical Trial for the Combination of an Anti-Androgen with Radiation Therapy

A non-limiting example of a prostate cancer clinical trial in humans involving the combination of 4-[7-(6-cyano-5-trifluoromethylpyridin-3-yl)-8-oxo-6-thioxo-5,7-diazaspiro[3.4]oct-5-yl]-2-fluoro-N-methylbenzamide and radiation therapy is described below.

Purpose:

The purposes of this study is to assess the safety and efficacy of a combination of 4-[7-(6-cyano-5-trifluoromethylpyridin-3-yl)-8-oxo-6-thioxo-5,7-diazaspiro[3.4]oct-5-yl]-2-fluoro-N-methylbenzamide and radiation therapy in humans with prostate cancer (e.g. metastatic castration-resistant prostate cancer, non-metastatic castration-resistant prostate cancer, metastatic castration-sensitive prostate cancer, non-metastatic castration-sensitive prostate cancer or high-risk localized prostate cancer), collect information on any side effects the combination therapy may cause, and evaluate the pharmacokinetic properties of the compounds in the context of combination therapy.

Intervention:

Patients are administered 4-[7-(6-cyano-5-trifluoromethylpyridin-3-yl)-8-oxo-6-thioxo-5,7-diazaspiro[3.4]oct-5-yl]-2-fluoro-N-methylbenzamide at a dose of 240 mg per day. However, dose adjustment of 4-[7-(6-cyano-5-trifluoromethylpyridin-3-yl)-8-oxo-6-thioxo-5,7-diazaspiro[3.4]oct-5-yl]-2-fluoro-N-methylbenzamide (120 mg to 480 mg per day) will be considered during the trial if deemed necessary. The patients will also be administered a second therapeutic agent in addition to 4-[7-(6-cyano-5-trifluoromethylpyridin-3-yl)-8-oxo-6-thioxo-5,7-diazaspiro[3.4]oct-5-yl]-2-fluoro-N-methylbenzamide. In some embodiments, the second therapeutic agent is Alpharadin which is administered by intravenous infusion at a dose of about 25 to about 50 kBq/kg every 4 weeks. In other embodiments, the second therapeutic agent is $^{177}$Lu-J591 which is administered by intravenous infusion at a dose of about 30 mCi/m$^2$ to about 70 mCi/m$^2$.

Outcome Measures:

Overall and 12-week PSA response (decrease of PSA by ≥50% from basesline); Time to PSA Progression; overall survival (OS); PFS (Progression-free survival by CT/MRI/radio-tracer); quality of life (QOL); side-effects; pharmacokinetics (PK); tumor response and/or disease control; proportion of patients that have complete or partial response or stable disease at defined time points; biomarkers predictive of clinical response.

Eligibility:

Male subjects that are 18 years and older.

Inclusion Criteria:

Histologically or cytologically confirmed adenocarcinoma of the prostate (e.g. metastatic castration-resistant prostate cancer, non-metastatic castration-resistant prostate cancer, metastatic castration-sensitive prostate cancer, non-metastatic castration-sensitive prostate cancer or high-risk localized prostate cancer); castration-resistant prostate cancer demonstrated during continuous androgen deprivation therapy (ADT)/post orchiectomy, defined as 3 consecutive rises of PSA, 1 week apart, resulting in two 50% increases over the nadir, with the last PSA>2 ng/mL; maintain castrate levels of testosterone (<50 ng/dL [1.72 nmol/L]) within 4 weeks of randomization and throughout the study; patients currently receiving bone loss prevention treatment with bone-sparing agents (e.g., bisphosphonates, denosumab [PROLIA™ denosumab]) must be on stable doses for at least 4 weeks prior to randomization; patients who received a first generation anti-androgen (e.g., bicalutamide, flutamide, nilutamide) as part of an initial combined androgen blockade therapy or as second-line hormonal therapy must show continuing disease (PSA) progression off the anti-androgen for at least 4 weeks prior to randomization; at least 4 weeks must have elapsed from the use of 5-α reductase inhibitors (e.g., dutasteride, finasteride, aminoglutethamide), estrogens, and any other anti-cancer therapy prior to randomization, including chemotherapy given in the adjuvant/neoadjuvant setting (e.g., clinical trial); at least 4 weeks must have elapsed from major surgery or radiation therapy prior to randomization.

Exclusion Criteria:

Prior second-generation antiandrogen therapy, CNS metastasis, prior history of seizure.

Example 17

Clinical Trial for the Combination of an Anti-Androgen with a Kinase Inhibitor

A non-limiting example of a prostate cancer clinical trial in humans involving the combination of 4-[7-(6-cyano-5-trifluoromethylpyridin-3-yl)-8-oxo-6-thioxo-5,7-diazaspiro[3.4]oct-5-yl]-2-fluoro-N-methylbenzamide and a kinase inhibitor is described below.

Purpose:

The purposes of this study is to assess the safety and efficacy of a combination of 4-[7-(6-cyano-5-trifluoromethylpyridin-3-yl)-8-oxo-6-thioxo-5,7-diazaspiro[3.4]oct-5-yl]-2-fluoro-N-methylbenzamide and a kinase inhibitor in humans with prostate cancer (e.g. post-abiraterone acetate treated metastatic castration-resistant prostate cancer, metastatic castration-resistant prostate cancer, non-metastatic castration-resistant prostate cancer, metastatic castration-sensitive prostate cancer, non-metastatic castration-sensitive prostate cancer or high-risk localized prostate cancer), collect information on any side effects the combination therapy may cause, and evaluate the pharmacokinetic properties of the compounds in the context of combination therapy.

Intervention:

Patients are administered 4-[7-(6-cyano-5-trifluoromethylpyridin-3-yl)-8-oxo-6-thioxo-5,7-diazaspiro[3.4]oct-5-yl]-2-fluoro-N-methylbenzamide at a dose of 240 mg per day. However, dose adjustment of 4-[7-(6-cyano-5-trifluoromethylpyridin-3-yl)-8-oxo-6-thioxo-5,7-diazaspiro[3.4]oct-5-yl]-2-fluoro-N-methylbenzamide (120 mg to 480 mg per day) will be considered during the trial if deemed necessary. The patients will be also be administered a kiase inhibitor in addition to 4-[7-(6-cyano-5-trifluoromethylpyridin-3-yl)-8-oxo-6-thioxo-5,7-diazaspiro[3.4]oct-5-yl]-2-fluoro-N-methylbenzamide. In some embodiments, the kinase inhibitor is cabozantinib which is administered orally at a dose of about 40 mg per day to about 100 mg per day. In other embodiments, the kinase inhibitor is erlotinib which is administered orally at a dose of about 100 mg to about 150 mg. In some other embodiments, the kinase inhibitor is gefitinib which is administered orally at a dose of about 250 mg per day. In yet some other embodiments, the kinase inhibitor is trametinib which is administered orally at a dose of about 1 mg to about 2 mg.

Outcome Measures:

Overall and 12-week PSA response (decrease of PSA by ≥50% from baseline); Time to PSA Progression; overall survival (OS); PFS (Progression-free survival by CT/MRI/radio-tracer); quality of life (QOL); side-effects; pharmacokinetics (PK); tumor response and/or disease control; proportion of patients that have complete or partial response or stable disease at defined time points; biomarkers predictive of clinical response.

Eligibility:

Male subjects that are 18 years and older.

Inclusion Criteria:

Histologically or cytologically confirmed adenocarcinoma of the prostate (e.g. post-abiraterone acetate treated metastatic castration-resistant prostate cancer, metastatic castration-resistant prostate cancer, non-metastatic castration-resistant prostate cancer, metastatic castration-sensitive prostate cancer, non-metastatic castration-sensitive prostate cancer or high-risk localized prostate cancer); castration-resistant prostate cancer demonstrated during continuous androgen deprivation therapy (ADT)/post orchiectomy, defined as 3 consecutive rises of PSA, 1 week apart, resulting in two 50% increases over the nadir, with the last PSA>2 ng/mL; maintain castrate levels of testosterone (<50 ng/dL [1.72 nmol/L]) within 4 weeks of randomization and throughout the study; patients currently receiving bone loss prevention treatment with bone-sparing agents (e.g., bisphosphonates, denosumab [PROLIA™ denosumab]) must be on stable doses for at least 4 weeks prior to randomization; patients who received a first generation anti-androgen (e.g., bicalutamide, flutamide, nilutamide) as part of an initial combined androgen blockade therapy or as second-line hormonal therapy must show continuing disease (PSA) progression off the anti-androgen for at least 4 weeks prior to randomization; at least 4 weeks must have elapsed from the use of 5-α reductase inhibitors (e.g., dutasteride, finasteride, aminoglutethamide), estrogens, and any other anti-cancer therapy prior to randomization, including chemotherapy given in the adjuvant/neoadjuvant setting (e.g., clinical trial); at least 4 weeks must have elapsed from major surgery or radiation therapy prior to randomization.

Exclusion Criteria:

Prior second-generation antiandrogen therapy, CNS metastasis, prior history of seizure.

Example 18

Clinical Trial for the Combination of an Anti-Androgen with Immunotherapy

A non-limiting example of a prostate cancer clinical trial in humans involving the combination of 4-[7-(6-cyano-5-trifluoromethylpyridin-3-yl)-8-oxo-6-thioxo-5,7-diazaspiro[3.4]oct-5-yl]-2-fluoro-N-methylbenzamide and immunotherapy is described below.

Purpose:

The purposes of this study is to assess the safety and efficacy of a combination of 4-[7-(6-cyano-5-trifluoromethylpyridin-3-yl)-8-oxo-6-thioxo-5,7-diazaspiro[3.4]oct-5-yl]-2-fluoro-N-methylbenzamide and PROVENGE™ (sipuleucel-T), PROSTVAC™ (rilimogene galvacirepvec/rilimogene glafolivec), Ipilimumab, or a PD-1 inhibitor in humans with prostate cancer (e.g. metastatic castration-resistant prostate cancer, non-metastatic castration-resistant prostate cancer, metastatic castration-sensitive prostate cancer, non-metastatic castration-sensitive prostate cancer or high-risk localized prostate cancer), collect information on any side effects the combination therapy may cause, and evaluate the pharmacokinetic properties of the compounds in the context of combination therapy.

Intervention:

Patients are administered 4-[7-(6-cyano-5-trifluoromethylpyridin-3-yl)-8-oxo-6-thioxo-5,7-diazaspiro[3.4]oct-5-yl]-2-fluoro-N-methylbenzamide at a dose of 240 mg per day. However, dose adjustment of 4-[7-(6-cyano-5-trifluoromethylpyridin-3-yl)-8-oxo-6-thioxo-5,7-diazaspiro[3.4]oct-5-yl]-2-fluoro-N-methylbenzamide (120 mg to 480 mg per day) will be considered during the trial if deemed necessary. The patients will also be administered a second therapeutic agent in addition to 4-[7-(6-cyano-5-trifluoromethylpyridin-3-yl)-8-oxo-6-thioxo-5,7-diazaspiro[3.4]oct-5-yl]-2-fluoro-N-methylbenzamide. In some embodiments, the additional therapeutic agent is Ipilimumab which is administered by intravenous infusion at a dose of about 1.5 mg/kg to about 3.0 mg/kg IV every 3 weeks for a total of 4 doses. In other embodiments, the additional therapeutic agent is the PD-1 inhibitor BMS-936558 which is administered by intravenous infusion at a dose of about 1.0 mg/kg to about 10 mg/kg on days 1, and 29 of 6-week cycles. In some other embodiments, the additional therapeutic agent is PROVENGE™ (sipuleucel-T) which is administered as 3 doses, given at approximately 2 week intervals. In yet some other embodiments, the additional therapeutic agent is PROSTVAC™ (rilimogene galvacirepvec/rilimogene glafolivec) which is administered by subcutaneous injection on days 1, 14, 28, 56, 84, 112, and 140. Priming immunization with rV-PSA-TRICOM ($2\times10^8$ pfu) with subsequent boosts using rF-PSA-TRICOM ($1\times10^9$ pfu) with or without GM-CSF at 100 μg subcutaneously on the day of each vaccination.

Outcome Measures:

Overall and 12-week PSA response (decrease of PSA by ≥50% from baseline); Time to PSA Progression; overall survival (OS); PFS (Progression-free survival by CT/MRI/radio-tracer); quality of life (QOL); side-effects; pharmacokinetics (PK); tumor response and/or disease control; proportion of patients that have complete or partial response or stable disease at defined time points; biomarkers predictive of clinical response.

Eligibility:

Male subjects that are 18 years and older.

Inclusion Criteria:

Histologically or cytologically confirmed adenocarcinoma of the prostate (e.g. metastatic castration-resistant prostate cancer, non-metastatic castration-resistant prostate cancer, metastatic castration-sensitive prostate cancer, non-metastatic castration-sensitive prostate cancer or high-risk localized prostate cancer); castration-resistant prostate cancer demonstrated during continuous androgen deprivation therapy (ADT)/post orchiectomy, defined as 3 consecutive rises of PSA, 1 week apart, resulting in two 50% increases over the nadir, with the last PSA>2 ng/mL; maintain castrate levels of testosterone (<50 ng/dL [1.72 nmol/L]) within 4 weeks of randomization and throughout the study; patients currently receiving bone loss prevention treatment with bone-sparing agents (e.g., bisphosphonates, denosumab [PROLIA™ denosumab]) must be on stable doses for at least 4 weeks prior to randomization; patients who received a first generation anti-androgen (e.g., bicalutamide, flutamide, nilutamide) as part of an initial combined androgen blockade therapy or as second-line hormonal therapy must show continuing disease (PSA) progression off the anti-androgen for at least 4 weeks prior to randomization; at least 4 weeks must have elapsed from the use of 5-α reductase inhibitors (e.g., dutasteride, finasteride, aminoglutethamide), estrogens, and any other anti-cancer therapy prior to randomization, including chemotherapy given in the adjuvant/neoadjuvant setting (e.g., clinical trial); at least 4 weeks must have elapsed from major surgery or radiation therapy prior to randomization.

Exclusion Criteria:

Prior second-generation antiandrogen therapy, CNS metastasis, prior history of seizure.

Example 19

Clinical Trial for the Combination of an Anti-Androgen with Chemotherapy

A non-limiting example of a prostate cancer clinical trial in humans involving the combination of 4-[7-(6-cyano-5-trifluoromethylpyridin-3-yl)-8-oxo-6-thioxo-5,7-diazaspiro[3.4]oct-5-yl]-2-fluoro-N-methylbenzamide and chemotherapy is described below.

Purpose:

The purposes of this study is to assess the safety and efficacy of a combination of 4-[7-(6-cyano-5-trifluoromethylpyridin-3-yl)-8-oxo-6-thioxo-5,7-diazaspiro[3.4]oct-5-yl]-2-fluoro-N-methylbenzamide and a taxane or tubulin inhibitor in males with metastatic castration-resistant prostate cancer or high-risk localized prostate cancer, collect information on any side effects the combination therapy may cause, and evaluate the pharmacokinetic properties of the compounds in the context of combination therapy.

Intervention:

Patients are administered 4-[7-(6-cyano-5-trifluoromethylpyridin-3-yl)-8-oxo-6-thioxo-5,7-diazaspiro[3.4]oct-5-yl]-2-fluoro-N-methylbenzamide at a dose of 240 mg per day. However, dose adjustment of 4-[7-(6-cyano-5-trifluoromethylpyridin-3-yl)-8-oxo-6-thioxo-5,7-diazaspiro[3.4]oct-5-yl]-2-fluoro-N-methylbenzamide (120 mg to 480 mg per day) will be considered during the trial if deemed necessary. The patients will be administered a second therapeutic agent in addition to 4-[7-(6-cyano-5-trifluoromethylpyridin-3-yl)-8-oxo-6-thioxo-5,7-diazaspiro[3.4]oct-5-yl]-2-fluoro-N-methylbenzamide. In some embodiments, the second therapeutic agent is docetaxel which is administered by intravenous infusion at a dose of about 35 mg/m$^2$ to about 75 mg/m$^2$ every 3 weeks. In other embodiments, the second therapeutic agent is cabazitaxel which is administered by intravenous infusion at a dose of about 13 mg/m$^2$ to about 25 mg/m$^2$ every 3 weeks.

Outcome Measures:

Overall and 12-week PSA response (decrease of PSA by ≥50% from basesline); Time to PSA Progression; overall survival (OS); PFS (Progression-free survival by CT/MRI/radio-tracer); quality of life (QOL); side-effects; pharmacokinetics (PK); tumor response and/or disease control; proportion of patients that have complete or partial response or stable disease at defined time points; biomarkers predictive of clinical response.

Eligibility:

Male subjects that are 18 years and older.

Inclusion Criteria:

Histologically or cytologically confirmed adenocarcinoma of the prostate (e.g. metastatic castration-resistant prostate cancer or high-risk localized prostate cancer); castration-resistant prostate cancer demonstrated during continuous androgen deprivation therapy (ADT)/post orchiectomy, defined as 3 consecutive rises of PSA, 1 week apart, resulting in two 50% increases over the nadir, with the last PSA>2 ng/mL; maintain castrate levels of testosterone (<50 ng/dL [1.72 nmol/L]) within 4 weeks of randomization and throughout the study; patients currently receiving bone loss prevention treatment with bone-sparing agents (e.g., bisphosphonates, denosumab [PROLIA™ denosumab]) must be on stable doses for at least 4 weeks prior to randomization; patients who received a first generation anti-androgen (e.g., bicalutamide, flutamide, nilutamide) as part of an initial combined androgen blockade therapy or as second-line hormonal therapy must show continuing disease (PSA) progression off the anti-androgen for at least 4 weeks prior to randomization; at least 4 weeks must have elapsed from the use of 5-α reductase inhibitors (e.g., dutasteride, finasteride, aminoglutethamide), estrogens, and any other anti-cancer therapy prior to randomization, including chemotherapy given in the adjuvant/neoadjuvant setting (e.g., clinical trial); at least 4 weeks must have elapsed from major surgery or radiation therapy prior to randomization.

Exclusion Criteria:

Prior second-generation antiandrogen therapy, CNS metastasis, prior history of seizure.

Example 20

Clinical Trial for the Combination of an Anti-Androgen with an Anti-STEAP-1 Antibody Drug Conjugate A non-limiting example of a prostate cancer clinical trial in humans involving the combination of 4-[7-(6-cyano-5-trifluoromethylpyridin-3-yl)-8-oxo-6-thioxo-5,7-diazaspiro[3.4]oct-5-yl]-2-fluoro-N-methylbenzamide and an anti-STEAP-1 antibody drug conjugate is described below.

Purpose:

The purposes of this study is to assess the safety and efficacy of a combination of 4-[7-(6-cyano-5-trifluoromethylpyridin-3-yl)-8-oxo-6-thioxo-5,7-diazaspiro[3.4]oct-5-yl]-2-fluoro-N-methylbenzamide and an anti-STEAP-1 antibody drug conjugate in males with prostate cancer (e.g. metastatic castration-resistant prostate cancer, non-metastatic castration-resistant prostate cancer, metastatic castration-sensitive prostate cancer, non-metastatic castration-sensitive prostate cancer or high-risk localized prostate cancer), collect information on any side effects the combination therapy may cause, and evaluate the pharmacokinetic properties of the compounds in the context of combination therapy.

Intervention:

Patients are administered 4-[7-(6-cyano-5-trifluoromethylpyridin-3-yl)-8-oxo-6-thioxo-5,7-diazaspiro[3.4]oct-5-yl]-2-fluoro-N-methylbenzamide at a dose of 240 mg per day. However, dose adjustment of 4-[7-(6-cyano-5-trifluoromethylpyridin-3-yl)-8-oxo-6-thioxo-5,7-diazaspiro[3.4]oct-5-yl]-2-fluoro-N-methylbenzamide (120 mg to 480 mg per day) will be considered during the trial if deemed necessary. Patients also will be administered an anti-STEAP-1 antibody drug conjugate.

Outcome Measures:

Overall and 12-week PSA response (decrease of PSA by ≥50% from basesline); Time to PSA Progression; overall survival (OS); PFS (Progression-free survival by CT/MRI/radio-tracer); quality of life (QOL); side-effects; pharmacokinetics (PK); tumor response and/or disease control; proportion of patients that have complete or partial response or stable disease at defined time points; biomarkers predictive of clinical response.

Eligibility:

Male subjects that are 18 years and older.

Inclusion Criteria:

Histologically or cytologically confirmed adenocarcinoma of the prostate (e.g. metastatic castration-resistant prostate cancer, non-metastatic castration-resistant prostate cancer, metastatic castration-sensitive prostate cancer, non-metastatic castration-sensitive prostate cancer or high-risk localized prostate cancer); castration-resistant prostate cancer demonstrated during continuous androgen deprivation therapy (ADT)/post orchiectomy, defined as 3 consecutive rises of PSA, 1 week apart, resulting in two 50% increases over the nadir, with the last PSA>2 ng/mL; maintain castrate levels of testosterone (<50 ng/dL [1.72 nmol/L]) within 4 weeks of randomization and throughout the study; patients currently receiving bone loss prevention treatment with bone-sparing agents (e.g., bisphosphonates, denosumab [PRO-LIA™ denosumab]) must be on stable doses for at least 4 weeks prior to randomization; patients who received a first generation anti-androgen (e.g., bicalutamide, flutamide, nilutamide) as part of an initial combined androgen blockade therapy or as second-line hormonal therapy must show continuing disease (PSA) progression off the anti-androgen for at least 4 weeks prior to randomization; at least 4 weeks must have elapsed from the use of 5-α reductase inhibitors (e.g., dutasteride, finasteride, aminoglutethamide), estrogens, and any other anti-cancer therapy prior to randomization, including chemotherapy given in the adjuvant/neoadjuvant setting (e.g., clinical trial); at least 4 weeks must have elapsed from major surgery or radiation therapy prior to randomization.

Exclusion Criteria:
Prior second-generation antiandrogen therapy, CNS metastasis, prior history of seizure.

Example 21

Clinical Trial for the Combination of an Anti-Androgen with a Heat Shock Protein (HSP) Inhibitor A non-limiting example of a prostate cancer clinical trial in humans involving the combination of 4-[7-(6-cyano-5-trifluoromethylpyridin-3-yl)-8-oxo-6-thioxo-5,7-diazaspiro [3.4]oct-5-yl]-2-fluoro-N-methylbenzamide and a HSP inhibitor is described below.

Purpose:
The purposes of this study is to assess the safety and efficacy of a combination of 4-[7-(6-cyano-5-trifluoromethylpyridin-3-yl)-8-oxo-6-thioxo-5,7-diazaspiro[3.4]oct-5-yl]-2-fluoro-N-methylbenzamide and a HSP inhibitor (e.g. HSP90 or HSP27) in males with prostate cancer (e.g. metastatic castration-resistant prostate cancer, non-metastatic castration-resistant prostate cancer, metastatic castration-sensitive prostate cancer, non-metastatic castration-sensitive prostate cancer or high-risk localized prostate cancer), collect information on any side effects the combination therapy may cause, and evaluate the pharmacokinetic properties of the compounds in the context of combination therapy.

Intervention:
Patients are administered 4-[7-(6-cyano-5-trifluoromethylpyridin-3-yl)-8-oxo-6-thioxo-5,7-diazaspiro[3.4]oct-5-yl]-2-fluoro-N-methylbenzamide at a dose of 240 mg per day. However, dose adjustment of 4-[7-(6-cyano-5-trifluoromethylpyridin-3-yl)-8-oxo-6-thioxo-5,7-diazaspiro[3.4]oct-5-yl]-2-fluoro-N-methylbenzamide (120 mg to 480 mg per day) will be considered during the trial if deemed necessary. The patients will also be administered a HSP inhibitor in addition to 4-[7-(6-cyano-5-trifluoromethylpyridin-3-yl)-8-oxo-6-thioxo-5,7-diazaspiro[3.4]oct-5-yl]-2-fluoro-N-methylbenzamide. In some embodiments, the HSP inhibitor is OGX-011 (Custirsen) which is administered by intravenous infusion at a dose of about 320 mg to about 640 mg every week. In other embodiments, the HSP inhibitor is OGX-427 which is administered by intravenous infusion at a loading dose of about 300 mg to about 600 mg followed by about 500 mg to about 1000 mg every week.

Outcome Measures:
Overall and 12-week PSA response (decrease of PSA by ≥50% from baseline); Time to PSA Progression; overall survival (OS); PFS (Progression-free survival by CT/MRI/ radio-tracer); quality of life (QOL); side-effects; pharmacokinetics (PK); tumor response and/or disease control; proportion of patients that have complete or partial response or stable disease at defined time points; biomarkers predictive of clinical response.

Eligibility:
Male subjects that are 18 years and older.

Inclusion Criteria:
Histologically or cytologically confirmed adenocarcinoma of the prostate (e.g. metastatic castration-resistant prostate cancer, non-metastatic castration-resistant prostate cancer, metastatic castration-sensitive prostate cancer, non-metastatic castration-sensitive prostate cancer or high-risk localized prostate cancer); castration-resistant prostate cancer demonstrated during continuous androgen deprivation therapy (ADT)/post orchiectomy, defined as 3 consecutive rises of PSA, 1 week apart, resulting in two 50% increases over the nadir, with the last PSA>2 ng/mL; maintain castrate levels of testosterone (<50 ng/dL [1.72 nmol/L]) within 4 weeks of randomization and throughout the study; patients currently receiving bone loss prevention treatment with bone-sparing agents (e.g., bisphosphonates, denosumab [PRO-LIA™ denosumab]) must be on stable doses for at least 4 weeks prior to randomization; patients who received a first generation anti-androgen (e.g., bicalutamide, flutamide, nilutamide) as part of an initial combined androgen blockade therapy or as second-line hormonal therapy must show continuing disease (PSA) progression off the anti-androgen for at least 4 weeks prior to randomization; at least 4 weeks must have elapsed from the use of 5-α reductase inhibitors (e.g., dutasteride, finasteride, aminoglutethamide), estrogens, and any other anti-cancer therapy prior to randomization, including chemotherapy given in the adjuvant/neoadjuvant setting (e.g., clinical trial); at least 4 weeks must have elapsed from major surgery or radiation therapy prior to randomization Exclusion Criteria:
Prior second-generation antiandrogen therapy, CNS metastasis, prior history of seizure.

The examples and embodiments described herein are for illustrative purposes only and various modifications or changes suggested to persons skilled in the art are to be included within the spirit and purview of this application and scope of the appended claims.

What is claimed is:
1. A pharmaceutical composition comprising a nonaqueous, lipid-based solution of the compound of Formula (I), or a pharmaceutically acceptable salt thereof, in a softgel capsule, wherein the composition comprises the compound of Formula (I), or a pharmaceutically acceptable salt thereof, vitamin E d-α-tocopheryl polyethylene glycol 1000 succinate NF (Vitamin E TPGS), polyethylene glycol 400 NF/EP (PEG 400), glycerol monocaprylocaprate EP and caprylocaproyl macroglycerides EP/NF

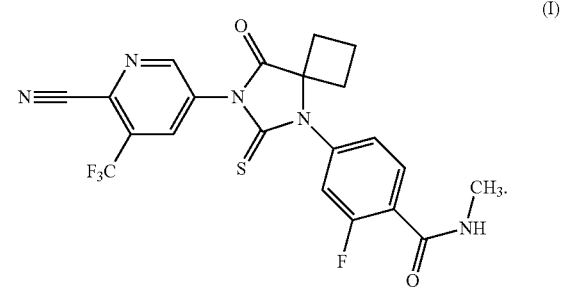 [SMILES: CNC(=O)c1ccc(N2C(=S)N(c3cnc(C#N)c(C(F)(F)F)c3)C(=O)C23CCC3)cc1F]

(I)

2. The pharmaceutical composition of claim 1, wherein the nonaqueous, lipid-based solution the compound of Formula (I), or a pharmaceutically acceptable salt thereof, comprises about 3 wt % of the compound of Formula (I), or a pharmaceutically acceptable salt thereof,

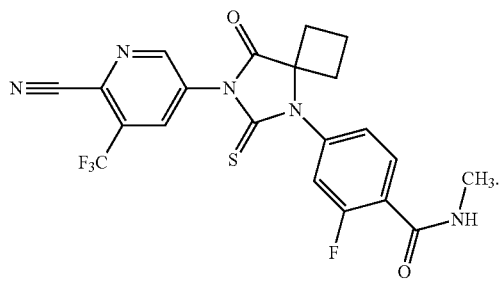
(I)

3. The pharmaceutical composition of 1, wherein the softgel capsule shell comprises gelatin NF/EP, a 50:50 sorbitol/glycerin blend USP/EP, and purified water USP/EP.

4. The pharmaceutical composition of claim 1, wherein a single unit dosage comprises about 30 mg of the compound of Formula (I), or a pharmaceutically acceptable salt thereof,

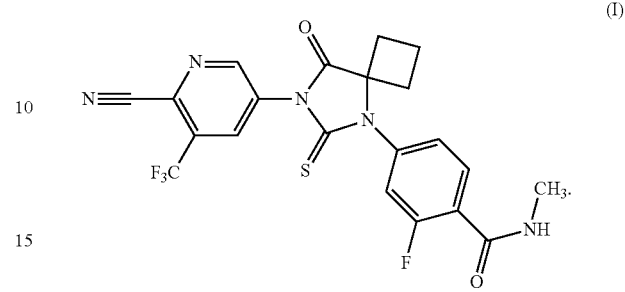
(I)

\* \* \* \* \*